United States Patent
Bedu-Addo et al.

(10) Patent No.: US 11,612,652 B2
(45) Date of Patent: Mar. 28, 2023

(54) LIPIDS AS SYNTHETIC VECTORS TO ENHANCE ANTIGEN PROCESSING AND PRESENTATION EX-VIVO IN DENDRITIC CELL THERAPY

(71) Applicant: PDS Biotechnology Corporation, North Brunswick, NJ (US)

(72) Inventors: Frank Bedu-Addo, Carmel, IN (US); Greg Conn, Madrid (ES); Siva K. Gandhapudi, Blue Ash, OH (US); Martin Ward, Lexington, KY (US); Jerold Woodward, Lexington, KY (US)

(73) Assignee: PDS Biotechnology Corporation, North Brunswick, NJ (US)

( * ) Notice: Subject to any disclaimer, the term of this patent is extended or adjusted under 35 U.S.C. 154(b) by 41 days.

(21) Appl. No.: 15/775,680

(22) PCT Filed: Nov. 14, 2016

(86) PCT No.: PCT/US2016/061829
§ 371 (c)(1),
(2) Date: May 11, 2018

(87) PCT Pub. No.: WO2017/083820
PCT Pub. Date: May 18, 2017

(65) Prior Publication Data
US 2018/0353599 A1   Dec. 13, 2018

Related U.S. Application Data

(60) Provisional application No. 62/404,504, filed on Oct. 5, 2016, provisional application No. 62/254,794, filed on Nov. 13, 2015.

(51) Int. Cl.
| | |
|---|---|
| *A61K 39/39* | (2006.01) |
| *A61K 35/14* | (2015.01) |
| *C12N 5/0784* | (2010.01) |
| *A61P 31/00* | (2006.01) |
| *A61P 35/00* | (2006.01) |
| *A61K 39/00* | (2006.01) |
| *A61K 39/12* | (2006.01) |

(52) U.S. Cl.
CPC .............. *A61K 39/39* (2013.01); *A61K 35/14* (2013.01); *A61K 39/00117* (2018.08); *A61K 39/12* (2013.01); *A61P 31/00* (2018.01); *A61P 35/00* (2018.01); *C12N 5/0639* (2013.01); *A61K 2039/5154* (2013.01); *A61K 2039/55505* (2013.01); *A61K 2039/55522* (2013.01); *A61K 2039/55555* (2013.01); *A61K 2039/55572* (2013.01); *A61K 2039/57* (2013.01); *A61K 2039/572* (2013.01); *A61K 2039/585* (2013.01); *C12N 2710/20034* (2013.01)

(58) Field of Classification Search
None
See application file for complete search history.

(56) References Cited

U.S. PATENT DOCUMENTS

| | | |
|---|---|---|
| 2,167,480 A | 7/1939 | Hansell |
| 4,703,004 A | 10/1987 | Hopp et al. |
| 5,264,618 A | 11/1993 | Felgner et al. |
| 5,283,185 A | 2/1994 | Epand et al. |
| 5,334,761 A | 8/1994 | Gebeyehu et al. |
| 5,459,127 A | 10/1995 | Felgner et al. |
| 6,008,202 A | 12/1999 | Huang et al. |
| 6,124,270 A | 9/2000 | Haensler |
| 6,183,745 B1 | 2/2001 | Tindle et al. |
| 6,214,804 B1 | 4/2001 | Felgner et al. |
| 6,419,931 B1 | 7/2002 | Vitiello et al. |
| 6,464,980 B1 | 10/2002 | Fikes et al. |
| 6,586,409 B1 | 7/2003 | Wheeler |
| 6,610,321 B2 | 8/2003 | Huang et al. |
| 6,649,170 B1 | 11/2003 | Lindblad et al. |
| 6,693,086 B1 | 2/2004 | Dow et al. |
| 6,710,035 B2 | 3/2004 | Felgner et al. |

(Continued)

FOREIGN PATENT DOCUMENTS

| | | |
|---|---|---|
| CN | 1909918 A | 2/2007 |
| CN | 101065350 A | 10/2007 |

(Continued)

OTHER PUBLICATIONS

Yu et al., Novel Chlamydia muridarum T Cell Antigens Induce Protective Immunity against Lung and Genital Tract Infection in Murine models, 2009, Journal of Immunology, vol. 182, pp. 1602-1608.*
Vasievich et al., Enantiospecific adjuvant activity of cationic lipid DOTAP in cancer vaccine, 2011, Cancer Immunol Immunotherapy, vol. 60, No. 5, pp. 629-638.*
Christensen, D. et al., "Cationic Liposomes as Vaccine Adjuvants", Expert Review of Vaccines, vol. 6, No. 5, 2007, pp. 785-796.
International Search Report and Written Opinion from corresponding International Application No. PCT/US2016/061829, dated Feb. 24, 2017.

(Continued)

Primary Examiner — Benjamin P Blumel
(74) Attorney, Agent, or Firm — DLA Piper LLP (US)

(57) ABSTRACT

The invention covers the use of certain classes of lipids including cationic lipids in ex-vivo dendritic cell therapies. The cationic lipids enhance antigen uptake, processing and presentation of the processed antigens by dendritic cells to CD8+ and CD4+ T-cells via the MHC classes I and II presentation pathways respectively. Antigen uptake via cationic lipid by dendritic cells result in significant lowering of the population of the immune suppressive regulatory T cells in the tumors and a significant increase of the tumor targeting cytotoxic T-cells. Loss of regulatory T cells and increase of tumor specific cytotoxic cells are conducive to effective elimination of the tumors.

6 Claims, 21 Drawing Sheets
Specification includes a Sequence Listing.

(56) References Cited

U.S. PATENT DOCUMENTS

| | | |
|---|---|---|
| 6,780,421 B1 | 8/2004 | Haensler et al. |
| 6,852,334 B1 | 2/2005 | Cullis et al. |
| 7,001,614 B2 | 2/2006 | Smyth-Templeton et al. |
| 7,105,574 B1 | 9/2006 | Wheeler |
| 7,303,881 B2 | 12/2007 | Huang et al. |
| 7,488,791 B2 | 2/2009 | Maillere et al. |
| 8,877,206 B2 | 11/2014 | Chen et al. |
| 9,102,950 B2 | 8/2015 | Hartikka et al. |
| 9,789,129 B2 | 10/2017 | Vasievich et al. |
| 10,155,049 B2 | 12/2018 | Bonnet et al. |
| 10,286,064 B2 | 5/2019 | Johnson et al. |
| 11,401,306 B2 | 8/2022 | Bedu-Addo et al. |
| 2001/0026937 A1* | 10/2001 | Punnonen ............ C12N 5/0639 435/366 |
| 2002/0007173 A1 | 1/2002 | Kundig et al. |
| 2002/0187105 A1 | 12/2002 | Zou et al. |
| 2003/0008813 A1 | 1/2003 | Felgner et al. |
| 2003/0229040 A1 | 12/2003 | Kasid et al. |
| 2004/0106551 A1 | 6/2004 | Khleif et al. |
| 2004/0157791 A1 | 8/2004 | Dow et al. |
| 2004/0185057 A1 | 9/2004 | Kirkby et al. |
| 2004/0203051 A1 | 10/2004 | Simard et al. |
| 2005/0025822 A1 | 2/2005 | Wong et al. |
| 2005/0176672 A1 | 8/2005 | Scheule et al. |
| 2005/0220814 A1 | 10/2005 | Dominowski et al. |
| 2005/0245446 A1 | 11/2005 | Hailes et al. |
| 2006/0008472 A1 | 1/2006 | Huang et al. |
| 2006/0051405 A1 | 3/2006 | MacLachlan et al. |
| 2006/0083780 A1 | 4/2006 | Heyes et al. |
| 2006/0159738 A1 | 7/2006 | Graham et al. |
| 2006/0165708 A1 | 7/2006 | Mayumi et al. |
| 2006/0171956 A1 | 8/2006 | Bareholz et al. |
| 2006/0182793 A1 | 8/2006 | Bachmann et al. |
| 2006/0204566 A1 | 9/2006 | Smyth-Templeton et al. |
| 2006/0223769 A1 | 10/2006 | Dow et al. |
| 2006/0251726 A1 | 11/2006 | Lin et al. |
| 2006/0263804 A1 | 11/2006 | Robinson et al. |
| 2006/0275777 A1 | 12/2006 | Waelti |
| 2006/0286124 A1 | 12/2006 | Burt et al. |
| 2007/0014807 A1 | 1/2007 | Maida, III |
| 2007/0059318 A1 | 3/2007 | Balu-Iyer et al. |
| 2007/0066552 A1 | 3/2007 | Clarke et al. |
| 2007/0207526 A1 | 9/2007 | Coit et al. |
| 2008/0014251 A1 | 1/2008 | Benz et al. |
| 2008/0014254 A1 | 1/2008 | Platscher et al. |
| 2008/0049957 A1 | 2/2008 | Topholm |
| 2008/0206286 A1 | 2/2008 | Yu |
| 2008/0131455 A1 | 6/2008 | Huang et al. |
| 2008/0152665 A1 | 6/2008 | Leclerc et al. |
| 2008/0248044 A1 | 10/2008 | Choppin et al. |
| 2009/0001705 A1 | 1/2009 | Fischer et al. |
| 2009/0017057 A1* | 1/2009 | Chen ................ A61K 39/0011 424/193.1 |
| 2009/0053251 A1* | 2/2009 | Pogue-Caley .......... A61P 31/04 424/184.1 |
| 2010/0086584 A1 | 4/2010 | Callejo et al. |
| 2010/0099745 A1 | 4/2010 | Sambhara et al. |
| 2010/0112002 A1 | 5/2010 | Lien et al. |
| 2010/0158939 A1 | 6/2010 | Sambhara et al. |
| 2010/0203080 A1 | 8/2010 | Maillere et al. |
| 2010/0221223 A1 | 9/2010 | Tsutsui et al. |
| 2010/0239657 A1 | 9/2010 | Kim et al. |
| 2010/0266547 A1 | 10/2010 | Benedict |
| 2010/0297144 A1 | 11/2010 | Roden |
| 2011/0110972 A1 | 5/2011 | Vasievich et al. |
| 2011/0117141 A1 | 5/2011 | Huang et al. |
| 2011/0158952 A1 | 6/2011 | Beach et al. |
| 2011/0305713 A1 | 12/2011 | Munn et al. |
| 2012/0148622 A1 | 6/2012 | Tenoever |
| 2013/0129761 A1 | 5/2013 | Garcia-Sastre et al. |
| 2013/0225663 A1 | 8/2013 | Brown |
| 2013/0243723 A1 | 9/2013 | Hadden et al. |
| 2015/0079155 A1 | 3/2015 | Jensen et al. |
| 2015/0093410 A1 | 4/2015 | Chen et al. |
| 2015/0110823 A1 | 4/2015 | Bedu-Addo et al. |
| 2015/0132340 A1 | 5/2015 | Johnson et al. |
| 2015/0250872 A1 | 9/2015 | Bedu-Addo et al. |
| 2015/0283219 A1 | 10/2015 | Langlade Demoyen et al. |
| 2015/0343062 A1 | 12/2015 | Kuboyama et al. |
| 2016/0168227 A1 | 6/2016 | Kallen et al. |
| 2016/0193316 A1 | 7/2016 | Sette et al. |
| 2016/0251406 A1 | 9/2016 | Schlom et al. |
| 2017/0296639 A1 | 10/2017 | Ma et al. |
| 2018/0015114 A1 | 1/2018 | Vasievich et al. |
| 2018/0094032 A1 | 4/2018 | Bedu-Addo et al. |
| 2018/0353599 A1 | 12/2018 | Bedu-Addo et al. |
| 2019/0321321 A1* | 10/2019 | Bedu-Addo ............ A61K 39/39 |
| 2019/0358319 A1* | 11/2019 | Bedu-Addo ............ A61P 31/00 |

FOREIGN PATENT DOCUMENTS

| | | |
|---|---|---|
| CN | 101193655 A | 6/2008 |
| CN | 101702882 A | 5/2010 |
| CN | 102137675 A | 7/2011 |
| CN | 104189897 A | 12/2014 |
| CN | 104703588 A | 6/2015 |
| CN | 105163753 A | 12/2015 |
| CN | 105920599 A | 9/2016 |
| CN | 111217918 A | 6/2020 |
| EP | 2167480 A2 | 3/2010 |
| JP | H06510051 A | 11/1994 |
| JP | H09502086 A | 3/1997 |
| JP | H10501822 A | 2/1998 |
| JP | 2002537102 A | 11/2002 |
| JP | 2002542341 A | 12/2002 |
| JP | 2003506095 A | 2/2003 |
| JP | 2003509035 A | 3/2003 |
| JP | 2004508012 A | 3/2004 |
| JP | 2006513979 A | 4/2006 |
| JP | 2006527762 A | 12/2006 |
| JP | 2007238559 A | 9/2007 |
| JP | 2008521757 A | 6/2008 |
| JP | 2010-522206 A | 7/2010 |
| JP | 2010537961 A | 12/2010 |
| JP | 2011-518170 A | 6/2011 |
| JP | 2012526853 A | 11/2012 |
| JP | 2014527965 A | 10/2014 |
| RU | 2311911 C2 | 12/2007 |
| TW | I589298 B | 7/2017 |
| WO | WO-9303709 A1 | 3/1993 |
| WO | WO-9303764 A1 | 3/1993 |
| WO | WO-9322338 A1 | 11/1993 |
| WO | WO-9504542 A1 | 2/1995 |
| WO | WO-9527508 A1 | 10/1995 |
| WO | WO-9703703 A1 | 2/1997 |
| WO | WO-0050006 A2 | 8/2000 |
| WO | WO-0062813 A2 | 10/2000 |
| WO | WO-0077043 A2 | 12/2000 |
| WO | WO-0111067 A1 | 2/2001 |
| WO | WO-0119408 A1 | 3/2001 |
| WO | WO-0180900 A2 | 11/2001 |
| WO | WO-02069369 A2 | 9/2002 |
| WO | WO-02097116 A2 | 12/2002 |
| WO | WO-03011252 A1 | 2/2003 |
| WO | WO-03095641 A1 | 11/2003 |
| WO | WO-2004014957 A1 | 2/2004 |
| WO | WO-2006063382 A1 | 6/2006 |
| WO | 2007/022152 A2 | 2/2007 |
| WO | WO-2007121895 A2 | 11/2007 |
| WO | 2008/116078 A2 | 9/2008 |
| WO | WO-2008148057 A2 | 12/2008 |
| WO | 2009/129227 A1 | 10/2009 |
| WO | WO-2008116078 A4 | 10/2009 |
| WO | WO-2009142892 A1 | 11/2009 |
| WO | WO-2010101663 A2 | 9/2010 |
| WO | 2013/016675 A1 | 1/2013 |
| WO | 2013/188627 A2 | 12/2013 |
| WO | WO-2014047533 A1 | 3/2014 |
| WO | WO-2015061416 A2 | 4/2015 |

(56) References Cited

FOREIGN PATENT DOCUMENTS

| WO | WO-2015176662 A1 | 11/2015 |
|---|---|---|
| WO | WO-2016146618 A1 | 9/2016 |
| WO | WO-2017083820 A1 | 5/2017 |

OTHER PUBLICATIONS

Non-Final Office Action from counterpart U.S. Appl. No. 16/532,728, dated Mar. 5, 2020.
Gandhapudi et al., "Antigen Priming with Enantiospecific Cationic Lipid Nanoparticles Induces Potent Antitumor CTL Responses through Novel Induction of a Type I IFN Response", *J Immunol* 2019; 202:3524-3536; May 3, 2019; http://www.jimmunol.org/content/202/12/3524.
International Preliminary Report on Patentability from coutnerpart International Application No. PCT/US2016/061829 dated May 24, 2018.
Extended European Search Report and European Search Opinion from counterpart European Patent Appln. No. EP16865201.4 dated Jun. 6, 2019.
Notice of Reasons for Refusal received in conesponding Japanese Patent Appln. No. 2018-524752 dated Sep. 8, 2020, and its English translation.
Decision of Rejection from corresponding Japanese Patent Appln. No. 2018-524752 dated Jul. 13, 2021, and its English translation.
Notice of Defects from corresponding Israeli Patent Appln. No. 259297 dated May 5, 2021, and its English translation.
"3,5,9-Trioxa-4-phosphaheptacos-18-en-1-aminium, 4-ethoxy-N, N, N-trimethyl-10-oxo-7-[[(9Z)-1-oxo-9-octadecen-1-yl]oxy]-, 4-oxide, (7R,18Z)-," Registry, Chemical Abstracts Service, Columbus, Ohio, US, Database Accession No. 183283-20-7, Nov. 22, 1996, 02 pages, XP002694550.
Alving C.R., "Design And Selection Of Vaccine Adjuvants: Animal Models And Human Trials," Vaccine, Elsevier Science Ltd, 2002, vol. 20, pp. S56-S64.
Anderson P., "Effective Vaccination of Mice Against Mycobacterium Tuberculosis Infection With A Soluble Mixture of Secreted Mycobacterial Proteins," Infection and Immunity, American Society for Microbiology, Jun. 1994, vol. 62, No. 6, pp. 2536-2544.
Aramaki Y., et al., "Induction of Apoptosis in WEHI 231 Cells by Cationic Liposomes," Pharmaceutical Research, Plenum Publishing Corporation, Jan. 18, 2000, vol. 17, No. 5, pp. 515-520.
Baecher-Allan C., et al., "Immune Regulation In Tumor-Bearing Hosts," Current Opinion In Immunology, Elsevier Limited, 2006, vol. 18, pp. 214-219.
Baecher-Allan C., et al., "Suppressor T Cells in Human Diseases," Journal of Experimental Medicine, The Rockefeller University Press, Aug. 2, 2004, vol. 200, No. 3, pp. 273-276.
Banchereau J., et al., "Dendritic Cells And The Control of Immunity," Nature, Mar. 19, 1998, vol. 392, No. 6673, pp. 245-252.
Bei R., et al., "The Use of a Cationic Liposome Formulation (DOTAP) Mixed with a Recombinant Tumor-Associated Antigen to Induce Immune Responses and Protective Immunity in Mice," Journal of Immunotherapy, 1998, vol. 21, No. 3, 2 Pages, Abstract only.
Bei R., et al., "The Use of a Cationic Liposome Formulation (DOTAP) Mixed With a Recombinant Tumor-associated Antigen to Induce Immune Responses and Protective Immunity in Mice," Journal Of Immunotherapy, Lippincott Williams & Wilkins, Hagerstown, MD, US, Jan. 1, 1998, vol. 21, No. 3, pp. 159-169, ISSN 1524-9557, XP002963675.
Benmohamed L., et al., Lipopetide Immunization Without Adjuvant Induces Potent And Long-Lasting B, T Helper, And Cytotoxic T Lymphocyte Resonses Against A Malaria Liver Stage Antigen In Mice And Chimpanzees, European Journal Of Immunology, VCH Verlagsgesellschaft, 1997, vol. 27, pp. 1242-1253.
Berraondo P., et al., "Eradication of Large Tumors in Mice by a Tritherapy Targeting the Innate, Adaptive, and Regulatory Components of the Immune System," Cancer Research, American Association for Cancer Research, US, Sep. 15, 2007, vol. 67, No. 18, pp. 8847-8855, DOI:10.1158/0008-5472.CAN-07-0321, SSN 0008-5472, XP002673813.
Black M., et al., "Advances In The Design And Delivery Of Peptide Subunit Vaccines With A Focus On Toll-like Receptor Agonists." Expert Rev. Vaccines, vol. 9, No. 2, 2010, pp. 157-173.
Brunel F., et al., "Cationic Lipid DC-Chol Induces an Improved and Balanced Immunity Able to Overcome the Unresponsiveness to the Hepatitis B Vaccine," Vaccine, Apr. 1999, vol. 17, pp. 2192-2203.
Brunette E., et al., "Lipofection Does Not Require the Removal of Serum," Nucleic Acids Research, Cancer Research Institute, University Of California San Francisco Medical Center, San Francisco, California, Dec. 26, 1991, vol. 20, No. 5, p. 1151.
Byers A.M., et al., "Cutting Edge: Rapid In Vivo CTL Activity by Polyoma Virus-Specific Effector and Memory CD8+ T Cells," The American Association of Immunologists Inc., The Journal of Immunology, 2003, vol. 171, pp. 17-21.
Cantor H., et al., "Immunoregulatory Circuits Among T-Cell Sets II. Physiologic Role of Feedback Inhibition in Vivo: Absence in NZB Mice," The Rockefeller University Press, Journal of Experimental Medicine, 1978, pp. 1116-1125.
Carr M.W., et al., "Monocyte Chemoattractant Protein 1 Acts As AT-Lymphocyte Chemoattractant," Proceedings Of The National Academy Of Sciences of The United States Of America, Committee On Immunology and Department Of Pathology, Harvard Medical School, Department Of Cardiology, Childen's Hospital, and The Center For Blood Research, Boston, Massachusetts, Apr. 1994, vol. 91, pp. 3652-3656.
Castellino F., et al., "Chemokine-Guided CD4+ T Cell Help Enhances Generation Of IL-6Ra high IL-7Ra high Prememory CD8+ T Cells," The Journal Of Immunology, Lymphocyte Biology Section, Laboratory Of Immunology, National Institute Of Allergy And Infectious Diseases, National Institutes Of Health, Bethesda, Maryland, 2007, vol. 178, pp. 778-787.
Castellino F., et al., "Chemokines Enhance Immunity By Guiding Naive CD8+ T Cells To Sites Of CD4+ T Cell-Dendritic Cell Interaction," Nature, Lymphocyte Biology Section, Laboratory Of Immunology, National Institute Of Allergy And Infectious Diseases, National Institutes Of Health, Bethesda, Maryland, Apr. 13, 2006, vol. 440, pp. 890-895.
Chen W., et al., "A Simple and Effective Cancer Vaccine Consisting of an Antigen and a Cationic Lipid," Division of Molecular Pharmaceutics, School of Pharmacy, University of North Carolina, Chapel Hill, North Carolina, USA, 2008, pp. 1-48.
Chen W., et al., "A Simple But Effective Cancer Vaccine Consisting Of An Antigen And A Cationic Lipid," Cancer Immunology, Immunotherapy, Springer, Berlin, DE, Aug. 28, 2007, vol. 57, No. 4, pp. 517-530, ISSN 1432-0851, XP019586704.
Chen W., et al., "Induction of Cytotoxic T-Lymphocytes and Antitumor Activity by a Liposomal Lipopeptide Vaccine," Molecular Pharmaceutics, 2008, vol. 5, No. 3, pp. 464-471.
Chen W.C., et al., "Cationic Liposome-Based Peptide Vaccine: Potent Therapeutics for Cervical Cancer," Poster, School of Pharmacy, May 20, 2006, 1 Page.
Chikh G., et al., "Liposomal Delivery of CTL Epitopes to Dendritic Cells, Bioscience Reports," Plenum Publishing Corporation, Apr. 2002, vol. 22, No. 2, pp. 339-353.
Cohen P.A., et al., "CD4+ T-Cells From Mice Immunized To Syngeneic Sarcomas Recognize Distinct, Non-Shared Tumor Antigens," Cancer Research, Branches Of Surgery And Dermatology, National Cancer Institute, National Institute Of Health, Bethesda, Maryland, Feb. 15, 1994, vol. 54, pp. 1055-1058.
Comes A., et al., "CD25+ Regulatory T Cell Depletion Augments Immunotherapy of MicroMetastases by an IL-21-Secreting Cellular Vaccine1," The Journal of Immunology, The American Association of Immunologists Incorporated, 2006, pp. 1750-1758.
Communication about Intention to Grant a European Patent received for European Application No. 08799629.4, dated Jun. 1, 2015, 6 Pages.
Communication about Intention to Grant a European Patent Received for European Application No. 09733034.4, dated Jul. 6, 2018, 6 Pages.

(56) References Cited

OTHER PUBLICATIONS

Communication about Intention to Grant a European Patent Received for European Application No. 12831495.2, dated Feb. 16, 2018, 10 Pages.

Communication about Intention to Grant a European Patent Received for European Application No. 13804165.2, dated May 9, 2019, 7 Pages.

Connor J., et al., "pH-Sensitive Immunoliposomes as an Efficient and Target-Specific Carrier for Antitumor Drugs," Cancer Research, Department of Biochemistry, University of Tennessee, KnoxvilleTennessee, Jul. 1986, vol. 46, pp. 3431-3435.

Copland M.J., et al., "Lipid Based Particulate Formulations for the Delivery of Antigen," Immunology and Cell Biology, Australasian Society for Immunology Incorporated, 2005, vol. 83, pp. 97-105. Credo Reference, 2005.

Cui Z., et al., "Coating of Mannan on LPD Particles Containing HPV E7 Peptide Significantly Enhances Immunity Against HPV-Positive Tumor," Pharmaceutical Research, Jun. 2004, vol. 21, No. 6, pp. 1018-1025.

Cui Z., et al., "Immunostimulation Mechanism of LPD Nanoparticle as a Vaccine Carrier," Molecular Pharmaceutics, American Chemical Society, 2005, vol. 2, No. 1, pp. 22-28.

Cui Z., et al., "Liposome-Polycation-DNA (LPD) Particle As A Carrier and Adjuvant for Protein-Based Vaccines: Therapeutic Effect Against Cervical Cancer," Cancer Immunology and Immunother, Springer-Verlag, 2005, vol. 54, pp. 1180-1190.

Datta G., et al., "Effects of Increasing Hydrophobicity on the Physical-Chemical and Biological Properties of a Class A Amphipathic Helical Peptide," Journal of Lioid Research, 2001, vol. 42, pp. 1096-1104.

Davies G., "Adjuvant Activity of Cytokines," Chapter 19, Methods in Molecular Biology, 2010, ISSN: 0003658713, pp. 287-309.

De Bruijn M.L.H., et al., "Immunization With Human Papillomavirus Type 16 (Hpv16) Oncoproteinoloaded Dendritic Cells As Well As Proteinin Adjuvant Induces Mhc Class 1-restricted Protection To Hpv16-induced Tumor Cells," Cancer Research, Feb. 15, 1998, vol. 58, No. 4, pp. 724-731.

Decision on the Request for Reexamination from Corresponding Chinese Application No. 200880017151.0, dated Jun. 12, 2017, 18 pages.

Decision to Grant a European Patent received for European Application No. 08799629.4, dated Oct. 15, 2015, 3 Pages.

Decision to Grant a European Patent received for European Application No. 09733034.4, dated Oct. 25, 2018, 2 Pages.

Decision to Grant a European Patent Received for European Application No. 12831495.2, dated Jun. 7, 2018, 2 Pages.

Decision to Grant a European Patent received for European Application No. 13804165.2, dated Sep. 19, 2019, 3 Pages.

Decker T., et al., "The Yin and Yang of Type I Interferon Activity in Bacterial Infection," Nature Reviews Immunology, 2005, vol. 5, pp. 675-687.

Denning D.W., et al., "Micafungin (FK463), Alone or in Combination with Other Systemic Antifungal Agents, for the Treatment of Acute Invasive Aspergillosis," Journal Of Infection, Elsevier Ltd, 2006, vol. 53, pp. 337-349.

Desilva D.R, et al., "The p38 Mitogen-Activated Protein Kinase Pathway in Activated and Anergic Th1 Cells," Cellular Immunology, Academic Press, 1997, vol. 180, pp. 116-123.

Diamond D.J., et al., "Development of a Candidate HLA A*0201 Restricted Peptide-Based Vaccine Against Human Cytomegalovirus Infection," Blood, Sep. 1, 1997, vol. 90, No. 05, pp. 1751-1767.

Dileo J., et al., "Lipid-Protamine-DNA-Mediated Antigen Delivery to Antigen-Presenting Cells Results in Enhanced Anti-Tumor Immune Responses," The American Society of Gene Therapy, Molecular Therapy, May 2003, vol. 7, No. 5, pp. 640-648.

Dillon S., et al., "A Toll-Like Receptor 2 Ligand Stimulates Th2 Responses In Vivo, Via Induction Of Extracellular Signal-Regulated Kinase Mitogen-Activated Protein Kinase and c-Fos In Dendritic Cells," The Journal Of Immunology, The American Association Of Immunologists, Inc., 2004, vol. 172, 12 Pages.

Dolcetti L., et al., "Hierarchy of Immunosuppressive Strength Among Myeloid-derived Suppressor Cell Subsets is determined by GM-CSF," European Journal of Immunology, 2010, vol. 40, pp. 22-35.

Dong C., et al., "MAP Kinases in the Immune Response," Annual Review of Immunology, Annual Reviews, 2002, vol. 20, pp. 55-72.

Dow S.W., et al., "Lipid-DNA Complexes Induce Potent Activation of Innate Immune Responses and Antitumor Activity When Administered Intravenously," The Journal of Immunology, 1999, vol. 163, pp. 1552-1561.

Dranoff G., "GM-CSF-Based Cancer vaccines," Immunological Reviews, 2002, vol. 188, pp. 147-154.

Dupuis M., et al., "Dendritic Cells Internalize Vaccine Adjuvant After Intramuscular Injection," Cellular Immunology, Academic Press, 1998, vol. 186, pp. 18-27.

Eardley D.D., et al., "Immunoregulatory Circuits Among T-Cell Sets I. T-Helper Cells Induce Other T-Cell Sets to Exert Feedback Inhibition," The Rockefeller University Press, Journal of Experimental Medicine, 1978, pp. 1106-1115.

EMBL Database Entry GG774706, *Bacteroides* sp. 1_ 1_ 14 Genomic Scaffold Supercont1.5, Jun. 15, 2010, 202 Pages, [Retrieved on Oct. 28, 2013), Retrieved from the Internet: http://www.ebi.ac.uk/ena/data/view/GG774706&display=text.

English Translation of Chinese First Office Action of Corresponding Chinese Application No. 201380060902.8, dated May 26, 2016, 12 Pages.

English Translation of First Office Action from Corresponding Chinese Application No. 201710819740.1, dated Jul. 17, 2020, 21 Pages.

English Translation of First Office Action in Counterpart Chinese Application No. 201880088575.X, dated Dec. 29, 2021, 21 Pages.

English Translation of Fist Office Action from Corresponding Chinese Patent Application No. 201710819740.1, dated Apr. 29, 2021, 15 Pages.

English translation of Notification of Reasons for Rejection from Corresponding Japanese Application No. 2014-17712, dated Sep. 15, 2015, 11 Pages.

English Translation of Office Action from Corresponding Taiwan Application No. 102134251, dated Apr. 24, 2017, 13 Pages.

English Translation of Office Action in Taiwanese Application No. 101133392, dated Nov. 2, 2015, 16 pages.

English Translation of Office Action Japanese Application No. JP2014529976, dated Jul. 11, 2017, 07 pages.

English Translation of Taiwanese Office Action for Corresponding Taiwanese Application No. 102121266, dated Jun. 20, 2016, 8 Pages.

English Translation of Third Chinese Office Action from Corresponding Chinese Application No. 201380060902.8, dated Oct. 18, 2017, 27 Pages.

English Translation of Third Office Action from Corresponding Chinese Application No. 200980121761.X, dated May 9, 2016, 10 Pages.

European Communication Corresponding European Application No. EP12831495.2 dated Jun. 6, 2016, 5 pages.

European Patent Application No. 22151932.5 Search Report dated Oct. 26, 2022.

European Search Report and Written Opinion prepared for EP12831495 completed on Mar. 5, 2015, 8 Pages.

Examination Report No. 1 for Corresponding Australian Application No. 2013317805, dated Jul. 11, 2017, 4 Pages.

Examination Report No. 2 from Corresponding Australian Patent Application No. 2017340407, dated Jan. 6, 2021, 5 Pages.

Extended European Search Report for European Application No. 13804165.2, dated Jan. 5, 2016, 5 Pages.

Extended European Search Report for European Application No. 13839199.0, dated Apr. 4, 2016, 7 Pages.

Extended European Search Report for European Application No. 17859111.1, dated May 26, 2020, 7 Pages.

Extended European Search Report for European Application No. 18886648.7, dated Aug. 11, 2021, 9 Pages.

Extended European Search Report for European Application No. 19203293.6, dated Mar. 10, 2020, 6 Pages.

(56) References Cited

OTHER PUBLICATIONS

Extended European Search Report for European Application No. 08799629.4, dated Mar. 5, 2010, 04 Pages.
Extended European Search Report for European Application No. 09733034.4, dated Apr. 15, 2013, 07 Pages.
Extended European Search Report for European Application No. 12831495.2, dated Mar. 16, 2015, 09 Pages.
Felnerova D., et al., "Liposomes and Virosomes as Delivery Systems for Antigens," Nucleic Acids and Drugs, Current Opinion in Biotechnology, Elsevier Ltd, 2004, vol. 15, pp. 518-529.
Feltkamp M.C., et al., "Vaccination with Cytotoxic T Lymphocyte Epitope-containing Peptide Protects Against a Tumor Induced by Human Papillomavirus Type 16-transformed Cells," European Journal Of Immunology, PubMed, Sep. 1993, vol. 23, No. 9, pp. 2242-2249.
Fernandes I., et al., "Synthetic Lipopeptides Incorporated In Liposomes: In Vitro Stimulation OfThe Profliferation Of Murine Splenocytes And In Vivo Induction Of An Immune Response Against A Peptide Antigen," Molecular Immunology, Elsevier Limited, 1997, vol. 34, No. 8/9, pp. 569-576.
Filion M.C., et al., "Anti-Inflammatory Activity of Cationic Lipids," British Journal Of Pharmacology, Oct. 1997, vol. 122, No. 3, pp. 551-557, ISSN 0007-1188, XP002569679.
Filion M.C., "Major Limitations in the Use of Cationic Liposomes for DNA Delivery," International Journal of Pharmaceutics, 1998, vol. 162, No. 1-2, pp. 159-170.
Final Office Action from Corresponding U.S. Appl. No. 15/775,680, dated Jan. 22, 2021, 9 Pages.
First Examination Report from Corresponding Indian Patent Application No. 201618020440, dated Nov. 10, 2020, 4 Pages.
First Examination Report from counterpart Indian Application No. 11144/DELNP/2014 dated Mar. 7, 2019, 6 pages.
First Office Action from Corresponding Chinese Patent Application No. 201811312211.3, dated Aug. 3, 2021, 27 Pages.
Fuertes M.B., et al., "Host Type I IFN Signals are Required for Antitumor CD8+ T Cell Responses Through CD8α+ Dendritic Cells," Journal of Experimental Medicine, 2011, vol. 208, pp. 2005-2016.
Gabrilovich D.I., et al., "Myeloid-Derived-Suppressor Cells as Regulators of the Immune System," Nat. Rev. Immunol, Mar. 2009, vol. 9, No. 3, pp. 162-174.
Gahery-Segard H., et al., "Multiepitopic B-And T-Cell Responses Induced in Humans by a Human Immunodeficiency Virus Type 1 Lipopeptide Vaccine," American Society For Microbiology, Journal Of Virology, Feb. 2000, vol. 74, No. 4, pp. 1694-1703.
Glick D., "Methods of Biochemical Analysis," Cancer Biology Research Laboratory, Stanford University Medical Center, Stanford, California, 1988, vol. 33, pp. 337-462.
Gluck R., et al., "Biophysical Validation of Epaxal Berna, a Hepatitis A Vaccine Adjuvanted with Immunopotentiating Reconstituted Influenza Virosomes (IRIV),"Developments in Biologicals, 2000, vol. 103, 12 Pages.
Gold J.S., et al. "A Single Heteroclitic Epitope Determines Cancer Immunity After Xenogeneic Dna Immunization Against A Tumor Differentiation Antigen," The Journal of Immunology, 2003, 170. 10, pp. 5188-5194.
Grabowska et al., "Identification of Promiscuous Hpv16-Derived T Helper Cell Epitopes for Therapeutic Hpv Vaccine Design," International Journal of Cancer, 2015, vol. 136, No. 1, pp. 212-224, XP055497833.
Greenfield I., et al., "Human Papillomavirus 16 E7 Protein is Associated with the Nuclear Matrix," Proceedings of the National Academy of Sciences of the United States of America, Dec. 1991, vol. 88, pp. 11217-11221.
Gregoriadis G., et al., "Vaccine Entrapment in Liposomes," Methods, 1999, vol. 19, pp. 156-162.
Gregoriadis G., "Immunological Adjuvants: A Role for Liposomes," Immunology Today, The School of Pharmacy, University of London, 1990, vol. 11, No. 3, pp. 89-97.

Hamley I.W., "Self-Assembly of Amphiphilic Peptides," Soft Matter, 2011, vol. 7, pp. 4122-4138.
Hartikka J., et al., "Vaxfectin (Registered), A Cationic Lipid-based Adjuvant For Protein-based Influenza Vaccines," 2009, Vaccine, vol. 27, pp. 6399-6403.
Hasegawa A., et al., "Nasal Immunization With Diphtheria Toxoid Conjugated-CD52 Core Peptide Induced Specific Antibody Production In Genital Tract Of Female Mice," American Journal Of Reproductive Immunology, 2002, vol. 48, pp. 305-311.
Hassan C., et al., "Naturally Processed Non-Canonical HLA-A*02:01 Presented Peptides," The Journal of Biological Chemistry, 2015, vol. 290, No. 5, pp. 2593-2603, XP055497822.
Helmby H., et al., "Interleukin-1 Plays A Major Role In The Development OfTh2-Mediated Immunity," European Journal Of Immunology, WHILEY-VCH Verlag GmbH & Co., 2004, vol. 34, pp. 3674-3681.
Holten-Anderson L., et al., "Combination of the Cationic Surfactant Dimethyl Dioctadecyl Ammonium Bromide and Synthetic Mycobacterial Cord Factor as an Efficient Adjuvant for Tuberculosis Subunit Vaccines," Infection and Immunity, Mar. 2004, vol. 72, No. 3, pp. 1608-1617.
Hultner L., "In Activated Mast Cells, IL-1 Up-Regulates The Production Of Several Th2-Related Cytokines Including IL-9," The American Association Of Immunologists, The Journal Of Immunology, 2000, vol. 164, pp. 5556-5563.
Immordino et al., "Stealth Liposomes: Review of the Basic Science, Rationale, and Clinical Applications, Existing and Potential," International Journal of Nanomedicine, 2006, vol. 1, No. 03, pp. 297-315.
Inaba K., et al., "Generation Of Large Numbers Of Dendritic Cells From Mouse Bone Marrow Cultures Supplemented With Granulocyte/Macrophage Colony-Stimulating Factor," Journal Of Experimental Medicine, The Rockefeller University Press, Dec. 1992, vol. 176, pp. 1693-1702.
International Preliminary Report on Patentability for International Application No. PCT/US2009/040500, dated Oct. 28, 2010, 6 Pages.
International Preliminary Report on Patentability for International Application No. PCT/US2013/045578, dated Dec. 24, 2014, 7 Pages.
International Preliminary Report on Patentability for International Application No. PCT/US2013/061132, dated Apr. 2, 2015, 10 Pages.
International Preliminary Report on Patentability for International Application No. PCT/US2017/055119, dated Apr. 18, 2019, 16 Pages.
International Search Report and Written Opinion for International Application No. PCT/US2009/040500, dated Jun. 4, 2009, 7 Pages.
International Search Report and Written Opinion for International Application No. PCT/US2013/045578, dated Nov. 25, 2013, 9 Pages.
International Search Report and Written Opinion for International Application No. PCT/US2013/061132, dated Dec. 30, 2013, 12 Pages.
International Search Report and Written Opinion for International Application No. PCT/US2017/055119, dated Mar. 7, 2018, 23 Pages.
International Search Report and Written Opinion for International Application No. PCT/US2021/060337, dated Feb. 14, 2022, 7 Pages.
International Preliminary Report on Patentability for International Application No. PCT/US2008/057678, dated Sep. 22, 2009, 5 Pages.
International Preliminary Report on Patentability for International Application No. PCT/US2012/054786, dated Mar. 20, 2014, 6 Pages.
International Preliminary Report on Patentability for International Application No. PCT/US2017/055348, dated Apr. 18, 2019, 6 Pages.
International Preliminary Report on Patentability for International Application No. PCT/US2018/064060, dated Jun. 18, 2020, 7 Pages.

(56) References Cited

OTHER PUBLICATIONS

International Search Report and Written Opinion for International Application No. PCT/US2008/057678, dated Apr. 20, 2009, 6 Pages.
International Search Report and Written Opinion for International Application No. PCT/US2012/054786, dated Nov. 15, 2012, 8 Pages.
International Search Report and Written Opinion for International Application No. PCT/US2017/055348, dated Jan. 5, 2018, 8 Pages.
International Search Report and Written Opinion for International Application No. PCT/US2018/064060, dated Apr. 30, 2019, 9 Pages.
International Search Report for International Application No. PCT/US2008/057678, dated Apr. 20, 2009, 3 Pages.
International Search Report for International Application No. PCT/US2009/040500, dated Jun. 4, 2009, 2 Pages.
Ishida T., et al., "Defective Function Of Langerhans Cells In Tumor-Bearing Animals is the Result of Defective Maturation from Hemopoietic Progenitors," The American Association Of Immunologists, The Journal Of Immunology, 1998, vol. 161, pp. 4842-4851.
Iwaoka S., et al., "Cationic Liposomes Induce Apoptosis Through p38 MAP-kinase-caspase-8-Bid Pathway in Macrophage-like RAW 264.7 Cells", Journal of Leukocyte Biology, Jan. 2006, vol. 79, pp. 184-191, XP008117765.
Jacob A., et al., "Convergence of Signaling Pathways on the Activation of ERK in B Cells," The Journal of Biological Chemistry, The American Society for Biochemistry and Molecular Biology Incorporated, Jun. 28, 2002, vol. 277, No. 26, pp. 23420-23426.
Jiao X., et al., "Modulation of Cellular Immune Response Against Hepatitis C Virus Nonstructural Protein 3 by Cationic Liposome Encapsulated DNA Immunization," Hepatology, Feb. 2003, vol. 37, No. 2, pp. 452-460.
Jisho: "Kojien," Japanese Dictionary, Third Edition, Iwanami Shoten, 1983, 1 Page.
Johnson G.L., et al, "Mitogen-activated Protein Kinase Pathways Mediated by ERK, JNK, and p38 Protein Kinases," Science, Dec. 6, 2002, vol. 298, pp. 1911-1912.
Jones C.A., et al., "Vaccination Strategies to Prevent Genital Herpes and Neonatal Herpes Simplex Virus (HSV) Disease," HERPES, 2004, vol. 11, pp. 12-17.
Joseph A., et al., "A New Intranasal Influenza Vaccine Based on a Novel Polycationic Lipid-Ceramide Carbamoyl-Spermine (CCS) I. Immunogenicity and Efficacy Studies in Mice," Vaccine, 2006, vol. 24, pp. 3990-4006.
Kabarowski J.H.S., et al, "Lysophospatidylcholine As A Ligand For The Immunoregulatory Receptor G2A," Science, Department Of Microbiology, Immunology, And Molecular Genetics, Department Of Cancer Biology, Lerner Research Institute, Cleveland, Ohio, Jul. 27, 2001, vol. 293, pp. 702-705.
Kahn J.O., et al., "Clinical and Immunologic Responses to Human Immunodeficiency Virus (HIV) Type 1SF2 GP120 Subunit Vaccine Combined with MF59 Adjuvant with or without Muramyl Tripeptide Dipalmitoyl Phosphatidylethanolamine in Non-HIV-Infected Human Volunteers," The Journal of Infectious Diseases, 1994, vol. 170, pp. 1288-1291.
Kanafani Z.A., et al., "Daptomycin: A Rapidly Bactericidal Lipopeptide for the Treatment of Gram-Positive Infections," Experimental Review of Antibacterial Infections, Future Drugs Ltd, 2007, vol. 5, No. 2, pp. 177-184.
Kantengwa S., et al., "Superoxide Anions Induce The Maturation of Human Dendritic Cells," American Journal of Respiratory and Critical Care Medicine, Divisions of Pneumology and Thoracic Surgery, University Hospital, Geneva, Switzerland, Feb. 1, 2003, vol. 167, No. 3, pp. 431-437.
Kenter G.G., et al., "Vaccination Against Hpv-16 Oncoproteins for Vulvar Intraepithelial Neoplasia," The New England Journal of Medicine, Nov. 5, 2009, vol. 361, pp. 1838-1847.
Kim J.J., et al., "CD8 Positive T Cells Influence Antigen-Specific Immune Responses through the expression of Chemokines," Journal Of Clinical Investigation, The American Society For Clinical Investigation, Inc., Sep. 1998, vol. 102, No. 6, pp. 1112-1124.
Kogkopoulou O., et al., "Conditional Up-Regulation of IL-2 Production By p38 MAPK Inactivation Is Mediated By Increased ERKI/2 Activity," Journal of Leukocyte Biology, May 2006, vol. 79, pp. 1052-1060.
Kokkoli E., et al., "Self-assembly and Applications of Biomimetic and Bioactive Peptide-amphiphiles," Soft Matter, 2006, vol. 2, pp. 1015-1024.
Korsholm , "Unravelling the Adjuvant Mechanism of Cationic Liposomes," Statens Serum Institute, Jun. 2006, pp. 15.00-15.30.
Korsholm K.S., et al., "The Adjuvant Mechanism of Dimethyldioctadecyl-ammonium Liposomes," Immunology, Jun. 2007, vol. 121, No. 2, pp. 216-226.
Kranz L.M., et al., "Systemic RNA Delivery to Dendritic Cells Exploits Antiviral Defence for Cancer Immunotherapy," Nature, Jun. 16, 2016, vol. 534, 16 Pages, DOI:10.1038/nature18300, XP055565453.
Li S., et al., "Targeted Delivery of Antisense Oligodeoxynucleotide and Small Interference RNA Into Lung Cancer Cells," Molecular Pharmaceutics, American Chemical Society, 2006, vol. 3, No. 5, pp. 579-588.
Liang M.T., et al., "Encapsulation of Lipopeptides Within Liposomes: Effect of Number of Lipid Chains, Chain Length and Method of Liposome Preparation," International Journal of Pharmaceutics, Elsevier B.V., 2005, vol. 301, pp. 247-254.
Lodoen M.B., et al., "Natural Killer Cells as an Initial Defense Against Pathogens," Current Opinion in Immunology, Elsevier Ltd, 2006, vol. 18, pp. 391-398.
Lonez C., et al., "Cationic Liposomal Lipids: From Gene Carriers to Cell Signaling," Progress in Lipid Research, 2008, vol. 47, pp. 340-347.
Lucas W., et al., "Viral Capsids and Envelopes: Structure and Function," Encyclopedia of Life Sciences (ELS), John Wiley & Sons, 2010, pp. 1-7.
MacKay C.R., "Chemokines: Immunology's High Impact Factors," Nature Immunology, Feb. 2001, vol. 2, No. 2, pp. 95-101.
Mansour M., et al., "Therapy Of Established B16-f10 Melanoma Tumors By A Single Vaccination Of Ctl/t Helper Peptides In Vaccimax," Journal of Translational Medicine, 2007, vol. 5, No. 20, 8 Pages.
Melief C.J.M., et al., "Effective Therapeutic Anticancer Vaccines Based on Precision Guiding of Cytolytic T Lymphocytes," Blackwell Munksgaard, Immunological Reviews, 2002, vol. 188, pp. 177-182.
Minutello M., et al., "Safety And Immunogenicity Of An Inactivated Subunit Influenza Virus Vaccine Combined With MF59 Adjuvant Emulsion In Elderly Subjects," Immunized For Three Consecutive Influenza Seasons, Vaccine, Elsevier Science Limited, 1999, vol. 17, pp. 99-104.
Moingeon P., et al., "Towards the Rational Design of Th1 Adjuvants," Vaccine, Elsevier Science Limited, 2001, vol. 19, pp. 4363-4372.
Non Final Office Action dated Apr. 29, 2022 for U.S. Appl. No. 14/531,469, 12 Pages.
Non-Final Office Action from Counterpart U.S. Appl. No. 15/775,680, dated Apr. 1, 2020, 14 Pages.
Notification of Reason of Rejection of Japanese Application No. JP2017218514, dated Aug. 21, 2018, 13 pages.
Office Action for Canadian Application No. 2885741, dated May 10, 2022, 03 pages.
Office Action for Corresponding Russian Application No. 2015101110, with its English translation, dated Aug. 8, 2017, 06 pages.
Office Action for Corresponding Russian Application No. 2015101110, with its English translation, dated Mar. 28, 2017, 10 pages.
Office Action for European Application No. 08799629.4, dated Aug. 7, 2012, 4 Pages.
Office Action for European Application No. 08799629.4, dated Jan. 10, 2014, 3 Pages.
Office Action for European Application No. 08799629.4, dated May 17, 2010, 1 Page.
Office Action for European Application No. 08799629.4, dated Apr. 26, 2011, 3 Pages.

(56) References Cited

OTHER PUBLICATIONS

Office Action for European Application No. 09733034.4, dated Apr. 16, 2015, 5 Pages.
Office Action for European Application No. 09733034.4, dated Nov. 18, 2016, 4 Pages.
Office Action for European Application No. 12831495.2, dated Dec. 1, 2016, 4 Pages.
Office Action for European Application No. 12831495.2, dated Jun. 6, 2016, 5 Pages.
Office Action for European Application No. 12831495.2, dated May 11, 2017, 4 Pages.
Office Action for European Application No. 13804165.2, dated Mar. 2, 2018, 3 Pages.
Office Action for European Application No. 13804165.2, dated Jul. 5, 2017, 4 Pages.
Office Action for European Application No. 13804165.2, dated May 17, 2018, 3 Pages.
Office Action for European Application No. 13804165.2, dated Sep. 22, 2016, 3 Pages.
Office Action for European Application No. 13804165.2, dated Aug. 23, 2018, 3 Pages.
Office Action for European Application No. 13839199.0, dated Nov. 13, 2017, 4 Pages.
Office Action for European Application No. 13839199.0, dated Nov. 21, 2016, 4 Pages.
Office Action for European Application No. 13839199.0, dated Jul. 30, 2018, 4 Pages.
Office Action for European Application No. 16865201.4, dated Jul. 16, 2020, 5 Pages.
Office Action for European Application No. 19203293.6, dated Feb. 19, 2021, 4 Pages.
Office Action for European Application No. 19203293.6, dated Dec. 22, 2021, 4 Pages.
Office Action for Taiwanese Application No. TW101133392, with English Translation, dated Jul. 17, 2017, 05 pages.
Office Action from Corresponding Indian Application No. 7544/DELNP/2010, dated Jun. 22, 2017, 10 Pages.
Office Action from Counterpart Brazilian Patent Application. No. PI0910464-0, dated Nov. 6, 2018, and a Brief Summary in English, 5 pages.
Office Action from Counterpart Taiwanese Patent Application. No. 106109798 with English translation, dated Nov. 14, 2017, 09 pages.
Office Action of European Application No. 12831495.2, dated Dec. 17, 2015, 5 pages.
Office Action of Taiwanese Application No. 101133392, dated May 16, 2016, along with an English translation of the Search Report, 8 pages.
Okada N., et al., "Effects of Lipofectin-Antigen Complexes on Major Histocompatibility Complex Class I-Restricted Antigen Presentation Pathway in Murine Dendritic Cells and on Dendritic Cell Maturation," Biochimica et Biophysica Acta, Elsevier Science, 2001, vol. 1527, pp. 97-101.
Oliveira L.M.F.D., et al., "Design of Immune Responses and Anti-Tumor Potential of an HPV16 E6E7 Multi-Epitope Vaccine," PLoS ONE, 2015, vol. 10, No. 9: e0138686, 13 Pages.
Padron-Regalado E., "Vaccine for SARS-CoV-2: Lessons from Other Coronavirus Strains," Infectious Diseases and Therapeutics, 2020, vol. 9, pp. 255-274.
Perales M., et al., "Phase I/II Study of GM-CSF DNA as an Adjuvant for a Multipeptide Cancer Vaccine in Patients with Advanced Melanoma," Molecular Therapy, Dec. 2008, vol. 16, No. 12, pp. 2022-2029.
Pialoux G.D., et al., "Lipopeptides Induce Cell-Mediated Anti-HIV Immune Responses In Seronegative Volunteers," Lippincott Williams & Wilkins, Inc., Official Journal Of The International Of AIDS, Jul. 6, 2001, vol. 15, No. 10, pp. 1239-1249.
Pierre Y., et al., "Liposome-Mediated DNA Immunisation via the Subcutaneous Route," Journal of Drug Targeting, Taylor & Francis Ltd, 2003, vol. 11, No. 8-10, pp. 555-563.

Radu C.G., et al., "T Cell Chemotaxis to Lysophosphatidylcholine through the G2A Receptor," Proceedings of the National Academy of Sciences, The National Academy of Sciences of The USA, Jan. 6, 2004, vol. 101, No. 1, pp. 245-250.
Rao P.E., et al., "Differentiation and Expansion of T Cells with Regulatory Function from Human Peripheral Lymphocytes by Stimulation in the Presence of TGF-B," The Journal of Immunology, The American Association of Immunologists, Inc., 2005, vol. 174, pp. 1446-1455.
Restriction Requirement from Counterpart dated Jan. 7, 2020 for U.S. Appl. No. 15/775,680, 09 Pages.
Riemer A.B., et al., "A Conserved E7-Derived Cytotoxic T Lymphocyte Epitope Expressed On Human Papillomavirus-16 Transformed HLA-A2+ Human Epithelial Cancers," The Journal Of Biological Chemistry, Sep. 17, 2010, vol. 285, No. 38, pp. 29608-29622, XP055207597.
Robinson J.H., et al., "Palmitic Acid Conjugation of a Protein Antigen Enhances Major Histocompatibility Complex Class II-Restricted Presentation to T Cells," Immunology, 1992, vol. 76, pp. 593-598.
Rock K.L., et al., "Natural Endogenous Adjuvants," Spriner Semin Immunology, 26, 2005, pp. 231-246.
Ross T.M., "A Trivalent Virus-like Particle Vaccine Elicits Protective Immune Responses against Seasonal Influenza Strains in Mice and Ferrets," PloS one, e6032, Jun. 24, 2009, vol. 4, No. 6, pp. 1-11.
Rughetti A., et al., "Transfected Human Dendritic Cells to Induce Antitumor Immunity," Gene Therapy, Sep. 2000, vol. 7. No. 17, pp. 1458-1466.
Santin A.D., et al., "Induction of Human Papillomavirus-Specific CD4 + and CD8+ Lymphocytes by E7-Pulsed Autologous Dendritic Cells in Patients with Human Papillomavirus Type 16- and 18-Positive Cervical Cancer," Journal of Virology, Jul. 1999, vol. 73, No. 7, pp. 5402-5410.
Sato N., et al., "CC Chemokine Receptor (CCR) 2 Is Required For Langhans Cell Migration And Localization Of T Helper Cell Type 1 (Th1)-Inducing Dendritic Cells: Absence Of CCR2 Shifts The Leishmania Major-Resistant Phenotype To A Susceptible State Dominated By Th2 Cytokines, B Cell Outgrowth, And Sustained Neutrophilic Inflammation," Journal Of Experimental Medicine, The Rockefeller University Press, Jul. 17, 2000, vol. 192, No. 2, pp. 205-218.
Schroeder M.A., et al., "Pegylated Murine GM-CSF Increases Myeloid Derived Suppressor Cells In Vivo," Blood, 2011, vol. 118, No. 21, p. 2967, ISSN: 0003513278.
Second Examiner's Report and Examination Search Report from Counterpart Canadian Patent Application No. 2,885,741, dated Aug. 10, 2020, 4 Pages.
Second Office Action and Supplementary Search Report for Corresponding Chinese Application No. 201380060902.8, dated Mar. 31, 2017, 28 Pages.
Shimizu T., et al., "Antitumor Activity, Mitogenicity, and Lethal Toxicity of Chemical Synthesized Monosaccharide Analog of Lipid A," J. Pharmacobiodyn, 1988, vol. 11, No. 7, pp. 512-518.
Shinozaki Y., et al., "Tumor-specific Cytotoxic T Cell Generation And Dendritic Cell Function Are Differentially Regulated By Interleukin 27 During Development Of Anti-tumor Immunity," International Journal of Cancer, 2009, vol. 124, No. 6, pp. 1372-1378.
Sinha P., et al., "Cross-Talk Between Myeloid-Derived Suppressor Cells and Macrophages Subverts Tumor Immunity Toward a Type 2 Response," The Journal of Immunology, 2007, vol. 179, pp. 977-983.
Song Y.K., et al., "Free Liposomes Enhance the Transfection Activity of DNA/Lipid Complexes in Vivo by Intravenous Administration," Biochimica et Biophysica Acta, 1998, vol. 1372, pp. 141-150.
Sprott G.D., et al., "Activation of Dendritic Cells by Liposomes Prepared from Phosphatidylinositol Mannosides from Mycobacterium Bovis Bacillus Calmette-Guerin and Adjuvant Activity In Vivo," Infection and Immunity, Sep. 2004, vol. 72, No. 9, pp. 5235-5246.
Steller M.A., et al., "Cell-Mediated Immunological Responses in Cervical and Vaginal Cancer Patients Immunized with a Lipidated Epitope of Human Papillomavirus Type 16 E7," Clinical Cancer Research, Sep. 1998, vol. 4, pp. 2103-2109.

(56) References Cited

OTHER PUBLICATIONS

Sumida S.M., et al., "Recruitment and Expansion of Dendritic Cells In Vivo Potentiate the Immunogenicity of Plasmid DNA Vaccines," The Journal of Clinical Investigation, USA, Nov. 2004, vol. 114, No. 9, pp. 1334-1342.
Sun W.Q., et al., "Stability of Dry Liposomes in Sugar Glasses," Biophysical Journal, Apr. 1996, vol. 70, pp. 1769-1776.
Supplementary European Search Report for European Application No. 13804165.2, dated Jan. 22, 2016, 07 Pages.
Taiwan Search Report for Taiwanese Application No. 107143751, dated Jul. 27, 2022, 2 Pages, with translation.
Takaoka A., et al., "Integration of interferon—Alpha/Beta Signaling to P53 Responses in Tumor Suppression and Antiviral Defense," Nature, Jul. 31, 2003, vol. 424, pp. 516-523.
The Notice of Reasons for Rejection of Counterpart Japanese Patent Application No. 2019-518245, dated Oct. 26, 2021, Along With an English Translation, 14 Pages.
Third Examiner's Report and Examination Search Report from Counterpart Canadian Patent Application No. 2,885,741, dated Jun. 30, 2021, Along with A Request to Withdraw Report dated Aug. 25, 2021, 5 Pages.
Third Examiner's Report from Corresponding Canadian Patent Application No. 2,876,656, dated Mar. 25, 2021, 5 Pages.
Tindle R., et al., "NCBI Blast Search Teaching Sequence 43," Genback, US6183745, 2001, 1 Page.
Tobiume K., et al., "ASK1 Is Required For Sustained Activations Of JNL/p38 MAP Kinases And Apoptosis," EMBO Reports, European Molecular Biology Organization, 2001, vol. 2, No. 3, pp. 222-228.
Toledo H., et al., "A Phase I Clinical Trial of a Multi-Epitope Polypeptide TAB9 Combined with Montanide ISA720 Adjuvant in Non-HIV-1 Infected Human Volunteers," Vaccine, Elsevier Science Ltd, 2001, vol. 19, pp. 4328-4336.
Translation of Notification of Reason for Rejection from Corresponding Japanese Patent Application No. 2013-217819, dated Jan. 10, 2017, 7 Pages.
"Transplantation," Supplement 1, 2010, vol. 90, No. 2S, pp. 519-2687, 1 Page, ISSN: 0003513279.
Tsang K.Y., et al., "Identification and Characterization of Enhancer Agonist Human Cytotoxic T-cell Epitopes of The Human Papillomavirus Type 16 (Hpv16) E6/E7," Vaccine, 2017, vol. 35, pp. 2605-2611.
Uemura A., et al, "Induction Of Immune Responses Against Glycosphingolipid Antigens: Comparison Of Antibody Responses In Mice Immunized With Antigen Associated With Liposomes Prepared From Various Phospholipids," Journal Of Veterinary Medical Science, 2005, vol. 67, No. 12, pp. 1197-1201.
United States Patent and Trademark Office, Offic Action for U.S. Appl. No. 11/121,840, dated Sep. 7, 2007, 6 Pages.
United States Patent and Trademark Office, Office Action for U.S. Appl. No. 11/121,840, dated Jun. 4, 2007, 5 Pages.
Vangasseri D.P., "Immunostimulation of Dendritic Cells by Cationic Liposomes," Molecular Membrane Biology, Taylor and Francis, GB, Sep. 1, 2006, vol. 23, No. 5, pp. 385-395, DOI: 10.1080/09687860600790537, ISSN 0968-7688, XP008137311.
Varypataki E.M., et al., "Cationic Liposomes Loaded With a Synthetic Long Peptide and Poly(L:C): a Defined Adjuvanted Vaccine for Induction Of Antigen-Specific T Cell Cytotoxicity," The AAPS Journal, Jan. 2015, vol. 17, No. 1, pp. 216-226.
Vasievich E. A., et al., "Enantiospecific Adjuvant Activity of Cationic Lipid DOTAP in Cancer Vaccine", Cancer Immunology, Immunotherapy, May 2011, vol. 60, No. 5, Abstract Only, 1 Page.
Vasievich E.A., et al., "Trp2 Peptide Vaccine Adjuvanted With O-dotap Inhibits Tumor Growth In An Advanced Melanoma Model," Division of Molecular Pharmaceutics, 2012, vol. 9, pp. 261-268.
Vautier-Giongo C., et al., "Effects Of Interactions On The Formation Of Mixed Micelles Of 1.2-diheptaoyl-sn-glycero-3-phosphocholine With Sodiumdodecyl Sulfate And Dodecyltrimethylemmonuium Bromide," Journal of Colloid and Interface Science 282, 2005, pp. 149-155.

Verheul A.F.M., et al., "Monopalmitic Acid-Peptide Conjugates Induce Cytotoxic T Cell Responses Against Malarial Epitopes: Importance of Spacer Amino Acids," Journal of Immunological Methods, Elsevier Science B.V., 1995, vol. 182, pp. 219-226.
Vogel F.R., et al., "A Compendium of Vaccine Adjuvants and Excipients," Pharmaceutical biotechnology, 1995, vol. 6, 89 Pages.
Vogel F.R., "Improving Vaccine Performance With Adjuvants," Clinical Infectious Diseases, Infectious Diseases Society Of America, 2000, vol. 30, Suppl. 3, pp. S266-S270.
Walker C., et al., "Cationic Lipids Direct A Viral Glycoprotein Into The Class I Major Histocompatibility Complex Antigen-presentation Pathway," Proceedings of National Acadamy Science, USA, Sep. 1992, vol. 89, pp. 7915-7918.
Wang H., et al., "Potential Involvement Of Monocyte Chemoattractant Protein (MCP)-1/CCL2 In IL-4-Mediated Tumor Immunity Through Inducing Dendritic Cell Migration Into The Draining Lymph Nodes," International Immunopharmacology, Elsevier Science B.V, 2003, vol. 03, pp. 627-642.
Wang L., et al., "Lysophosphatidylcholine-Induced Surface Redistribution Regulates Signaling Of The Murine G Protein-Coupled Receptor G2A," Molecular Biology Of The Cell, The American Society For Cell Biology, May 2005, vol. 16, pp. 2234-2247.
Wang R-F., et al., "Enhancement of Antitumor Immunity By Prolonging Antigen Presentation on Dendritic Cells," Nature Biotechnology, Nature Publishing Group, Feb. 2002, vol. 20, pp. 149-154.
Weiss A., et al., "Intracellular Peptide Delivery Using Amphiphilic Lipid-Based Formulations," Biotechnology and Bioengineering, US, Oct. 2011, (Apr. 25, 2011), vol. 108, No. 10, pp. 2477-2487, DOI: 10.1002/bit.23182, ISSN 0006-3592, XP055250096.
Welters M.J.P., et al., "Induction of Tumor-Specific CD4+ and CD8+ T-Cell Immunity in Cervical Cancer Patients by a Human Papillomavirus Type 16 E6 and E7 Long Peptides Vaccine," Clinical Cancer Research, Jan. 1, 2008, vol. 14, No. 1, pp. 178-187.
Wenworth D.E., et al., "Hemagglutinin [Influenza A virus (A/New Caledonia/20/1999(H1N1))]," GenBank Accession # AFO65027, Jul. 26, 2012, 2 Pages.
Whitmore M., et al., "LPD Lipopolyplex Initiates A Potent Cytokine Response And Inhibits Tumor Growth," Gene Therapy, Stockton Press, 1999, vol. 6, pp. 1867-1875.
Wrapp D., et al., "Cryo-EM Structure of the 2019-nCoV Spike in the Prefusion Conformation," Science, Mar. 13, 2020, vol. 367, pp. 1260-1263.
Xiao X., et al., "HLA-A, HLA-B, HLA-DRB1 Polymorphisms and Risk of Cervical Squamous Epithelial Cell Carcinoma: A Population Study in China," Asian Pacific Journal of Cancer Prevention, 2013, vol. 14, No. 7, pp. 4427-4433, XP055497830.
Yamshchikov G.V., et al., "Evaluation Of Peptide Vaccine Immunogenicity In Draining Lymph Nodes And Peripheral Blood Of Melanoma Patients," International Journal of Immunology, Wiley-Liss, Inc., 2001, vol. 92, pp. 703-711.
Yan W., et al., "Mechanism of Adjuvant Activity of Cationic Liposome: Phosphorylation of A MAP Kinase, ERK and Induction of Chemokines," Molecular Immunology, 2007, vol. 44, pp. 3672-3681.
Yao T., et al., "Integrated Basic Chemistry for Geo Science," Naniing University Press, 2007, pp. 410-421.
Yao Y., et al., "HPV-16 E6 and E7 Protein T Cell Epitopes Prediction Analysis Based on Distributions of HLA-A Loci Across Populations: An in Silico Approach," Vaccine, 2013, vol. 31, No. 18, pp. 2289-2294, XP055497828.
Yasuda K., et al., "Endosomal Translocation of Vertebrate DNA Activates Dendritic Cells via TLR9-Dependent and Independent Pathways," The Journal of Immunology, 2005, vol. 174, pp. 6129-6136.
Yoo J.K., et al., "IL-18 Induces Monocyte Chemotactic Protein-1 Production in Macrophages Through the Phosphatidylinositol 3-Kinase/Akt and MEK/ERK1/2 Pathways," The Journal of Immunology, The American Association of Immunologists Incorporated, 2005, vol. 175, pp. 8280-8286.
Yoshimura T., et al., "Human Monocyte Chemoattractant Protein-1 (MCP-1), Full Length cDNA Cloning, Expression In Mitogen-Stimulated Blood Mononuclear Leukocytes, and Sequence Similar-

(56) References Cited

OTHER PUBLICATIONS ity To Mouse Competence Gene JE," Federation of European Biochemical Societies, Elsevier Science Publishers B.V., Feb. 1989, vol. 244, No. 2, pp. 487-493.

Yotsumoto S., et al., "Endosomal Translocation of CpG-Oligodeoxynucleotides Inhibits DNA-PKcs-Dependent IL-10 Production in Macrophages," The Journal of Immunology, 2008, vol. 180, pp. 809-816.

Yu J.J., et al., "Regulation and Phenotype of an Innate Th1 Cell: Role of Cytokines and the P38 Kinase Pathway," The Journal of Immunology, The American Association of Immunologists, 2003, vol. 171, pp. 6112-6118.

Zaks K., et al., "Efficient Immunization and Cross-Priming by Vaccine Adjuvants Containing TLR3 or TLR9 Agonists Complexed to Cationic Liposomes," The Journal of Immunology, 2006, vol. 176, pp. 7335-7345.

Zhang H., et al., "English Translation of Specification of CN111217918," European Patent Office, 2020, 85 pages.

Zhang H., et al., "Stress-Induced Inhibition of ERK1 and ERK2 by Direct Interaction With p38 MAP Kinase," The Journal of Biological Chemistry, The American Society for Biochemistry and Molecular BiologyInc, Mar. 9, 2001, vol. 276, No. 10, pp. 6905-6908.

Zhang L., et al., "Converting Peptides into Drug Leads by Lipidation," Current Medicinal Chemistry, 2012, vol. 19, No. 11, pp. 1602-1618, ISSN 0929-8673.

Zhao L-J., et al., "Interferon Alpha Regulates MAPK and STAT1 Pathways in Human Hepatoma Cells," Virology Journal, Apr. 6, 2011, vol. 8, No. 157, pp. 1-7.

Zitvogel L., et al., "Type I Interferons in Anticancer Immunity," Nature Reviews Immunology, Jul. 2015, vol. 15, pp. 405-414.

\* cited by examiner

LIPIDS AS SYNTHETIC VECTORS TO ENHANCE ANTIGEN PROCESSING AND PRESENTATION EX-VIVO IN DENDRITIC CELL THERAPY

CROSS-REFERENCE TO RELATED APPLICATIONS

This international application claims the benefit of U.S. Provisional Application Ser. No. 62/254,794 filed on Nov. 13, 2015 and U.S. Provisional Application Ser. No. 62/404,504 filed on Oct. 5, 2016, the entire disclosure of both of which are incorporated herein by reference.

FIELD OF THE INVENTION

The invention relates to dendritic cell therapies in cancer. Adoptive transfer of autologous ex vivo cultured hematopoietic progenitor cell or monocyte derived dendritic cells (DC) have been tested as cancer vaccines for over a decade. The studies suggest that DC-based vaccines are safe and can induce the expansion of circulating $CD4^+$ T cells and $CD8^+$ T cells that are specific for tumor antigens. Objective clinical responses have been observed in some patients. It is also now established that the clinical response takes time to build up, however remissions can be very long-lasting. DCs isolated from animals and loaded with tumor antigen ex vivo and administered as a cellular therapy have been demonstrated to induce both preventive and therapeutic benefit in preclinical anti-tumor studies.

Exploitation of the antigen-presenting properties of DCs has shown recent promise in the development of effective cancer immunotherapies, and multiple recent clinical trials have yielded promising results. Treatment of metastatic prostate cancer with sipuleucel-T, resulted in an approximately 4-month-prolonged median survival in Phase III trial. Sipuleucel-T (Provenge®) is a cellular product based on dendritic cells obtained from enriched blood obtained from the patient and cultured with a fusion protein of prostatic acid phosphatase (PAP) and GM-CSF. The dendritic cells are then given back to the patient by infusion into a vein (IV). This process is repeated twice more, 2 weeks apart, so that the patient gets 3 doses of cells. Sipuleucel-T has been approved by the US Food and Drug Administration (FDA) for the treatment of metastatic prostate cancer, thereby paving the clinical development and regulatory path for the next generation of cellular immunotherapy products. Some metastatic-melanoma affected individuals, who were vaccinated with activated DCs loaded with tumor-antigen peptides, showed antigen-specific $CD4^+$ and $CD8^+$ T cell responses. Despite the promise, clinical responses have been disappointing, with classic objective anti-tumor response rates rarely exceeding 15%.

BACKGROUND OF THE INVENTION

Dendritic cell therapy is a promising approach to treating various debilitating diseases including cancer. The approach allows for tailored and personalized treatments to be developed for patients. For example rather than using specific protein antigens for a particular cancer, antigens can be obtained from the patient's tumor and loaded into the patient's own dendritic cells for treatment. The ex-vivo dendritic cell therapy approach has been found to present significant promise with an already approved product which has demonstrated sustained immune responses in patients 2 years after treatment. However, the therapeutic results have been suboptimal and several approaches to improving these therapies are being investigated.

One important issue is the selection of tumor antigens for loading the DCs. Candidate antigens include unique (mutated) antigens and shared non-mutated self-antigens. To generate broadly applicable therapies, non-mutated self-antigens have been mostly preferred, even though with such approaches the population of high-avidity clones could be depleted through negative selection. Using mutated antigens might avoid these drawbacks. The development of RNA sequencing technologies is aiding in the determination of the complete range of mutated antigens from the primary and metastasized tumors, thereby allowing the ability to tailor the therapy to the specific patient.

Very often in peptide-based or protein-based antigens and with autologous tumor-derived antigens, a critical limiting factor in their successful application in DC vaccines is the amount of available antigen. One technical hurdle to overcome is the ability to effectively present these antigens to the dendritic cells to enable more effective presentation via MHC class I ($CD8^+$ T-cells) and MHC class II ($CD4^+$ T-cells). This continues to be suboptimal and directly influences the potency and robustness of the resulting T-cell response.

DCs are also capable of cross presentation of antigens. Cross presentation refers to a pathway in which exogenous soluble proteins or peptides are taken up by an antigen presenting cell, and instead of entering the proteolytic MHC class II presentation pathway, the peptide or protein enter into the MHC class I processing pathway. This can occur two ways, via the cytosolic pathway or the endosomal pathway. In both pathways, the proteins are initially taken up in endosomes/phagosomes. In the cytosolic pathway, a portion of partially degraded endosomal proteins ultimately enter the cytoplasm, via poorly understood mechanisms, where they are processed through proteasomes and the resulting peptides transported by TAP into either the endoplasmic reticulum or other endosomes for binding to MHC class I. Alternatively, proteins can be endosomally degraded and peptides can bind to MHC class I present in the endosomes. This latter pathway is proteasome independent and inefficient as it relies on the chance production of the correct peptide by endosomal proteases. Entry of proteins into early endosomes which contain limited proteolytic activity favor cross-presentation, while late endosomes which contain higher levels of proteolytic activity may inhibit cross-presentation.

From the above discussion, it is clear that proteins entering the endosomal pathway, particularly the early endosomal pathway, can be cross-presented on MHC class I. It also follows that the degree of cross presentation depends on the amount of a particular protein/peptide taken up into early endosomes, and the quantity of antigenic fragments subsequently delivered to the cytoplasm. Soluble proteins which bind to DC scavenger receptors can be cross-presented. The classic example is ovalbumin which binds to the mannose receptor. However not all proteins/peptides will bind to DC scavenger receptors which has led to various approaches of receptor targeting. These approaches include targeting the Fc receptor, various C-type lectin receptors like CD205, CD207, CLEC9a, integrins, or glycolipids. There are several drawbacks to these approaches. There is a requirement for coupling the antigen to a particular receptor binding protein, usually a monoclonal antibody, resulting in a very cumbersome approach. The amount of protein uptake is limited to the amount of receptor internalization that can occur, and once internalized, there is limited egress into the cytoplasm.

Some DC receptors target late endosomes resulting in inefficient cross-presentation Finally, the distribution of cross-presenting DC receptors on human DC subsets is poorly understood making the design of such technologies difficult, and can explain why mouse studies do not translate well to humans Another less specific approach is to convert the soluble antigen to a particulate form through attachment to nanoparticles. This approach suffers from the difficulty of delivering sufficient antigen and the fact that DC lose their phagocytic ability as they mature and traffic to lymph nodes.

The present application demonstrates that in the development of peptide-based DC vaccines as well as autologous DC vaccines where antigens are derived from tumors, antigen uptake by the dendritic cells is highly dependent on antigen dose. Cationic lipids can be used safely to facilitate the uptake by the dendritic cells and enhance critical antigen cross-presentation.

The present application therefore focuses on the development of non-DNA/RNA based dendritic cell vaccines and demonstrates a means to facilitate development of such vaccines to enhance antigen uptake and processing by DCs while limiting toxicity towards the DCs.

Yet another significant hurdle for successful immunotherapy is the inhibitory microenvironment of the tumor, which hosts various immune suppressor mechanisms that hamper anti-tumor cytolytic T-cell responses. This effect has been referred to as "immune escape" or "immune tolerization". In an attempt to avoid the inhibitory effects existing in late stage tumors, clinical trials have been performed with patients at the adjuvant setting with minimal residual disease and a high risk of relapse [Sears A K, Perez S A, Clifton G T, el al. AE37: a novel T-cell-eliciting vaccine for breast cancer. Expert Opin Biol Ther. 2011; 11(11): 1543-1550]. The rationale behind vaccination in this clinical setting is that patients with minimal tumor burden still have a fully competent immune system capable of developing robust antitumor responses. Moreover, vaccinating in the adjuvant setting or early-stage cancer has the advantage of minimizing the accumulation of T cells within immune-suppressive tumor environments where they might be inactivated.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In one embodiment described herein, a composition for ex-vivo dendritic cell activation is provided. The composition comprises one or more lipids with at least one cationic lipid and at least one antigen. The composition may include other lipids and a growth factor to enhance dendritic cell viability and proliferation.

The composition for ex-vivo DC activation comprises one or more lipids with at least one cationic lipid and at least one antigen, where the antigen is a protein or a polypeptide found in the tumor or the cancer. Certain cationic lipids are unique in their ability to rapidly bind to dendritic cells in a receptor independent fashion and are rapidly taken up into early endosomes. Importantly, once in early endosomes, cationic lipids facilitate the destabilization of endosomes and delivery of contents into the cytoplasm for entry into the class I processing pathway. This allows much more of the endosomal content to be delivered to the cytoplasm than would occur with targeted receptor uptake. The suitable cationic lipids are also able to provide the immunological danger signals that induce the production of certain cytokines and chemokines that provide activation and proliferation of T-cells and also cause the migration of T-cells into the lymph nodes. The suitable cationic lipids are also capable of reducing the population of Treg cells within the tumor microenvironment preferably when used in conjunction with a tumor antigen.

In another embodiment, a method of treating the subject's dendritic cells ex-vivo, where the subject is a mammal is provided. The method comprises the step of treating the dendritic cells with one or more lipids including an effective amount of at least one cationic lipid and at least one antigen. The composition also comprises growth factors such as GM-CSF and cytokines to facilitate in vitro maintenance and growth of the cells. The at least one antigen is a cancer antigen.

A method of producing a cancer DC vaccine is provided. The method comprises the step of treating the dendritic cells with one or more lipids including an effective amount of at least one cationic lipid and at least one antigen. The composition also comprises growth factors, such as GM-CSF and cytokines to facilitate in vitro maintenance and growth of the cells.

A method of producing a cancer DC vaccine is provided, the method capable of inducing high levels of tumor infiltrating T-cells while also inducing a significant reduction of the Treg population within the tumor microenvironment. The method comprises the step of activating the dendritic cells with one or more lipids including an effective amount of at least one cationic lipid and at least one antigen. The method also comprises further activating DC with growth factors, such as GM-CSF and cytokines to facilitate in vitro maintenance and growth of the cells. When the cationic lipids are combined with a tumor antigen and used for activation of DCs in vitro, and the DCs are then infused into the subject having a cancer, the DCs are capable of altering the tumor microenvironment by increasing the amount of tumor specific CD8+ T-cell within the tumor's microenvironment as well as a significant reduction in the Treg population, thus resulting in a significantly reduced Treg to CD8+ T-cell ratio.

A method of immunizing a subject with a DC vaccine is provided, the method comprising steps of administering to the patient DCs which have been pretreated with one or more lipids including an effective amount of at least one cationic lipid and at least one antigen, where the antigen is a cancer antigen. The method comprises immunizing the subject more than once. The method comprises verifying the level of cancer specific CD8+ T cells and the level of Treg cells in the subject following immunization.

In yet another embodiment, a method of augmenting a protective or therapeutic immune response in a mammal is provided. The method comprises the step of activating dendritic cells with one or more lipids including an effective amount of at least one cationic lipid and antigen together with growth factors in some cases such as GM-CSF and cytokines, and administering the activated dendritic cells to the mammal. In the various embodiments, the mammal is a human.

One embodiment of the invention is directed to the use of cationic lipids, to promote the uptake and presentation of tumor-derived antigens as well as protein and peptide antigens when administered in combination to dendritic cells ex vivo. This may be performed limited toxicity to dendritic cells and may be used in the presence of growth factors and cytokines which are intended to preserve the viability and growth of the dendritic cells and to enhance their proliferation.

Cationic liposomes have been extensively used in vivo for performing transfection and delivery of RNA and DNA for use in gene therapy and also in DNA-based dendritic cell vaccines. Recently cationic lipids have also been reported to be strong adjuvants capable of stimulating strong immune responses via MAP Kinase activation.

Cationic lipids are unique in their ability to rapidly bind to dendritic cells in a receptor independent fashion and are rapidly taken up into early endosomes. Importantly, once in early endosomes, cationic lipids appear to facilitate the destabilization of endosomes and delivery of contents into the cytoplasm for entry into the class I processing pathway. This allows much more of the endosomal content to be delivered to the cytoplasm than would occur with targeted receptor uptake.

In one embodiment of the invention, the disclosure demonstrates that cationic lipids are capable of facilitating the entry of orders of magnitude more protein into the MHC class I and MHC class II pathways than the current approaches such as use of adjuvants to induce dendritic cell maturation.

In one embodiment, the invention provides a composition comprising a cationic lipid and a specific tumor antigen, the composition necessary for preparing a DC vaccine ex vivo against the tumor.

In one embodiment, the composition necessary for preparing a DC vaccine against a tumor comprises a non-nucleic acid antigen, a protein, a polypeptide, a peptide, a lipoprotein, or a lipopeptide.

In one embodiment, the antigen is a tumor antigen, or a mutated tumor antigen. The antigen is a protein product of genes in a patient, the genes selected from a group consisting of oncogenes, tumor suppressor genes, genes with mutations, genes with rearrangements unique to tumor cells, reactivated embryonic gene products, oncofetal antigens, tissue specific differentiation genes, growth factor receptors, and cell surface protein genes.

In one embodiment, the antigen is a microbial antigen, a viral antigen, a bacterial antigen, a fungal antigen, or natural isolates, fragments, and derivatives thereof of microbial antigens.

In one embodiment, the antigen is a viral antigen.

In one embodiment, the composition for DC stimulation or activation to produce a DC vaccine comprises a plurality of peptide antigens.

In one embodiment the composition for DC stimulation or activation to produce a DC vaccine comprises the peptide antigen, which is a self-assembled complex.

In one embodiment, the cationic lipid and the antigen are not structurally linked by a chemical bond.

In one embodiment, the cationic lipid and the antigen are linked by chemical bonds.

In one embodiment, the cationic lipid and the antigen are connected by a linker.

In one embodiment the cationic lipid encapsulates the antigen.

In one embodiment, the cationic lipid forms a liposome.

In one embodiment, the cationic lipid and the antigen forms an emulsion.

In one embodiment the cationic lipid promotes the uptake of the protein or peptide antigen.

In one embodiment the peptide or the protein antigen of the composition for DC uptake and stimulation in the process of development of a DC vaccine, is further modified to reduce the hydrophobicity of the antigen. Hydrophobicity of an antigen may be increased such as, for example, by conjugating to a lipid chain or hydrophobic amino acids in order to improve it's the antigens solubility in the hydrophobic acyl chains of the cationic lipid, while maintaining the antigenic properties of the molecule.

The modified antigen can be a lipoprotein, a lipopeptide, a protein or peptide modified with an amino acid sequence having increased hydrophobicity, and combinations thereof.

The modified antigen may have a linker conjugated between the lipid and the antigen such as, for example, an N-terminal alpha. or .epsilon.-palmitoyl lysine may be connected to antigen via a dipeptide serine-serine linker.

In one embodiment, the cationic lipid comprises R-DOTAP, S-DOTAP, DOEPC, DDA and DOTMA. The cationic lipids are non-toxic and can promote antigen internalization and DC maturation. More specifically, the cationic lipids can promote antigen internalization by dendritic cells as well as their processing, entry into the cytosol and subsequent enhanced presentation via MHC class I and II pathways in vivo. This results in improved antigen-specific immune response.

In other embodiments, the cationic lipid is DOTAP.
In yet other embodiments, the cationic lipid is DOTMA.
In other embodiments, the cationic lipid is DOEPC.
In some embodiments, the cationic lipid is purified.
In some embodiments, the cationic lipid is an enantiomer.
In some embodiments, the enantiomer is purified.
In some embodiments, the composition comprising the cationic lipid and the protein antigen form a particulate composition for DC uptake in the production of a DC cancer vaccine.

In some embodiments, the composition comprising the cationic lipid and the protein antigen form a nanoparticle composition for DC uptake in the production of a DC cancer vaccine.

In some embodiments, the nanoparticles are about less than 10,000 nm in diameter.

In some embodiments, the invention provides a method for the producing a cancer dendritic cell vaccine, the method comprising treating isolated dendritic cells ex vivo with one or more lipids having an effective amount of at least one cationic lipid and at least one cancer antigen.

The current disclosure a therefore provides a method for treating a patient having a cancer, the method comprising: obtaining isolated dendritic cells; activating the isolated dendritic cells with a composition comprising (a) an effective amount of at least one cationic lipid, (b) at least one cancer antigen, and (c) at least a growth factor or at least a cytokine, or a combination thereof, thereby producing activated dendritic cells; administering a suitable number of activated dendritic cells to the patient, wherein administering the suitable number of activated dendritic cells treats the patient having the cancer.

The disclosure also provides a method of evaluating the success of treating the patient having cancer by the method above, the evaluation steps comprising, periodically verifying the level of CD8+ T cells specific to the at least one antigen in the composition; and, verifying the level of Treg cells in the patient subsequent to administering the dendritic cells to the patient, wherein high level of antigen specific CD8+ T cells and low level of Treg cells is indicative of effectively treating the patient for the cancer.

BRIEF DESCRIPTION OF THE DRAWINGS

FIG. 14A. Effect of HPV16-E7, R-DOTAP/HPV16-E7, S-DOTAP/HPV16-E7 and Alum/MPL/HPV16-E7 vaccination on HPV16-specific CD8+ T-cell induction by ELISpot. FIG. 14B. Effect of R-DOTAP, R-DOTAP/HPV16-E7 and S-DOTAP/HPV16-E7 vaccination on regression of established HPV16-positive TC-1 tumors.

DETAILED DESCRIPTION

Figure 1:
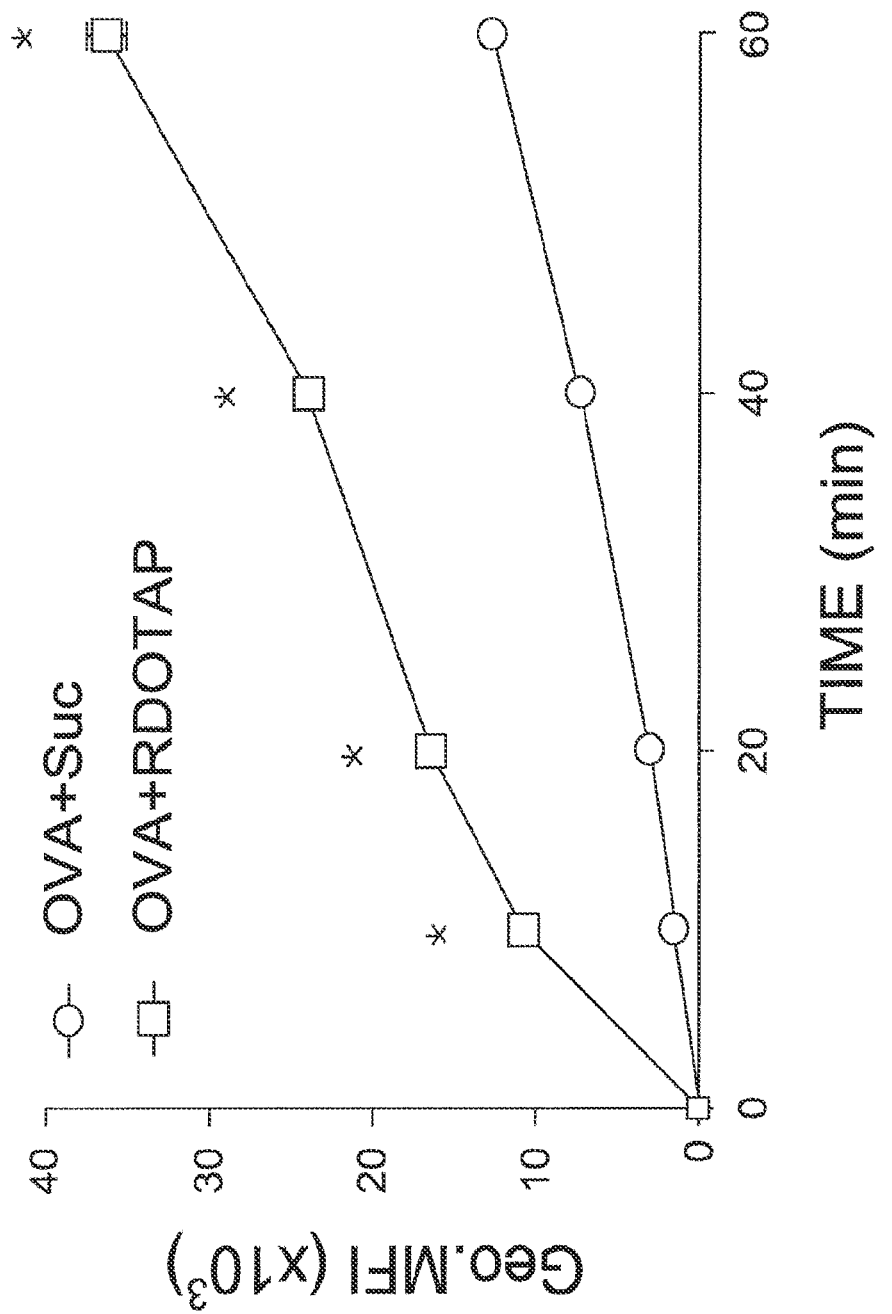
FIG. 1: Geometrical mean fluorescence intensity emitted by the cells incorporating fluorescent ovalbumin Statistical significance was estimated using two-way ANOVA and * values significantly different between treatments.

Due to reported toxicity of cationic lipids to cells especially in vitro, cationic lipids have rarely been used in pharmaceutical products expect as gene transfection agents. Cationic lipids have been used successfully as transfection agents to complex and deliver DNA and RNA into cells including dendritic cells. This approach has also been used in DC vaccines to deliver such RNA/DNA agents when they are used as antigens. In such cases the charge positive charge is neutralized thus minimizing toxicity.

It is possible by methods described herein to improve protein and peptide-based dendritic cell therapies. When treated ex-vivo, cationic lipids as a class, including R-DOATP, S-DOTAP, DOEPC, DDA and DOTMA, can be administered to dendritic cells under conditions which limit toxicity and can promote antigen internalization by dendritic cells as well as their processing, entry into the cytosol and subsequent enhanced presentation via MHC class I and II pathways in vivo. This results in improved antigen-specific immune response. This effect was not common to other lipids, but rather specific to the cationic lipids.

This effect is also independent of the recently reported effect of cationic lipids as immunological adjuvants since both strong (R-DOTAP, DOTMA) and weak (S-DOTAP, DDA) cationic lipid adjuvants as well as the neutral lipid which has been shown to have no in vivo immunological adjuvant effect provided similar effect. Also neither S-DOTAP nor DDA induced effective in vivo antigen-specific immune responses in previous reported studies although they are now shown to promote antigen processing and presentation ex vivo. This effect in facilitating antigen internalization, processing and presentation may also be facilitated by the close proximity of the dendritic cells and cationic lipid in the in vitro/ex vivo setting and may not necessarily occur in vivo. This important discovery has led to a new application of cationic lipids in the development of more effective ex vivo dendritic cell therapies. To date, there has been no reported use of cationic lipids in ex vivo dendritic cell therapies to promote protein and peptide uptake and presentation as this ability of cationic lipids was previously unknown.

Various embodiments of the invention are described herein as follows. In one embodiment described herein, an ex-vivo dendritic cell treatment composition is provided. The composition comprises one or more lipids with at least one cationic lipid and at least one antigen. The composition may include other lipids and a growth factor to enhance dendritic cell viability and proliferation.

A method of treating the subject's dendritic cells ex-vivo, where the subject is a mammal is provided. The method comprises the step of treating the dendritic cells with one or more lipids including an effective amount of at least one cationic lipid and antigen together with growth factors in some cases such as GM-CSF and cytokines to facilitate in vitro maintenance and growth of the cells.

A method of augmenting a protective or therapeutic immune response in a mammal is provided. The method comprises the step of treating the dendritic cells with one or more lipids including an effective amount of at least one cationic lipid and antigen together with growth factors in some cases such as GM-CSF and cytokines, and administering the matured dendritic cells to the subject. In the various embodiments, the composition comprises one or more lipids with at least one cationic lipid and at least one antigen.

This discovery could provide significant benefit in the development of dendritic cell vaccines based on autologous tumor-derived antigens where antigens may be present in very limited quantities and in protein in peptide based dendritic cell vaccines to enable dosing of significantly lower doses of antigen. The dendritic cell vaccine approach has shown significant promise, however lack of a robust T-cell response has limited its acceptance and application as a viable cancer therapy. The present disclosure demonstrates that the use of cationic lipids could be used with limited toxicity to enhance potency of such dendritic cell vaccines utilizing autologous tumor-derived antigens or protein and peptide-based antigens.

Various embodiments of the invention are described herein as follows. In one embodiment described herein, an ex-vivo dendritic cell treatment composition is provided. The composition comprises one or more lipids with at least one cationic lipid and at least one antigen. The composition may include other lipids and a growth factor to enhance dendritic cell viability and proliferation.

The invention demonstrates that cationic lipids can be used as vaccine agents to safely facilitate antigen presentation to dendritic cells as well as presentation to CD4+ and CD8+ T-cells in the context of MHC Class I and Class II. The cationic lipids are effective in facilitating the induction of high levels of tumor infiltrating T-cells while also inducing a significant reduction of the Treg population within the tumor microenvironment. These effects significantly alter the tumor microenvironment by causing a low Treg to CD8+ T-cell ratio resulting in highly effective killing of the tumor cells. In a recent review of Therapeutic Cancer Vaccines *J Clin Invest.* 2015; 125(9):3401-3412, Melief et al state the following; "Suboptimal vaccine design and an immunosuppressive cancer microenvironment are the root causes of the lack of cancer eradication. Drugs or physical treatments can mitigate the immunosuppressive cancer microenvironment and include chemotherapeutics, radiation, indoleamine 2,3-dioxygenase (IDO) inhibitors, inhibitors of T cell checkpoints, agonists of selected TNF receptor family members, and inhibitors of undesirable cytokines. The specificity of therapeutic vaccination combined with such immunomodulation offers an attractive avenue for the development of future cancer therapies.

Antigens

In one embodiment, the cationic lipid is administered with autologous antigens such as antigens derived from the patient's own tumor. In another embodiment, the cationic lipid is administered in combination with non-autologous antigen(s) such as synthetic peptides, recombinant proteins or DNA. In each case the objective is to generate an immune response, which is specific to the antigen(s) with which the dendritic cells are treated together with the cationic lipid. The in-vivo response generated upon infusion of the ex-vivo treated dendritic cells may include production of specific cytotoxic T-cells, memory T-cells, or B-cells resulting in the prevention of or therapeutic response to the specific disease associated with those antigen(s). The antigen can be any tumor-associated antigen or microbial antigen or any other antigen known to one skilled in the art.

A "tumor-associated antigen," as used herein, is a molecule or compound (e.g., a protein, peptide, polypeptide, lipoprotein, lipopeptide, glycoprotein, glycopeptides, lipid, glycolipid, carbohydrate, RNA, and/or DNA) associated with a tumor or cancer cell and which is capable of provoking an immune response (humoral and/or cellular) when expressed on the surface of an antigen presenting cell in the context of an MHC molecule. Tumor-associated antigens include self-antigens, as well as other antigens that may not be specifically associated with a cancer, but nonetheless enhance an immune response to and/or reduce the growth of a tumor or cancer cell when administered to an animal. More specific embodiments are provided herein.

A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In a preferred embodiment, a compound is similar to a naturally-occurring microorganism antigen if it induces an immune response (humoral and/or cellular) similar to a naturally-occurring microorganism antigen. Compounds or antigens that are similar to a naturally-occurring microorganism antigen are well known to those of ordinary skill in the art such as, for example, a protein, peptide, polypeptide, lipoprotein, lipopeptide, glycoprotein, glycopeptides, lipid, glycolipid, carbohydrate, RNA, and/or DNA. Another non-limiting example of a compound that is similar to a naturally-occurring microorganism antigen is a peptide mimic of a polysaccharide antigen.

The term "antigen" is further intended to encompass peptide or protein analogs of known or wild-type antigens such as those described in this specification. The analogs may be more soluble or more stable than wild type antigen, and may also contain mutations or modifications rendering the antigen more immunologically active. Antigen can be modified in any manner, such as adding lipid or sugar moieties, mutating peptide or protein amino acid sequences, mutating the DNA or RNA sequence, or any other modification known to one skilled in the art. Antigens can be modified using standard methods known by one skilled in the art.

Also useful in the compositions and methods of the present invention are peptides or proteins which have amino acid sequences homologous with a desired antigens amino acid sequence, where the homologous antigen induces an immune response to the respective tumor, microorganism or infected cell.

In one embodiment, the antigen in the cationic lipid complex comprises an antigen associated with a tumor or cancer, i.e., a tumor-associated antigen, to make a vaccine to prevent or treat a tumor. As such, in one embodiment, the tumor or cancer vaccines of the present invention further comprise at least one epitope of at least one tumor-associated antigen. In another preferred embodiment, the tumor or cancer vaccines of the present invention further comprise a plurality of epitopes from one or more tumor-associated antigens. The tumor-associated antigens finding use in the cationic lipid complexes and methods of the present invention can be inherently immunogenic, or non-immunogenic, or slightly immunogenic. As demonstrated herein, even tumor-associated self-antigens may be advantageously employed in the subject vaccines for therapeutic effect, since the subject compositions are capable of breaking immune tolerance against such antigens. Exemplary antigens include, but are not limited to, synthetic, recombinant, foreign, or homologous antigens, and antigenic materials may includebut are not limited to proteins, peptides, polypeptides, lipoproteins, lipopeptides, lipids, glycolipids, carbohydrates, RNA and DNA. Examples of such therapies include, but are not limited to the treatment or prevention of breast cancer, head and neck cancer, melanoma, cervical cancer, lung cancer, prostate cancer gut carcinoma, or any other cancer known in the art susceptible to immunotherapy. In such ex-vivo therapies it is also possible to combine the antigen with the cationic lipid without encapsulation.

Tumor-associated antigens suitable for use in the present invention include both naturally occurring and modified molecules which may be indicative of single tumor type, shared among several types of tumors, and/or exclusively expressed or overexpressed in tumor cells in comparison with normal cells. In addition to proteins, glycoproteins, lipoproteins, peptides, and lipopeptides, tumor-specific patterns of expression of carbohydrates, gangliosides, glycolipids, and mucins have also been documented. Exemplary tumor-associated antigens for use in cancer vaccines include protein products of oncogenes, tumor suppressor genes, and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins, and a number of other self proteins.

Specific embodiments of tumor-associated antigens include, e.g., mutated or modified antigens such as the protein products of the Ras p21 protooncogenes, tumor suppressor p53 and HER-2/neu and BCR-ab1 oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self-antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously included in the cancer vaccines of the present invention. It is estimated that close to 16% of the worldwide incidence of cancer can be attributed to infectious pathogens; and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use in the cancer vaccines provided herein include the, hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, Great Britain 1983, the entire contents of which is hereby incorporated by reference.

In another embodiment, the antigen comprises an antigen derived from or associated with a pathogen, i.e., a microbial antigen. As such, in one embodiment, the pathogen vaccines of the present invention further comprise at least one epitope of at least one microbial antigen. Pathogens that may be targeted by the subject vaccines include, but are not limited to, viruses, bacteria, parasites and fungi. In another embodiment, the pathogen vaccines of the present invention further comprise a plurality of epitopes from one or more microbial antigens.

The microbial antigens finding use in the cationic lipid complexes and methods may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipoproteins, lipopeptides, lipids, glycolipids, carbohydrates, RNA, and DNA.

Exemplary viral pathogens include, but are not limited to, viruses that infect mammals, and more particularly humans Examples of virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria may be targeted by the subject compositions and methods in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borella burgdorferi, Legionella pneumophiliaii, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus infuenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatumii, Streptobacillus moniliformis, Treponema pallidum, Treponema pertenue, Leptospira, Rickettsia*, and *Actinomyces israelli*.

Polypeptides of bacterial pathogens which may find use as sources of microbial antigens in the subject compositions include but are not limited to an iron-regulated outer membrane protein, ("IROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("IROMP"), and a structural protein of *Pasteurellosis;* an OMP and a flagellar protein of *Vibrosis anguillarum* and *V. ordalii;* a flagellar protein, an OMP protein, aroA, and purA of *Edwardsiellosis ictaluri* and *E. tarda;* and surface antigen of *Ichthyophthirius;* and a structural and regulatory protein of *Cytophaga columnari;* and a structural and regulatory protein of *Rickettsia*. Such antigens can be isolated or prepared recombinantly or by any other means known in the art.

Examples of pathogens further include, but are not limited to, fungi that infect mammals, and more particularly humans Examples of fungi include, but are not limited to: *Cryptococcus neoformansi, Histoplasma capsulatum, Coccidioides immitis, Blastomyces dermatitidis, Chlamydia trachomatis, Candida albicans*. Examples of infectious parasites include *Plasmodium* such as *Plasmodium falciparum, Plasmodium malariae, Plasmodium ovale*, and *Plasmodium vivax*. Other infectious organisms (i.e. protists) include *Toxoplasma gondii*. Polypeptides of a parasitic pathogen include but are not limited to the surface antigens of *Ichthyophthirius*.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases and human pathogens, the compositions and methods of the present invention are useful for treating infections of nonhuman mammals. Many vaccines for the treatment of non-human mammals are disclosed in Bennett, K. Compendium of Veterinary Products, 3rd ed. North American Compendiums, Inc., 1995; see also WO 02/069369, the disclosure of which is expressly incorporated by reference herein.

Exemplary non-human pathogens include, but are not limited to, mouse mammary tumor virus ("MMTV"), Rous sarcoma virus ("RSV"), avian leukemia virus ("ALV"), avian myeloblastosis virus ("AMY"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RSV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse.

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Lipids

In order to improve incorporation of the antigen into the cationic lipid vesicles and also to improve delivery to the cells of the immune system, the antigen may be modified to increase its hydrophobicity or the negative charge on the antigen. Hydrophobicity of an antigen may be increased such as, for example, by conjugating to a lipid chain or hydrophobic amino acids in order to improve it's the antigen's solubility in the hydrophobic acyl chains of the cationic lipid, while maintaining the antigenic properties of the molecule. The modified antigen can be a lipoprotein, a lipopeptide, a protein or peptide modified with an amino acid sequence having increased hydrophobicity, and combinations thereof. The modified antigen may have a linker conjugated between the lipid and the antigen such as, for example, an N-terminal .alpha. or .epsilon.-palmitoyl lysine may be connected to antigen via a dipeptide serine-serine linker. As discussed in greater detail below, the DOTAP/E7-lipopeptide complex exhibited an enhanced functional antigen-specific CD8 T lymphocyte response in vivo compared to the DOTAP/E7 formulation. Further, the antigen may be manipulated to increase its negative charge by altering the formulation buffer in which the antigen is encapsulated into the cationic lipid complexes or by covalently attaching anionic moieties such as, for example, anionic amino acids to the antigen.

As demonstrated in Example 1 described herein, immunogenicity of the E7 antigen was increased by covalently modifying the antigen. It was possible to covalently attach to the antigen an amino acid sequence such that the resulting antigen amino acid sequence is not found in the parent protein from which the antigen was derived. Studies were performed to demonstrate that the modified antigen provided superior MHC class I binding affinity compared to the native antigen. This superior binding affinity as demonstrated, translated to the generation of a superior in-vivo anti-tumor immune response against HPV-positive TC-1 tumors. The present invention will be further appreciated in light of the following examples.

In some embodiments described herein, the cationic lipid may be in the form of nanoparticle assemblies. As used herein, the term "nanoparticle" refers to a particle having a size measured on the nanometer scale. For example, the "nanoparticle" can refer to a particle having a structure with a size of less than about 10,000 nanometers. In some embodiments, the nanoparticle is a liposome.

As used herein, the term "cationic lipid" refers to any of a number of lipid species which carry a net positive charge at physiological pH or have a protonatable group and are positively charged at pH lower than the pKa. Suitable cationic lipid according to the present disclosure include, but are not limited to: 3-.beta.[.sup.4N-(.sup.1N, .sup.8-diguanidino spermidine)-carbamoyl]cholesterol (BGSC); 3-.beta.[N,N-diguanidinoethyl-aminoethane)-carbamoyl]cholesterol(BGTC); N,N.sup.1N.sup.2N.sup.3Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2 (spermine-carboxamido)ethyl]-N,N-dimethyl-1-p-ropan-aminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3-dioleoyloxy-1,4-butane-diammonium iodide) (Tfx-50); N-1-(2,3-dioleoyloxy) propyl-N,N,N-trimethyl ammonium chloride (DOTMA) or other N-(N,N-1-dialkoxy)-alkyl-N,N,N-trisubstituted ammonium surfactants; 1,2 dioleoyl-3-(4'-trimethylammonio) butanol-sn-glycerol (DOBT) or cholesteryl (4'trimethylammonia) butanoate (ChOTB) where the trimethyl-ammonium group is connected via a butanol spacer arm to either the double chain (for DOTB) or cholesteryl group (for ChOTB); DORI (DL-1,2-dioleoyl-3-dimethylaminopropyl-.beta.-hydroxyethylammonium) or DORIE (DL-1,2-O-dioleoyl-3-dimethylaminopropyl-.beta.-hydroxyethylammoniu-m) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycyl-spermine (DOGS) and dipalmitoyl phosphatidylethanolamylspermine (DPPES), cholesteryl-3.beta.-carboxyl-amido-ethylenetrimethylammonium iodide, 1-dimethylamino-3-trimethylammonio-DL-2-propyl-cholesteryl carboxylate iodide, cholesteryl-3-O-carboxyamidoethyleneamine, cholesteryl-3-.beta.-oxysuccinamido-ethylenetrimethylammonium iodide, 1-dimethylamino-3-trimethylammonio-DL-2-propyl-cholesteryl-3-.beta.-oxysu-ccinate iodide, 2-(2-trimethylammonio)-ethylmethylamino ethyl-cholesteryl-3-.beta.-oxysuccinate iodide, 3-.beta.-N-(N',N'-dimethylaminoethane) carbamoyl cholesterol (DC-chol), and 3-.beta.-N-(polyethyleneimine)-carbamoylcholesterol; O,O'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-distearoyl-sn-glycero-3-ethylphosphocholine (DSEPC); 1,2-dioleoyl-3-trimethylammonium propane (DOTAP); dioleoyl dimethylaminopropane (DODAP); 1,2-palmitoyl-3-trimethylammonium propane (DPTAP); 1,2-distearoyl-3-trimethylammonium propane (DSTAP), 1,2-myristoyl-3-trimethylammonium propane (DMTAP); and sodium dodecyl sulfate (SDS). Furthermore, structural variants and derivatives of the any of the described cationic lipids are also contemplated.

In some embodiment, the cationic lipid is selected from the group consisting of DOTAP, DOTMA, DOEPC, and combinations thereof. In other embodiments, the cationic lipid is DOTAP. In yet other embodiments, the cationic lipid is DOTMA. In other embodiments, the cationic lipid is DOEPC. In some embodiments, the cationic lipid is purified.

In some embodiments, the cationic lipid is an enantiomer of a cationic lipid. The term "enantiomer" refers to a stereoisomer of a cationic lipid which is a non-superimposable mirror image of its counterpart stereoisomer, for example R and S enantiomers. In various examples, the enantiomer is R-DOTAP or S-DOTAP. In one example, the enantiomer is R-DOTAP. In another example, the enantiomer is S-DOTAP. In some embodiments, the enantiomer is purified. In various examples, the enantiomer is R-DOTMA or S-DOTMA. In one example, the enantiomer is R-DOTMA. In another example, the enantiomer is S-DOTMA. In some embodiments, the enantiomer is purified. In various examples, the enantiomer is R-DOPEC or S-DOPEC. In one example, the enantiomer is R-DOPEC. In another example, the enantiomer is S-DOPEC. In some embodiments, the enantiomer is purified.

It should be noted that for the purposes of illustration all examples are performed utilizing a model protein ovalbumin which has been well studied and which is available with a dual fluorescence label. The use of the model protein provides an excellent illustration of how cationic lipids enhance antigen uptake processing and presentation. Also the availability of TCR transgenic T cells specific for the class I and class II restricted OVA peptides enables a detailed study and confirmation of antigen presentation via both routes.

EXAMPLES

All in vitro studies reported in the examples were performed using the model protein ovalbumin as a representative antigen. To assess the effects of cationic lipids on antigen uptake and processing by antigen presenting cells, fluorescent OVA conjugates (DQ-OVA conjugate, and Alexa Fluor® 647 OVA conjugate) were used, which can be easily traced using flow cytometer. In addition, use of Ovalbumin protein as antigen facilitated confirmation of antigen presentation via MHCI and MHC II using Ovalbumin-specific T cell hybridoma cells and TCR transgenic mice (OT-1 and DO11.10) bearing ovalbumin specific CD4 and CD8 T cell receptors. The results shown in this study will be applicable in general to all protein and peptide antigens.

Example 1

Effect of Cationic Lipids on Antigen Uptake by Dendritic Cells

In order to determine the effect of cationic lipids on the uptake of protein antigen, mouse bone marrow derived dendritic cells (BMDCs) were pulsed with Alexa Fluor®647-OVA conjugate and quantified ovalbumin uptake by BMDCs using flow cytometry. Briefly, $2 \times 10^6$ cells/ml BMDCs were incubated at 37° C. for 10-60 minutes in serum free RPMI 1640 cell culture media containing 20 µg/ml ovalbumin (Ovalbumin Alexa Fluor® 647 conjugate; life technologies, cat #034784) and 50 µM cationic lipid (RDOTAP) or 280 mM sucrose diluent. Cells were washed after pulsing to remove non-cell associated ovalbumin and fixed with 1% formaldehyde for flow cytometer analysis. The ovalbumin uptake was quantified using BD LSR II flow cytometer. As shown in FIG. 1, cationic lipids were significantly increased the protein uptake by BMDC at all time points measured. Furthermore, protein uptake occurred very rapidly in presence of cationic nanoparticles, thus suggesting cationic lipids are beneficial in significantly reducing the time for antigen pulsing in the preparation of dendritic cell vaccines.

Example 2

Effect of Cationic Lipids on Antigen Processing by Dendritic Cells and Epithelial Cells In order to determine the effects of cationic lipids on antigen uptake and processing by dendritic cells ex-vivo, a fluorescent ovalbumin protein called DQ-OVA was used. DQ-OVA is non-fluorescent when intact, but emits both red and green fluorescence when the protein is degraded. BMDC were incubated at 37° C. or 4° C. for 1 hr with DQ-OVA alone, or DQ-OVA mixed with different concentrations of the cationic lipid DOTAP. The cells were then washed, fixed, and stained with fluorescent antibodies to CD11c, a marker for dendritic cells. Cells were then analyzed on an LSRII flow cytometer in both red and green fluorescent channels.

Figure 2:
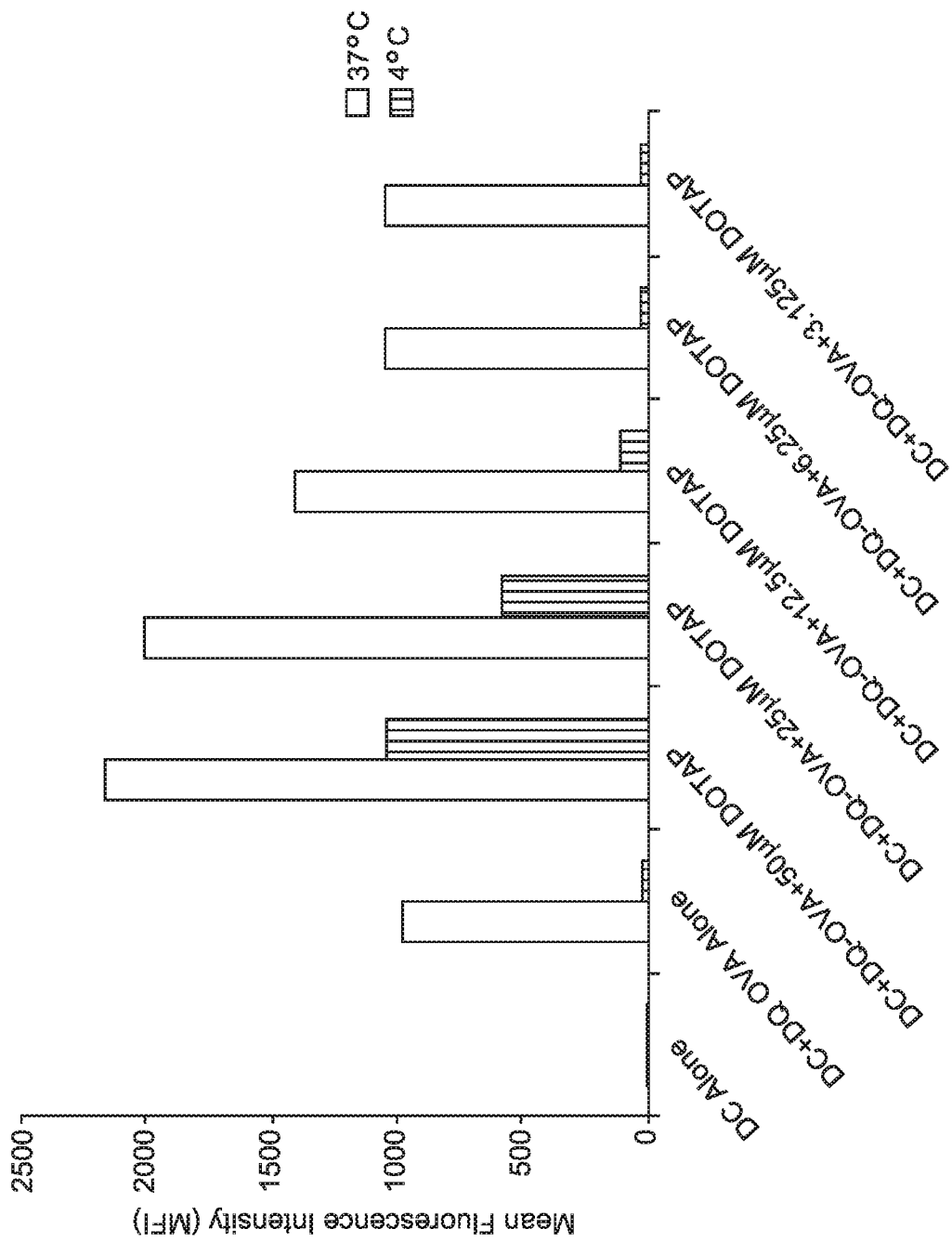
FIG. 2. Mean fluorescence intensity of the green fluorescence of gated CD11c positive cells representing the amount of DQ-OVA taken up and processed by DC.

Results in FIG. 2 show that BMDC incubated with fluorescent DQ-OVA in media alone showed enhanced fluorescence at 37° C. indicating uptake and processing. This represents the well-known mannose receptor mediated uptake of OVA by DC. DOTAP enhances antigen uptake and processing by DC. Graphical representation of the fluorescent uptake of DQ-OVA into BMDC measured by flow cytometry. Plot shows the mean fluorescence intensity of the green fluorescence of gated CD11c positive cells representing the amount of DQ-OVA taken up and processed by DC.

Figure 3:
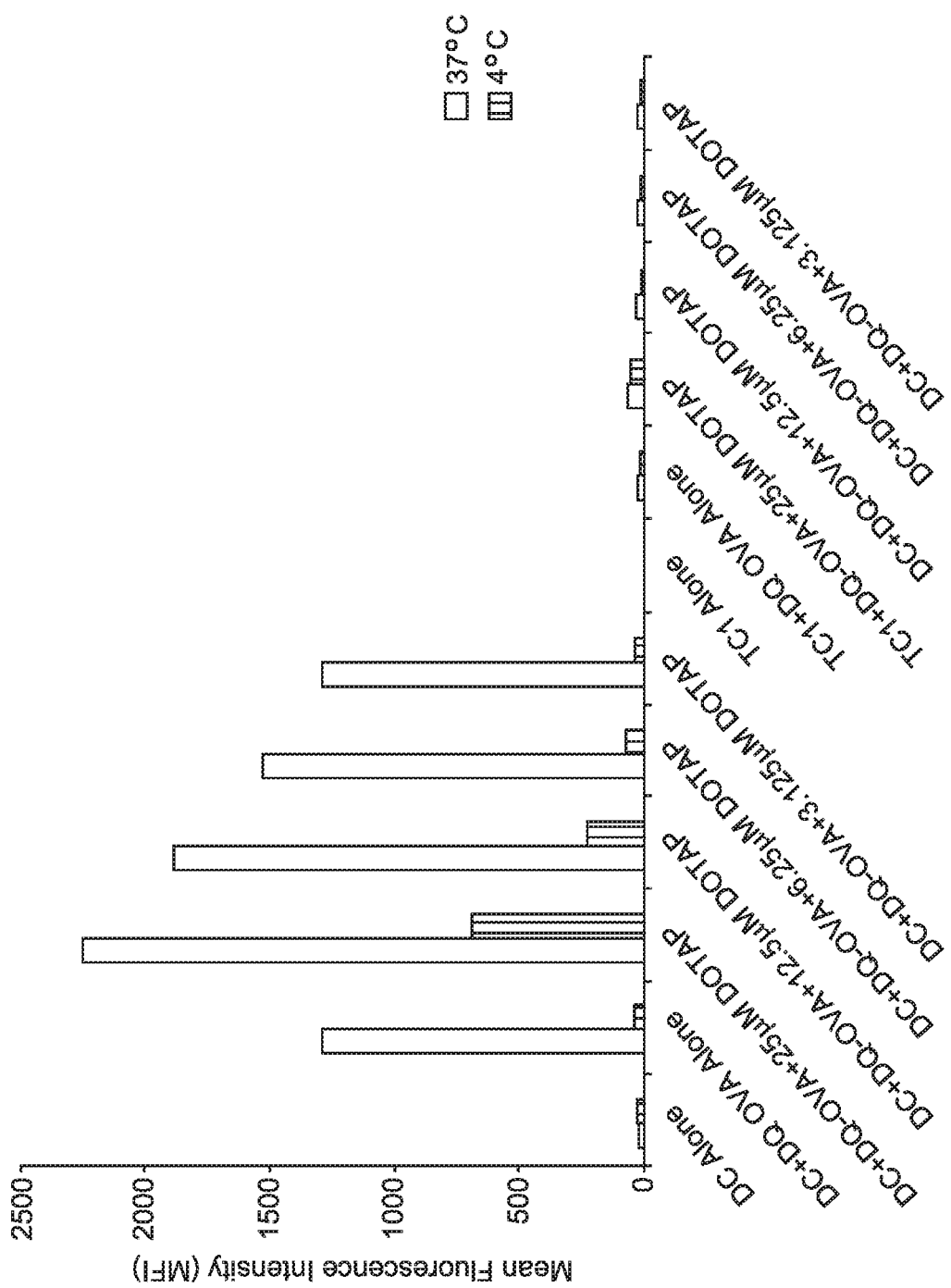
FIG. 3. Mean fluorescence intensity showing DQ-OVA uptake in the presence of the indicated concentration of DOTAP by DC and TC1 cells.

This uptake and processing was inhibited at 4° C. confirming that active cytoskeletal rearrangements are required for this type of uptake. BMDC incubated with DQ-OVA in the presence of the pure R-enantiomer of DOTAP (R-DOTAP) showed a doubling of fluorescence indicating that the cationic lipid R-DOTAP greatly enhances protein uptake and processing in DC. Significant uptake was even seen at 4° C. indicating that R-DOTAP can facilitate protein uptake in the absence of active cellular metabolism. The effect of R-DOTAP was concentration dependent with 50 uM showing the greatest effect. To determine if the R-DOTAP enhancement of protein uptake is cell dependent, a mouse epithelial cell line was incubated with DQ-OVA under identical conditions as the BMDC. Results in FIG. 3 show that this uptake and processing of OVA is only observed in DC and not in TC1 epithelial cells. These data indicate that DOTAP can greatly enhance the uptake and processing of a whole protein into dendritic cells ex-vivo. Further, they indicate that this enhancement is selective for dendritic cells and not other, non-antigen presenting cell types.

Example 3

Figure 4:
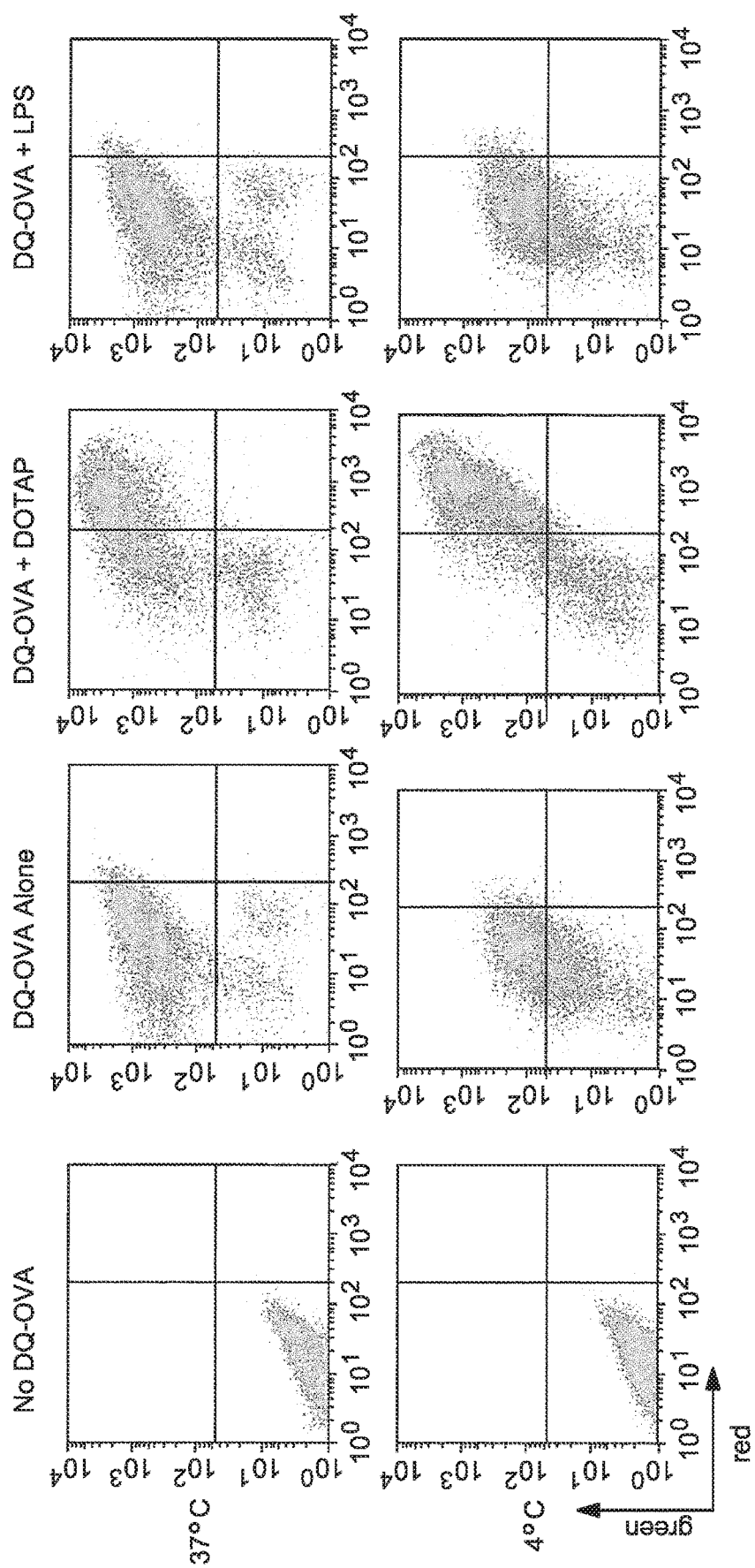
FIG. 4. Flow cytometric analysis of green versus red fluorescence indicating uptake and processing of DQ-OVA by mouse DCs.
Figure 5:
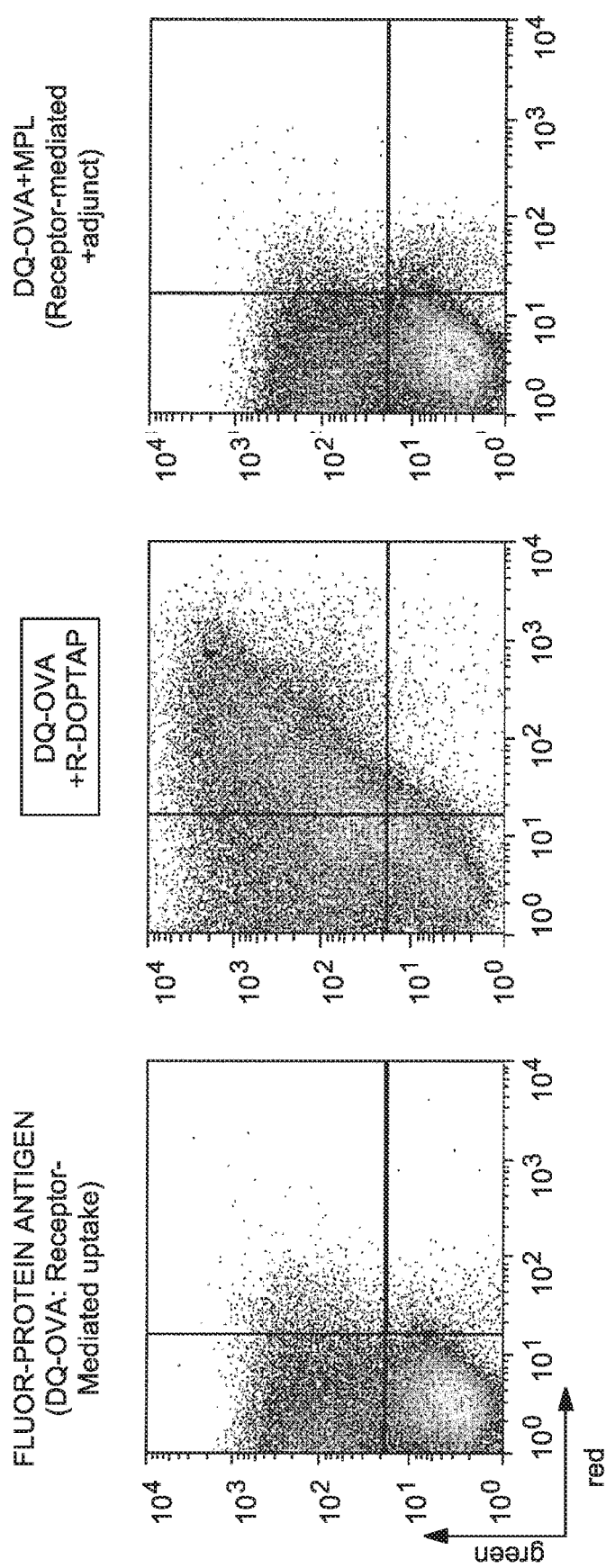
FIG. 5. Green versus red fluorescence indicating uptake and processing of DQ-OVA by mouse DCs in presence of DOTAP or MPL.

Comparison of Effect of Cationic Lipids on Antigen Processing and Endosomal Entry with Known Adjuvants In order to determine whether lipid adjuvants could mediate the same effect as R-DOTAP, BMDC were incubated with DQ-OVA in media alone or with R-DOTAP as described for FIG. 1. In addition, BMDC were incubated under identical conditions with the potent lipid adjuvant lipopolysaccharide (LPS). Mouse bone marrow DC were incubated in the presence of fluorescent DQ-OVA for one hour at either 37° C. or 4° C./azide in the presence of 25 µM DOTAP nanoparticles, 10 µg/ml LPS or media alone, and analyzed by flow cytometry. As shown in FIG. 1, DQ-OVA was actively taken up and processed by DC in the absence of R-DOTAP, but the uptake was greatly enhanced in the presence of R-DOTAP manifested as a strong increase in red fluorescence. In contrast, no such enhancement was observed with LPS treatment, as shown in FIG. 4. Monophosphoryl lipid-A (MPL) is a lower toxicity derivative of LPS that is now an FDA approved adjuvant in several vaccines. Similar to results with LPS in FIG. 5, MPL showed no ability to facilitate protein uptake in BMDC.

Example 4

Effect of Cationic Lipids on Antigen Processing in a Human Monocyte Cell Line

Figure 6:
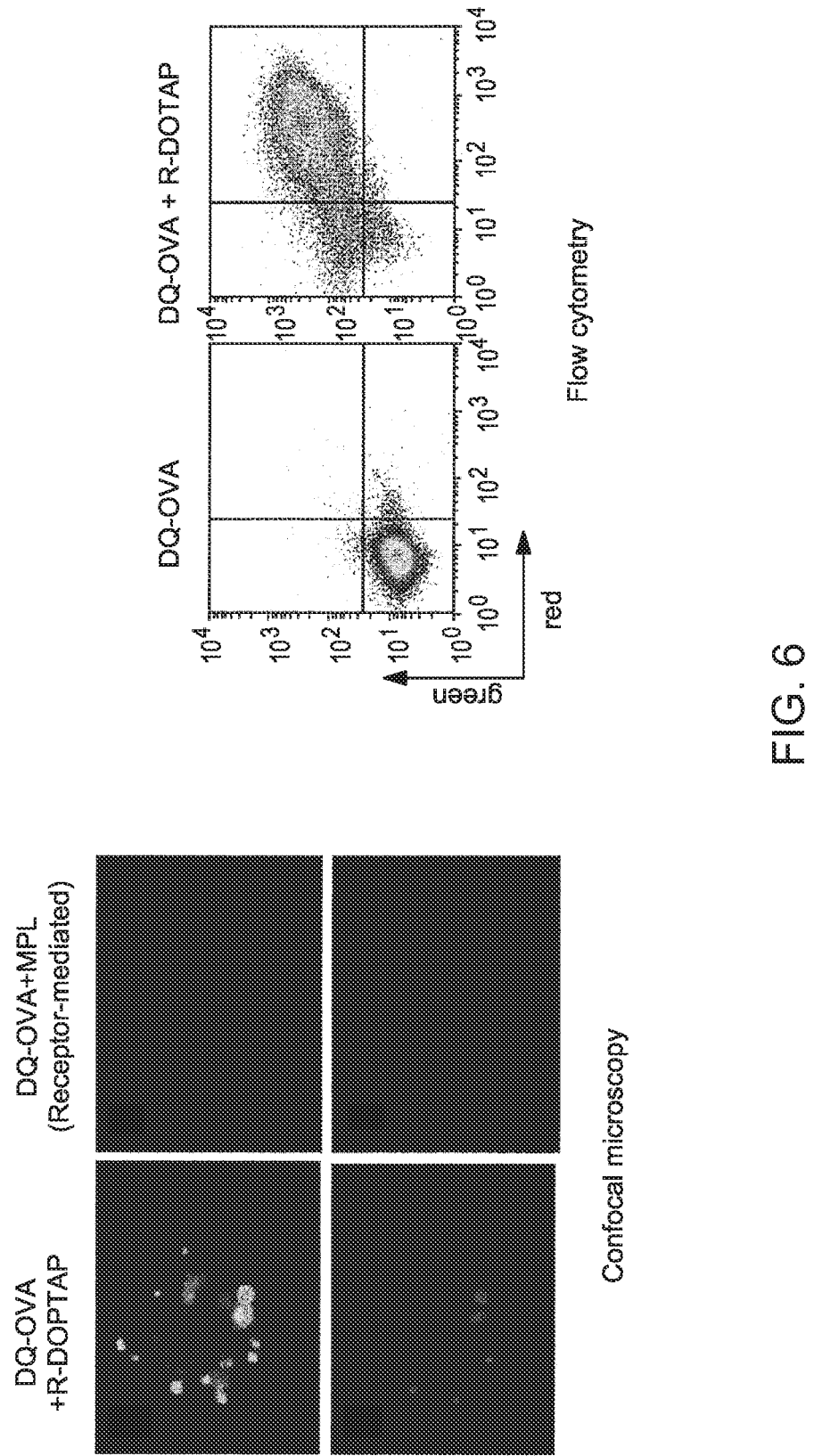
FIG. 6. Laser scanning confocal microscopy and flow cytometry indicating uptake and processing of DQ-OVA.

To determine the effect of cationic lipids on human cells, a human monocyte cell line, THP-1 was used to assess DQ-OVA uptake ex-vivo. THP-1 is representative of human blood derived monocyte cells, the same cells that are used to produce DC from patients in ex vivo DC therapy approaches. THP-1 cells were incubated with DQ-OVA (10 μg/ml) in the presence (A, B) or absence (C, D) of R-DOTAP (25 μg/ml) for 1 h at 37° C. The same cell was imaged using a laser scanning confocal microscope and quantitated by measuring green versus red fluorescence by flow cytometry. The results in FIG. 6 show that R-DOTAP dramatically enhanced the uptake of DQ-OVA in THP-1 cells. Unlike the mouse BMDC, no uptake of DQ-OVA was observed in the absence of R-DOTAP. This is likely because the blood derived monocyte is a precursor of the dendritic cell but does not yet have the necessary receptors for protein uptake. This result is significant because it shows that R-DOTAP can facilitate uptake and processing in cells that would ordinarily be incapable of receptor-mediated uptake. Another striking observation from FIGS. 6A and B, is the accumulation of processed OVA in endocytic vesicles. It is well known that proteins in endocytic vesicles are efficiently incorporated into MHC class II molecules for stimulating CD4 T cells or shuttled into the cross-presentation pathway for presentation on MHC class I to CD8 T cells. Thus, cationic lipids facilitate protein uptake in a manner which maximally optimizes presentation of antigen onto both MHC class I and class II molecules, resulting in maximal stimulation of CD8 and CD4 T cells respectively.

Example 5

Effect of DOTAP and DOTMA on Antigen Processing and Cross-Presentation to MHC Class I Restricted T Cells In order to verify that the cationic lipid facilitated uptake of antigen actually translates into enhanced antigen presentation on MHC class I (cross presentation), two distinct methods were utilized to assess cross-presentation in presence of cationic lipids. In the first method T cell hybridoma cell line (B3Z cells) was used. This cell line can respond to antigen presenting cells cross-presenting SIINFEKL (SEQ ID NO: 2) peptide through MHC I by inducing .beta.-galactosidase enzyme, which can be quantified using .beta.-gal assay. BMDCs with ovalbumin peptide (OVA241-270; SMLVLLPDEVSGLEQLESIINFEKLTEWTS (SEQ ID NO: 3) admixed with 50 .mu.M RDOTAP or isotonic sucrose (280 mM) (Suc) alone. Peptide pulsed BMDCs were washed and co-cultured at 37.degree. C. with antigen specific T cell hybridoma cell line (B3Z cells) that can recognize SIINEKL (SEQ ID NO: 2) epitope presented by antigen presenting cells through MHCI (H2Kb). B3Z cell responds to SIINFEKL (SEQ ID NO: 2) epitope by producing .beta.-galactosidase enzyme, which was quantified using colorimetric .beta.-galactosidase assay as an indicator of peptide cross presentation by dendritic cells. Data represent relative absorbance (570 nm) in test wells (arbitrary units). Statistical significance was estimated using two-way ANOVA and * values were significantly different between treatments (shown in FIG. 7).

Figure 7:
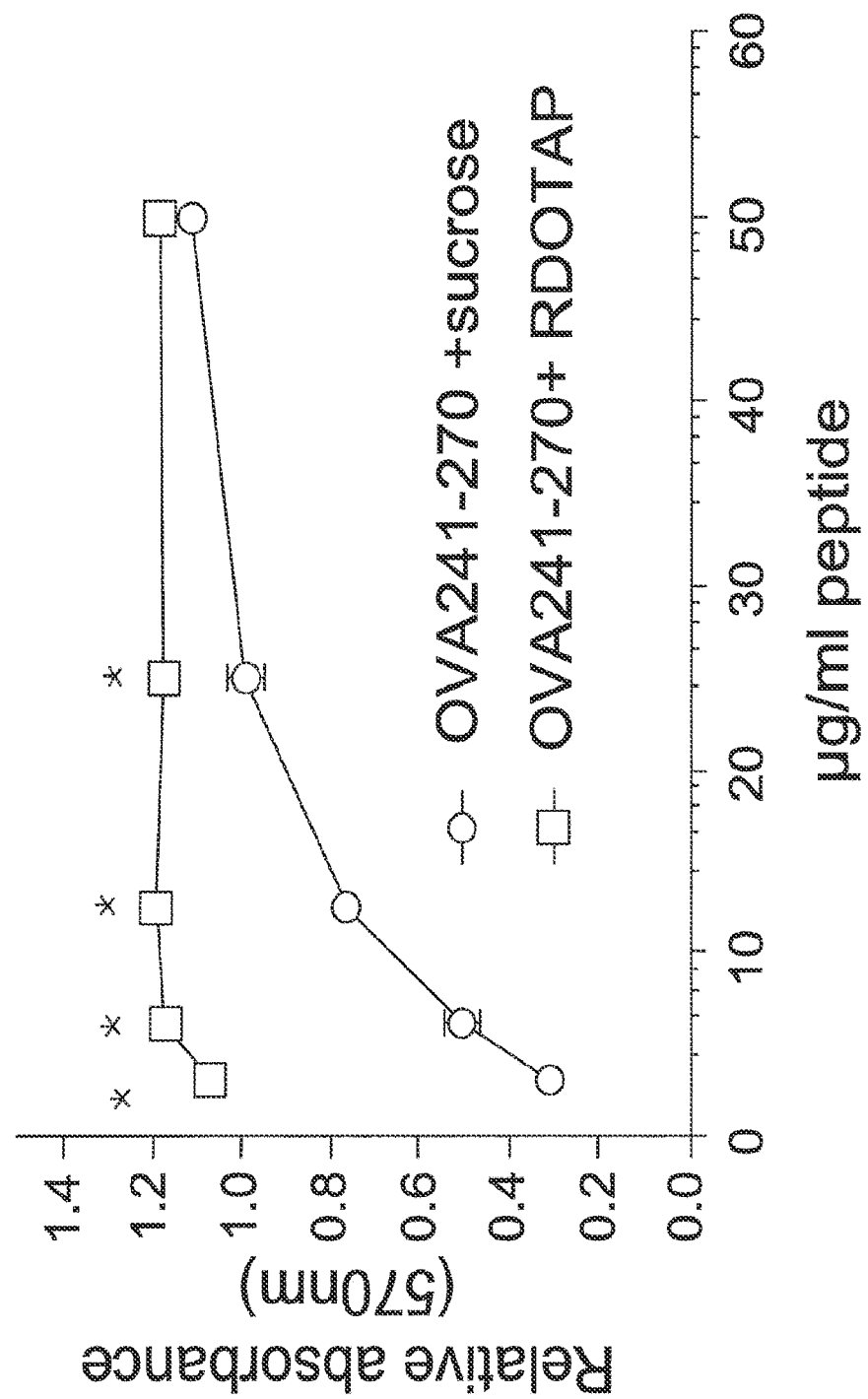
FIG. 7: Beta galactosidase assay showing measurement of relative absorbance of (570 nm) (arbitrary units). Statistical significance was estimated using two-way ANOVA and * values significantly different between treatments.

It was observed that peptide pulsing with cationic nanoparticles significantly decreased the concentration of peptide required for efficient pulsing as indicated in the FIG. 7. This method utilizing cationic lipids provides a significant advantage in peptide loading especially under conditions where the dendritic cell cross-presentation is limited by the amount of peptide antigen available or the peptide concentrations (for example: in autologous tumor vaccines where the epitopes are limiting).

In the second method, T cells from a TCR transgenic mice (OT-1) were used in which all T cells are specific for an internal peptide of OVA. These T cells will only proliferate if presented with DC which have processed OVA and presented an OVA peptide on MHC class I molecules.

Figure 8:
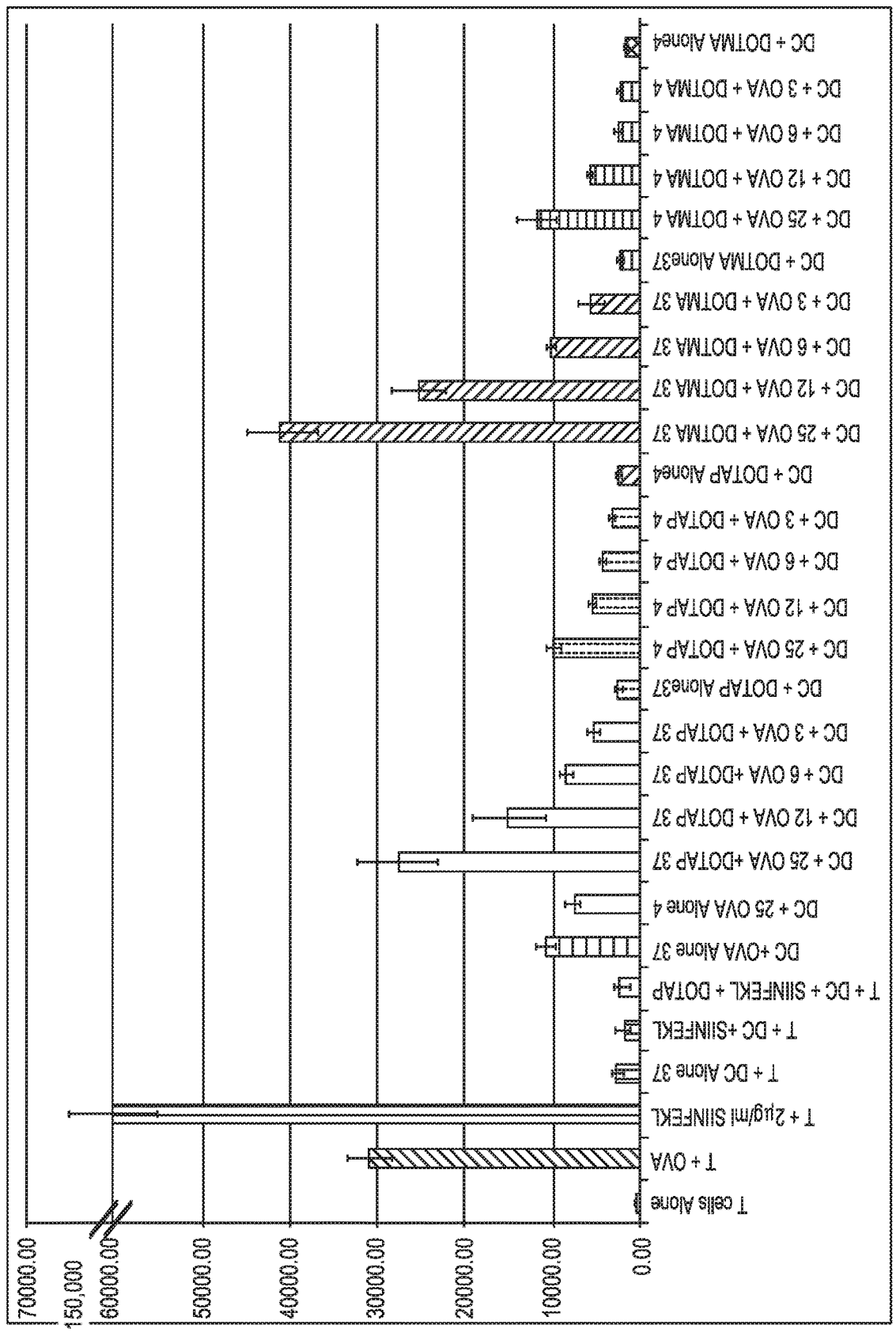
FIG. 8: Mean CPM of $^3$H-thymidine uptake by OT1 cells in presence of OVA stimulated BDMC with or without DOTAP.

Thus, this represents a stringent assay for cross presentation. BMDC were incubated with different concentrations of the whole OVA protein in the presence or absence of two cationic lipids, either DOTAP or DOTMA for 1 hr at 37° C. The DC were then washed, fixed and added to the OVA peptide specific T cells. The results in FIG. 8 show that DC incubated with OVA in the presence of DOTAP or DOTMA cross presented antigen to the CD8+ T cells much more strongly than DC incubated with OVA without cationic lipid. This response was dose dependent with respect to the OVA concentration, and was even apparent when DC were incubated with OVA at 4° C.

These results demonstrate that the enhanced uptake of antigen mediated by cationic lipids actually results in efficient processing of antigen and entry of peptides into MHC class I pathway, an absolute prerequisite for effective activation of CD8 T cells.

Example 6

Figure 9:
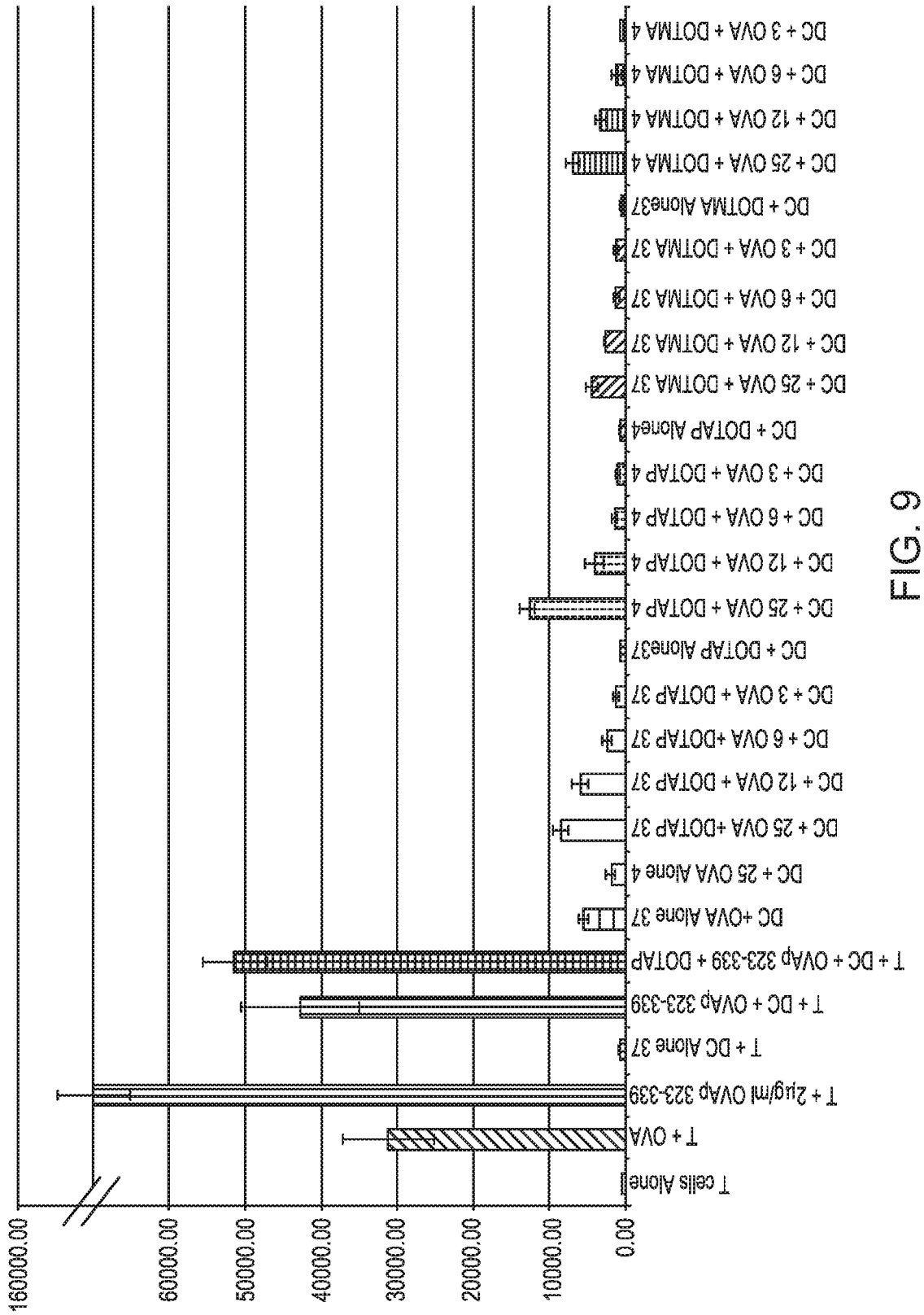
FIG. 9: Mean CPM of $^3$H-thymidine uptake by DO11.10 splenocytes and OVAp 323-339.

Effect of DOTMA and DOTAP on Antigen Processing and Cross-Presentation to MHC class II Restricted T Cells To examine whether cationic lipids actually enhance antigen presentation to CD4 T cells, cells from the DO11.10 transgenic mouse, with T cells specific for an OVA peptide presented on MHC class II molecules, was used. The results in FIG. 9 show that the same trend was observed for class II presentation as was observed for class I presentation in FIG. 8. OVA uptake in the presence of cationic lipids resulted in enhanced antigen presentation to CD4 T cells.

These results demonstrate that the enhanced uptake of antigen mediated by cationic lipids actually results in efficient processing of antigen and entry of peptides into MHC class II pathway, an absolute prerequisite for effective activation of CD4 T cells.

Example 7

Effect of DOTAP on Antigen Presentation in an Actual Vaccine Setting In Vivo

Figure 10:
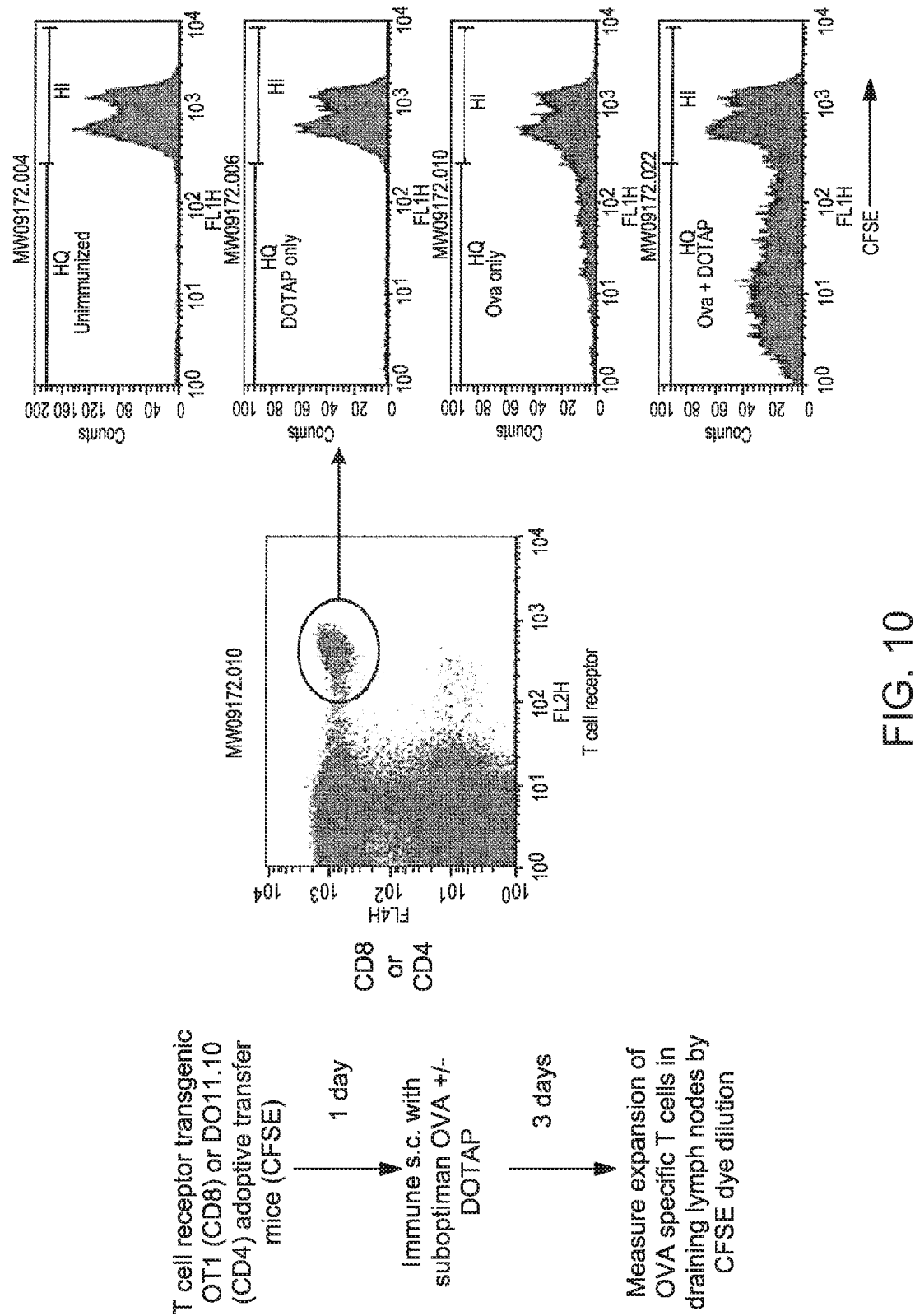
FIG. 10: Flow cytometry analysis of CFSE dilution profile of T cells from draining lymph nodes of mice injected with OVA alone or OVA with DOTAP.

To model the effect of DOTAP in an actual vaccine setting, a T-cell receptor adoptive transfer system was used. This system utilizes T cells from the same TCR transgenic mice described for FIGS. 8 and 9, but analyzes how they respond in vivo following vaccination. OT-1 (OVA specific CD8+) or DO11.10 (OVA specific CD4+) T cells were first labeled with a tracking fluorescent dye, CFSE. 24 Hours later, mice were then injected with OVA alone or OVA in presence of DOTAP. If these T cells recognize antigen presented by DC in the draining lymph node following immunization, they will proliferate and the CFSE dye will be diluted in all daughter cells. Mice were then injected with OVA with or without DOTAP. After three days the draining lymph nodes at the vaccination site were removed and the T cells were stained with anti-CD8 and anti-CD4 antibodies, and the level of CFSE visualized by flow cytometry. The results in FIG. 10 show that CFSE labeled OT1 (CD8 T cells) or DO11.10 (CD4 T cells) when further injected (immunized) with either whole OVA or whole OVA mixed with DOTAP. significant T cell division occurred only when mice were vaccinated with OVA+DOTAP. These results demonstrate that the antigen delivery properties of DOTAP results in enhanced T-cell responses in the draining lymph nodes following vaccination.

Example 8

Effect of Various Lipids on Antigen Processing and Cross-Presentation to MHC Class I Restricted T Cells To examine the effect of other cationic lipids and neutral lipids on antigen uptake and cross presentation, BMDC were incubated in the presence of the whole OVA protein and various concentrations of DOTAP DOTMA, DOPC, DOEPC or DDA for 30 min at 37.degree. C. or 4.degree. C. DC were then washed and added to OT1 splenocytes (TCR transgenic T cells specific for the class I restricted OVA peptide SIINFEKL (SEQ ID NO: 2)) in microtiter plates and cultured for three days at 37.degree. C. Plot shows the mean CPM of .sup.3H-thymidine uptake during the final 18 h of culture. Control cultures contained OT1 splenocytes and SIINFEKL (SEQ ID NO: 2) only which bypasses the need for antigen processing.

Figure 11:
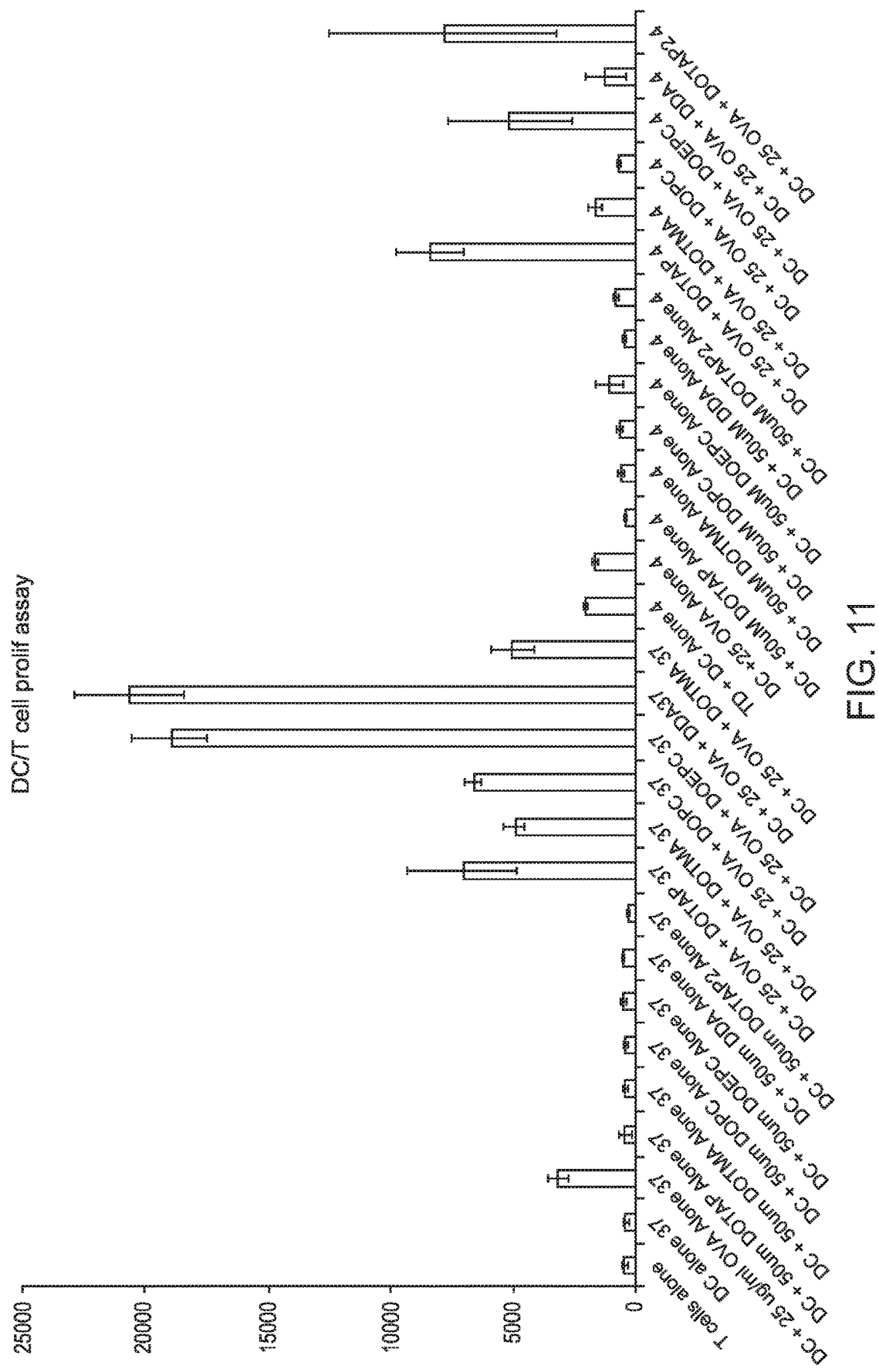
FIG. 11: OT1 T cell proliferation in the presence of BMDC "pulsed" with OVA and different cationic lipids. Mean CPM of $^3$H-thymidine uptake during the final 18 h of culture.

The results in FIG. 11 show that cationic lipids DOTAP, DOTMA, DOEPC, and DDA all facilitated enhanced uptake and cross-presentation of OVA by BMDC. The cationic lipid S-DOTAP also facilitated uptake and presentation. The neutral lipid DOPC also facilitated uptake and presentation. These results show that cationic lipids as a class are effective at mediating effective antigen uptake and delivery of protein antigens by dendritic cells.

Example 9

Cationic Lipids Improve the Efficacy of Dendritic Cell Vaccine

To demonstrate as a proof of concept that cationic lipids improve the efficacy of dendritic cell based vaccines in vivo, the effect of cationic lipids were evaluated on CTL induction by dendritic cell vaccine. B6 mice were immunized with BMDCs pulsed with peptide alone (palmitoylated-KSSSI-INFEKL) (SEQ ID NO: 1) or peptide admixed with cationic (50 .mu.M R-DOTAP, DOTMA) or neutral lipid nanoparticles (DOPC), or isotonic sucrose. Groups of C57BL6/J mice (n=5) were immunized subcutaneously with peptide pulsed BMDCs on day 0 and day 7 and vaccine responses were assessed on day 14 by measuring antigen specific IFN-.gamma. responses using ELISPOT Assay. Data represent spot forming cells in each mouse from a representative study.

Figure 12:
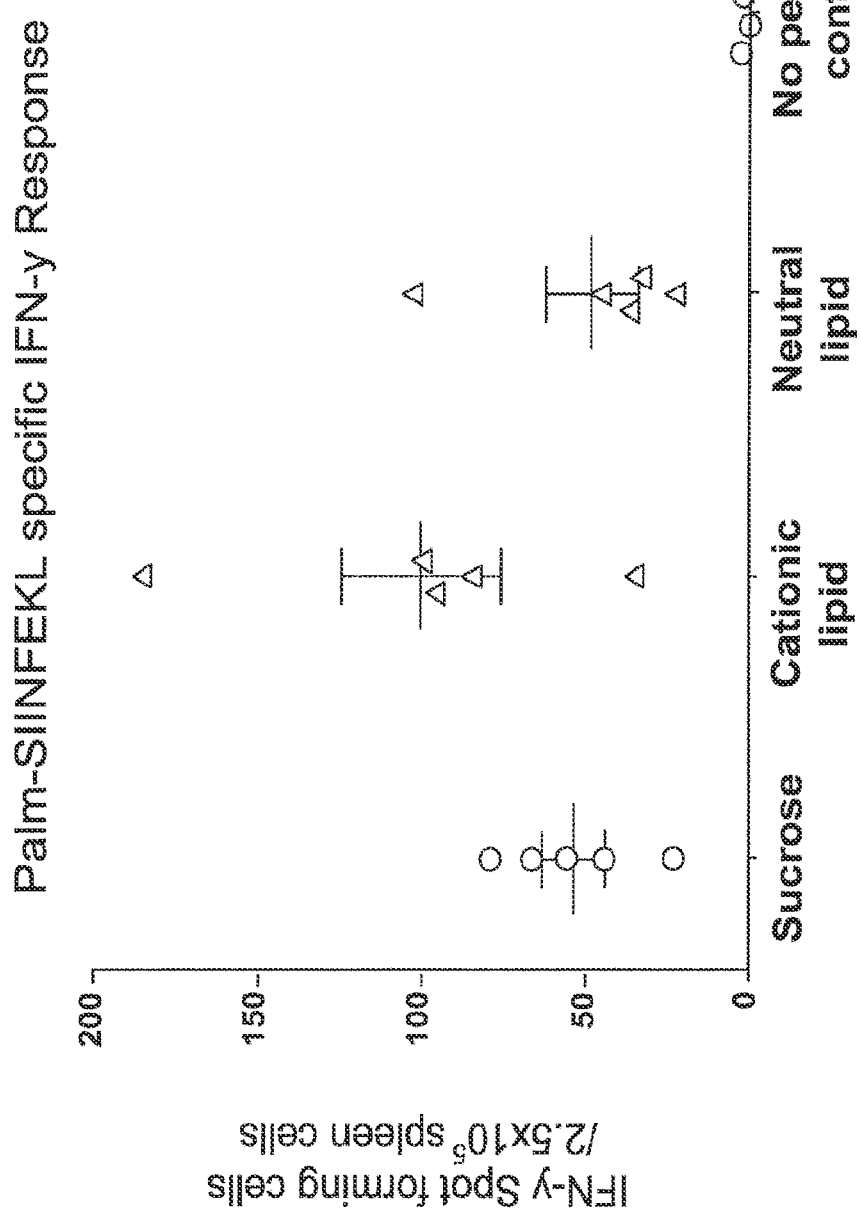
FIG. 12: IFN-y ELISPOT assay of T cells from mice vaccinated with BMDCs pulsed with palmitoylated-KSSSI-INFEKL (SEQ ID NO: 1) peptide admixed with cationic lipids (RDOTAP, DOTMA) or neutral lipid (DOPC) or isotonic sucrose (280 mM).
Figure 13A:
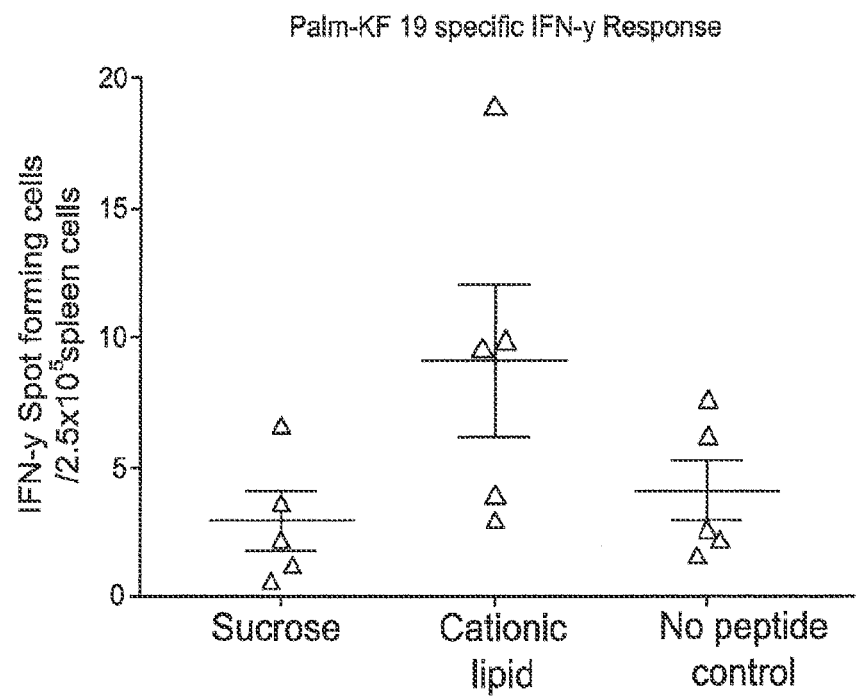
FIGS. 13A-13B: IFN-y ELISPOT assay of T cells from mice vaccinated with BMDCs pulsed with tumor associated peptide (FIG. 13A) HPV associated antigen and (FIG. 13B) Mucin 1, admixed with cationic lipids (RDOTAP, DOTMA) or neutral lipid (DOPC) or isotonic sucrose (280 mM).
Figure 13B:
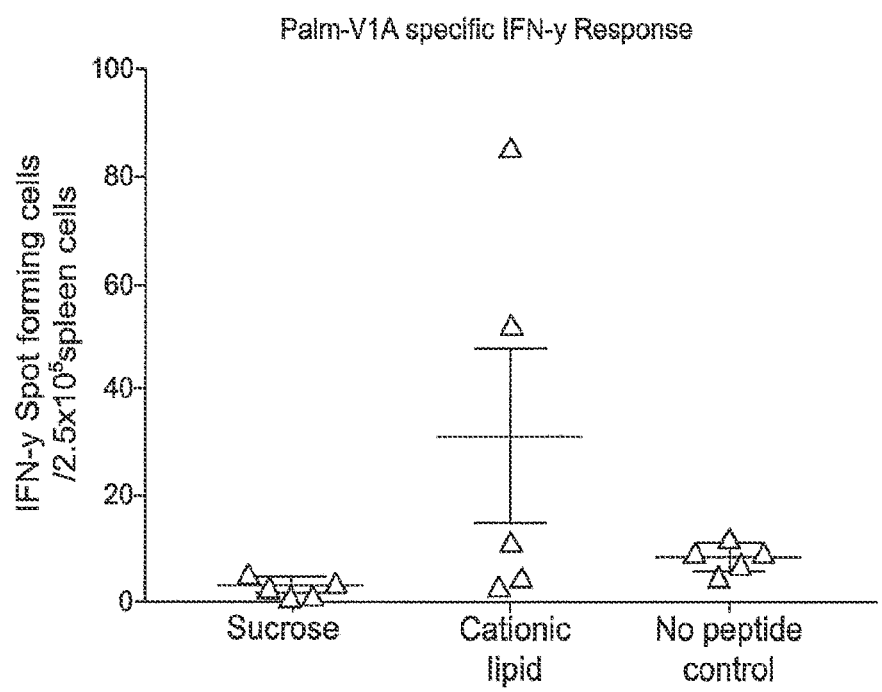

As shown in FIG. 12, pulsing dendritic cells with peptide loaded cationic nanoparticles significantly increased the antigen-specific T cell responses induced by the vaccine, thus directly demonstrating that beneficial effects of cationic nanoparticles seen in in vitro assays can influence the dendritic cell based vaccine efficacy. In the following studies, the cationic nanoparticle efficacy in CTL induction were examined using tumor associated antigens derived from HPV associated and mucin 1 associated tumor. As expected, tumor associated antigen loaded cationic nanoparticles improved the antigen-specific T cell immune responses mounted in the vaccinated mice (FIG. 13). In this experiment mouse BMDC were pulsed for 10 minutes with peptide mixture containing tumor associated antigens (HPV tumor associated (a) or mucin 1 associated (b) admixed with 50 µM cationic lipids (RDOTAP) or isotonic sucrose (280 nM). Groups of C57BL6/J mice (n=5) were immunized subcutaneously with peptide pulsed BMDCs or non-pulsed BMDCs on day 0 and day 7 and vaccine responses were assessed on day 14 by measuring antigen specific IFN-γ responses using ELISPOT Assay. Data represent spot forming cells in each mouse from a representative study. DOTAP, DOTMA and DOPC showed some enhancement, while DOEPC and DDA showed strong enhancement of antigen presentation. Note: DDA formed a precipitate when diluted with OVA. While all the cationic lipids show enhancement, the overall magnitude is variable from experiment to experiment. Also, the neutral lipid DOPC showed some enhancement in this experiment.

These results show that cationic lipids as a class are effective at mediating effective antigen uptake and delivery of protein antigens by dendritic cells. Furthermore, the dendritic cells pulsed with antigen loaded cationic lipids can greatly improve the dendritic cell vaccine efficacy.

Example 10

Effect of R-DOTAP on the Population of T-Cells and Regulatory T Cells within the Tumor Micro-Environment Antigen specific CD8+ T cells were induction by R-DOTAP and S-DOTAP.

Figure 14A:
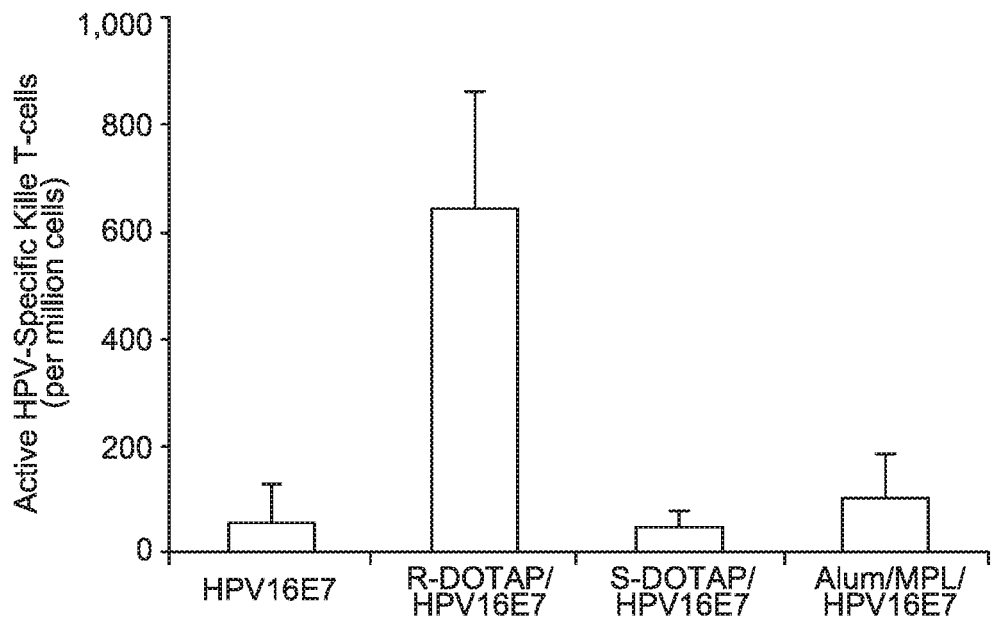
FIG. 14A-14B.
Figure 14B:
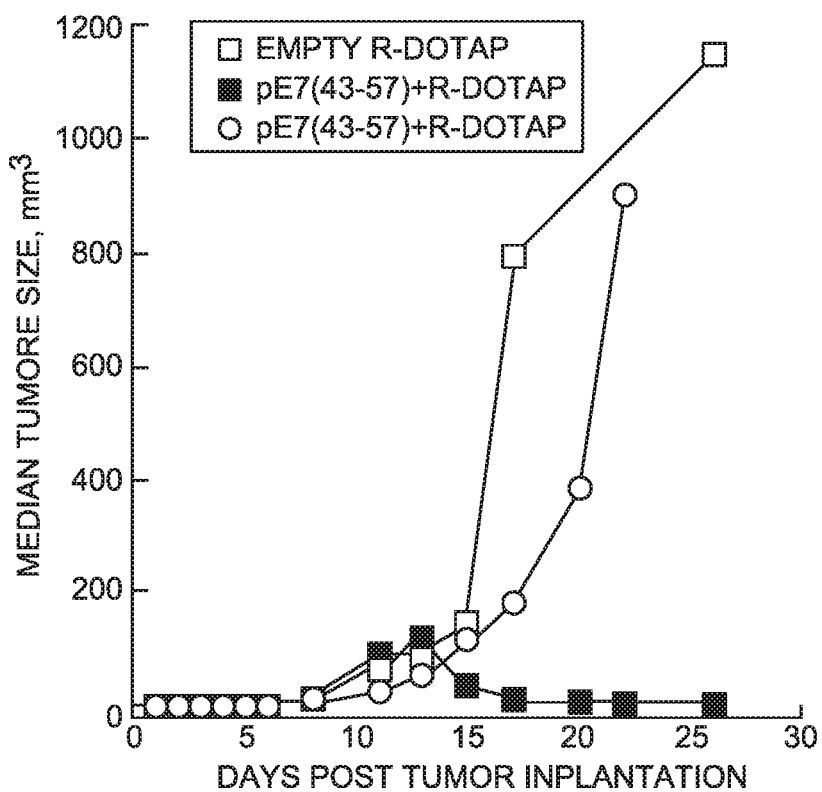

C57 black mice were vaccinated with various formulations:
Group 1: KF18 HPV peptide (GQAEPDRAHYNIVTF) (SEQ ID NO: 4)
Group 2: KF18 HPV peptide+R-DOTAP liposomes
Group 3: KF18 HPV peptide+S-DOTAP liposomes
Group 4: KF18 peptide+MPL/Alum adjuvant 5 mice per group were injected with the various formulations. The mice were vaccinated on Day 0 and Day 7 and sacrificed on Day 14. The splenocytes were removed and ELISPOT studies performed. The splenocytes were stimulated with the peptide RAHYNIVTF (RF9) (SEQ ID NO: 5), the HPV16 CD8+ T-cell epitope peptide recognized by the C57 mice. The studies demonstrate that R-DOTAP was effective in inducing strong HPV-specific CD8+ T-cell responses. However, S-DOTAP which demonstrated identical ability to promote antigen uptake, internalization and processing, as well as maturation of dendritic cells, did not result in an enhanced CD8+ T-cell response beyond what was seen with the peptide alone (FIG. 14A). MPL was ineffective in promoting antigen uptake compared to both R-DOTAP and S-DOTAP, hence the significantly lower CD8+ T-cell response compared to R-DOTAP was expected. An additional example of this effect is observed with the cationic lipid DDA. FIG. 14B demonstrates the ability of DDA to facilitate antigen uptake and presentation. However, it has been reported that in order to induce strong antigen-specific T-cell responses that DDA is used in combination with strong adjuvants (Brandt L. et al, ESAT-6 Subunit Vaccination against Mycobacterium tuberculosis, Infect Immun. 2000 February; 68(2): 791-795).

Due to the observation of enhanced antigen uptake and presentation by R-DOTAP as well as the superior CD8+ T-cell induction in vivo, a head to head study was performed using R-DOTAP and GM-CSF based immunotherapy with tumor antigens to study the impact of the 2 vaccines on their impact on T cell infiltration in to the tumor micro-environment as well as the ability to down regulate the immunosuppressive tumor microenvironment.

C57 mice were divided into the following groups of 8 mice per group: R-DOTAP+HPV16 E7 peptide KF18

(GQAEPDRAHYNIVTF) (SEQ ID NO: 4) , GM-CSF+ HPV16 E7 peptide KF18, R-DOTAP, GM-C SF, HPV16 E7 peptide KF18, untreated. 1.times.10.sup.5 TC-1 tumor cells were injected into the flank of the mice on day 0. The various formulations were administered on Days 12 and 19 after tumor implantation. On day 19 4-5 mice per group were sacrificed and a number of evaluations performed to evaluate the immunology of the tumor microenvironment.

Figure 15:
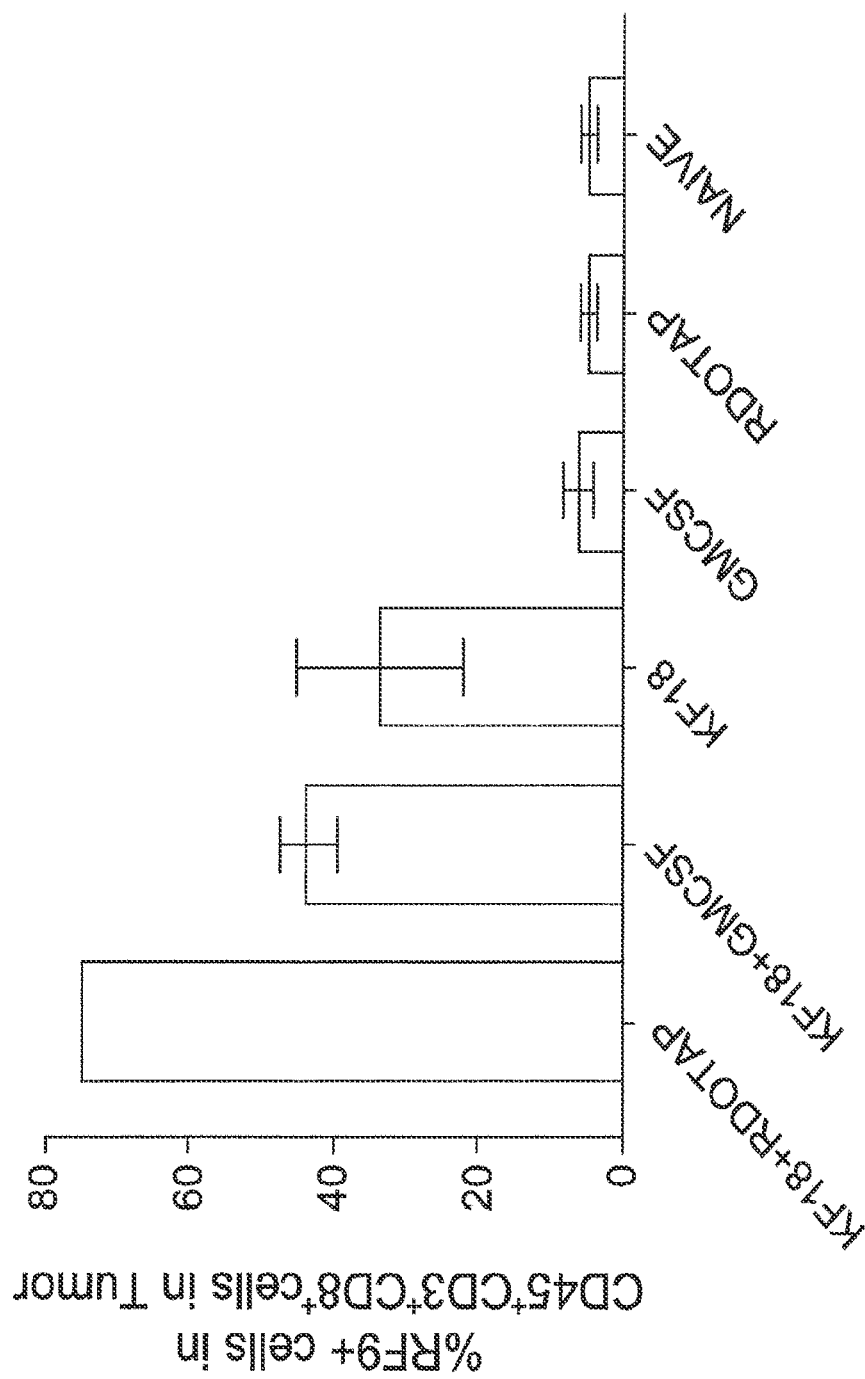
FIG. 15: Quantitation of tumor-infiltrating HPV16-specific CD8+ T by RF9 specific dextramers analyzed using flow cytometry. Data represents mean±SEM of 4-5 mice in each group.

RF9 specific dextramer staining and flow cytometry were utilized to quantify the number of HPV-specific CD8+ T-cells that had infiltrated into the tumor micro-environment. The study quantified the number of CD8+ T cells specific to the mouse epitope RF9. These CD8+ T cells were measured as a percentage of all immune cells (CD45, CD3 and CD8) present in the tumor. Antigen specific T cells infiltrating into the tumor were measured using RF9 specific dextramers by flow cytometry. FIG. 15 shows the results of the study and demonstrate statistically significant increase in HPV-specific T-cells compared with R-DOTAP/HPV compared to all other groups. Data represents mean±SEM of 4-5 mice in each group.

Figure 16:
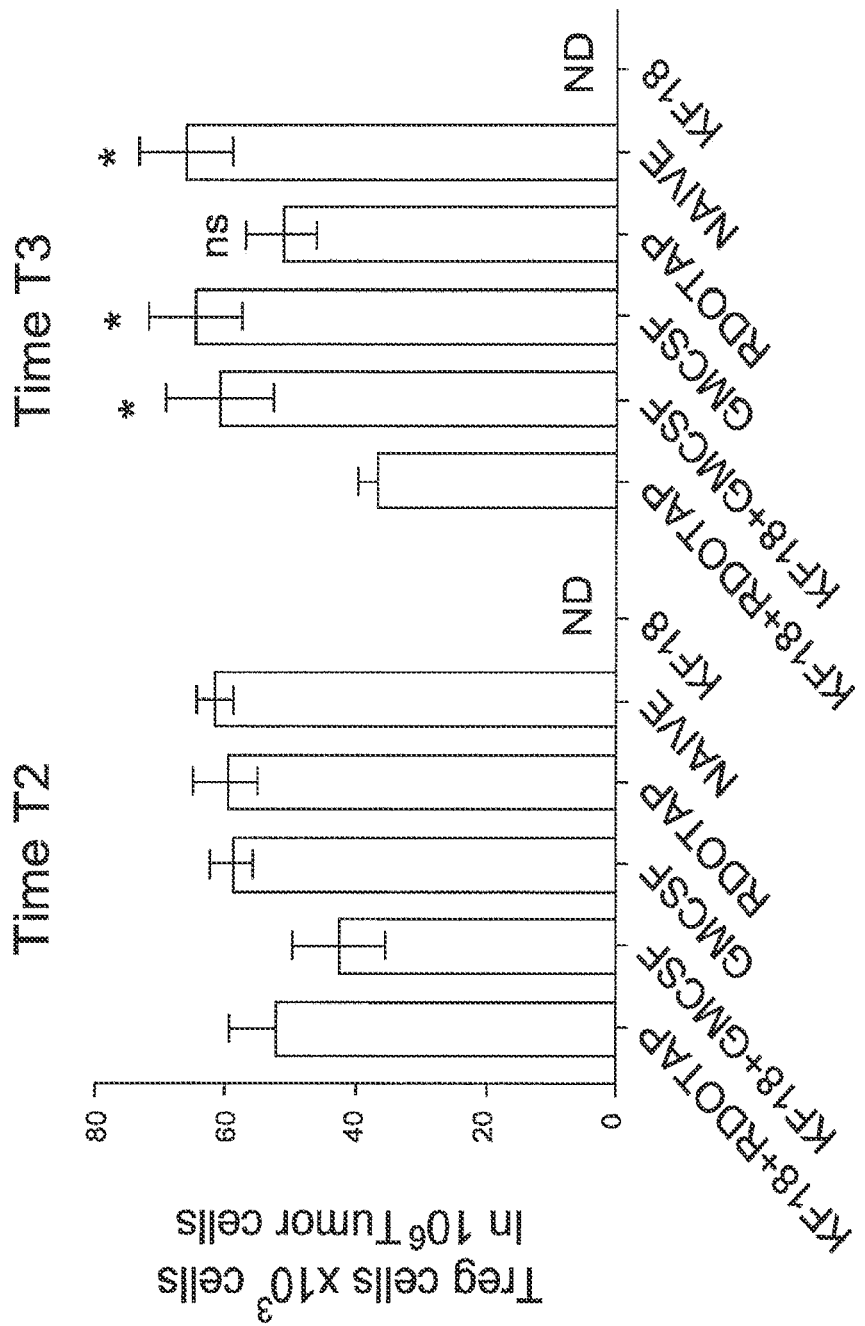
FIG. 16: Quantification of regulatory T cells within the tumors after treatment of tumor-bearing mice with various vaccines. Data represents mean±SEM of 4-5 mice in each group. *Statistically significant R-DOTAP+antigen compared to all other groups (other than R-DOTAP only). P<0.01.

On Day 19 flow cytometry was used to study the immunosuppressive tumor microenvironment, specifically the regulatory T cell population. T regulatory cells (CD45+CD3+ CD4+CD25+Foxp3+) cells infiltrated into tumors on day 14 and day 19. The results are presented in FIG. 16. The study demonstrates that a statistically significant reduction in the Treg population within the tumors of about 40% is observed within 1 week after vaccination only with the R-DOTAP+ antigen (P<0.01). No other group demonstrated any ability to reduce the population of Tregs other than the R-DOTAP group, although with this group, statistical significance was not achieved.

Of critical importance to the clinical efficacy of any immunotherapy is the ratio of immune suppressive cells to tumor targeting CD8+ T cells within the tumor microenvironment. A lower ratio of immune suppressor cells to CD8+ T cells promotes improved prognosis for anti-tumor benefit. The study shows a dramatically reduced Treg/CD8+ T-cell ratio of less than 0.13 for R-DOTAP+antigen compared to a ratio of approximately 1 for GM-CSF+antigen and for antigen only. The groups without tumor antigen exhibited a ratio of approximately 32 (shown in FIG. 17). Cationic lipids appear to promote the preferential expansion of the right phenotype of effector T-cells in preference to Tregs. This leads to a significant modification of the tumor micro-environment leading to "a shift in power" in favor of the CD8+ T-cells the attackers" over the immuno-suppressive Tregs "defenders", and thus highly effective immunotherapy.

Figure 18:
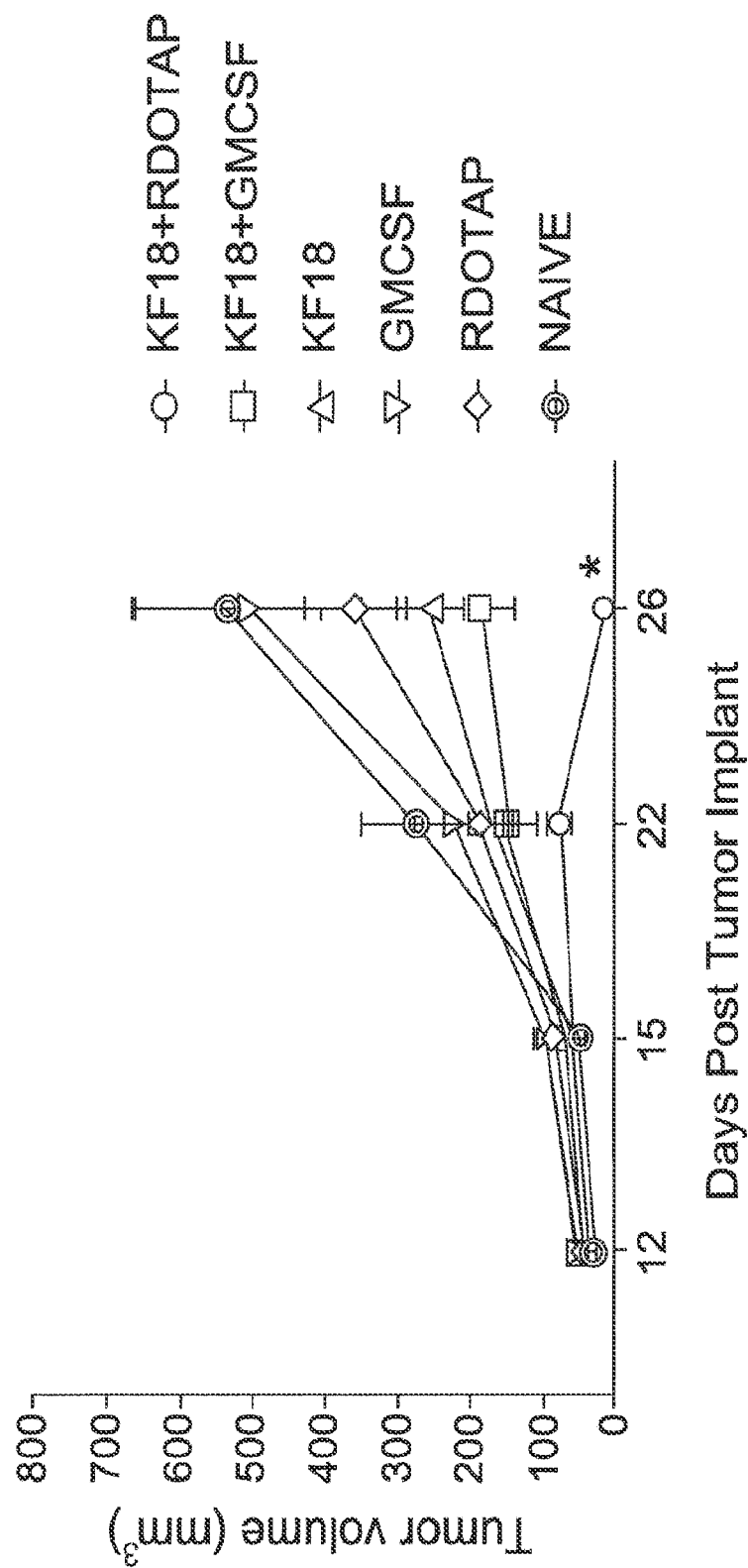
FIG. 18: Effect of vaccination on regression of established TC-1 tumors. *Statistically significant R-DOTAP+antigen tumor regression compared to all other groups. P<0.01.

The various formulations were evaluated for their impact on the established TC-1 tumors in the same study. FIG. 18 shows that the animal treated with R-DOTAP+antigen (Treg/CD8+ ratio<0.13) all had complete elimination of their tumors by Day 26. Tumor volumes were measured using calipers. The naïve mice group are tumor bearing mice that remained untreated. The HPV16 E7 peptide used in the vaccine is KF18. GM-CSF+antigen and antigen only (Treg/ CD8+ ratio of approx. 1.0) both did not induce any tumor regression but inhibited tumor growth leading to a tumor volume of about 200 mm$^3$ on Day 26. The third group of animals who were treated with either R-DOTAP or GM-CSF without antigen or left untreated (Treg/CD8+ ratio>30) had tumor volumes of 300-700 mm$^3$.

Figure 19:
FIG. 19: Quantification of CD8+ T-cell induction by IFN-γ ELISPOT. Data represents mean±SEM of 4-5 mice in each group. *Statistically significant R-DOTAP+antigen compared to all other groups. P<0.01. Dunnett's multiple comparisons test.

In this study, IFN-γ ELISPOT studies were also performed to quantify and understand the "quality" of tumor-specific T-cell generated. The animals were sacrificed on Day 26 and splenocytes used in the study. The results are shown in FIG. 19. The study shows that the R-DOTAP+ antigen formulation generated about 4-5 times higher quantities of IFN-γ compared to GM-CSF+antigen when the cells were stimulated with the HPV16 CD8+ mouse epitope RF9. This suggests that the cationic lipid is able to generate a "higher quality" of T-cell than GM-CSF due to the fact that in FIG. 11 the quantity of CD8+ T-cell infiltrating the tumor micro-environment is less than double what results with GM-CSF. The reasons for superior T-cell priming were evaluated in further studies.

Example 11

Figure 17:
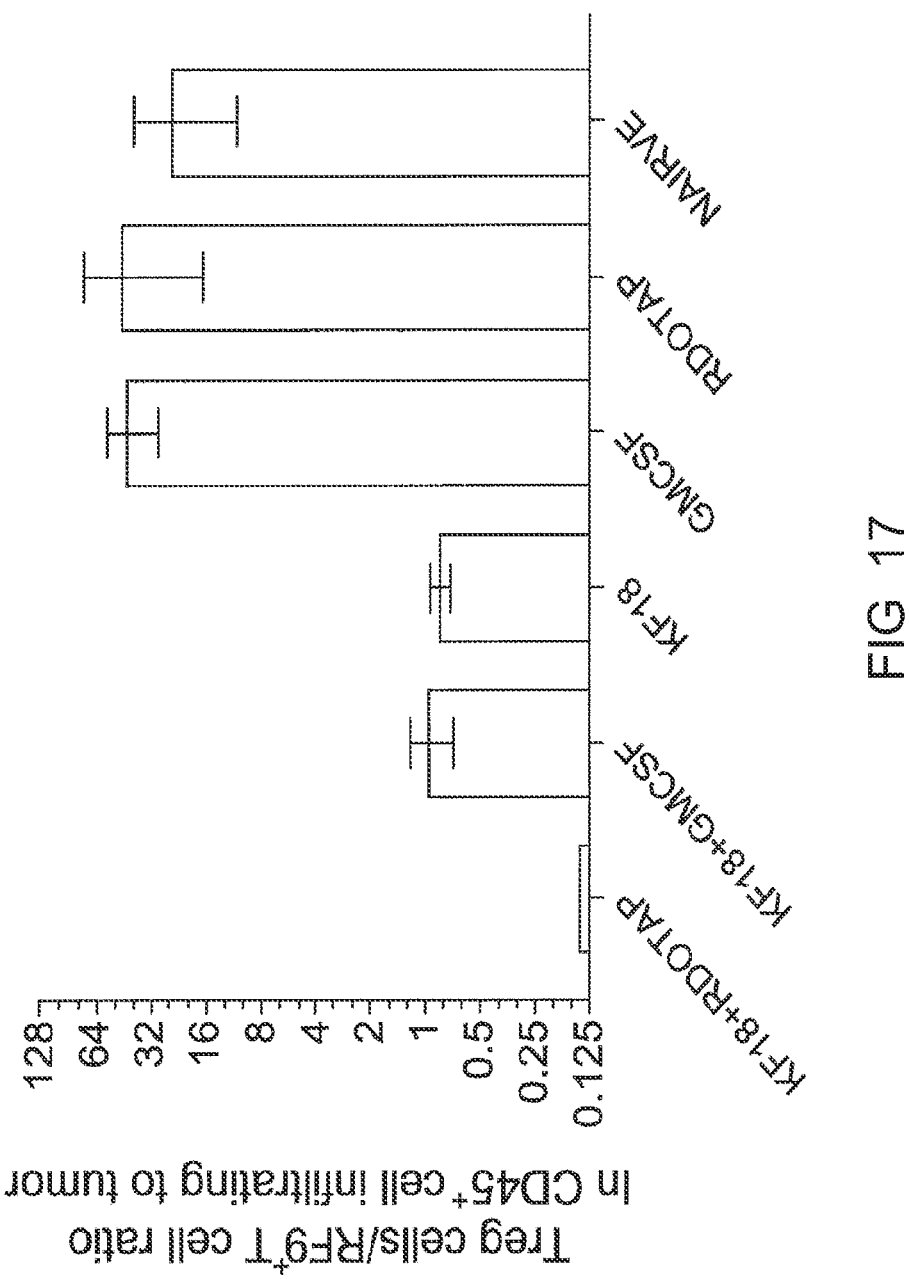
FIG. 17: Ratio of T regulatory cells (Tregs) to HPV16 E7-specific CD8+ T cells among CD45+ cells. Data represents mean±SEM of 4-5 mice in each group.
Figure 20:
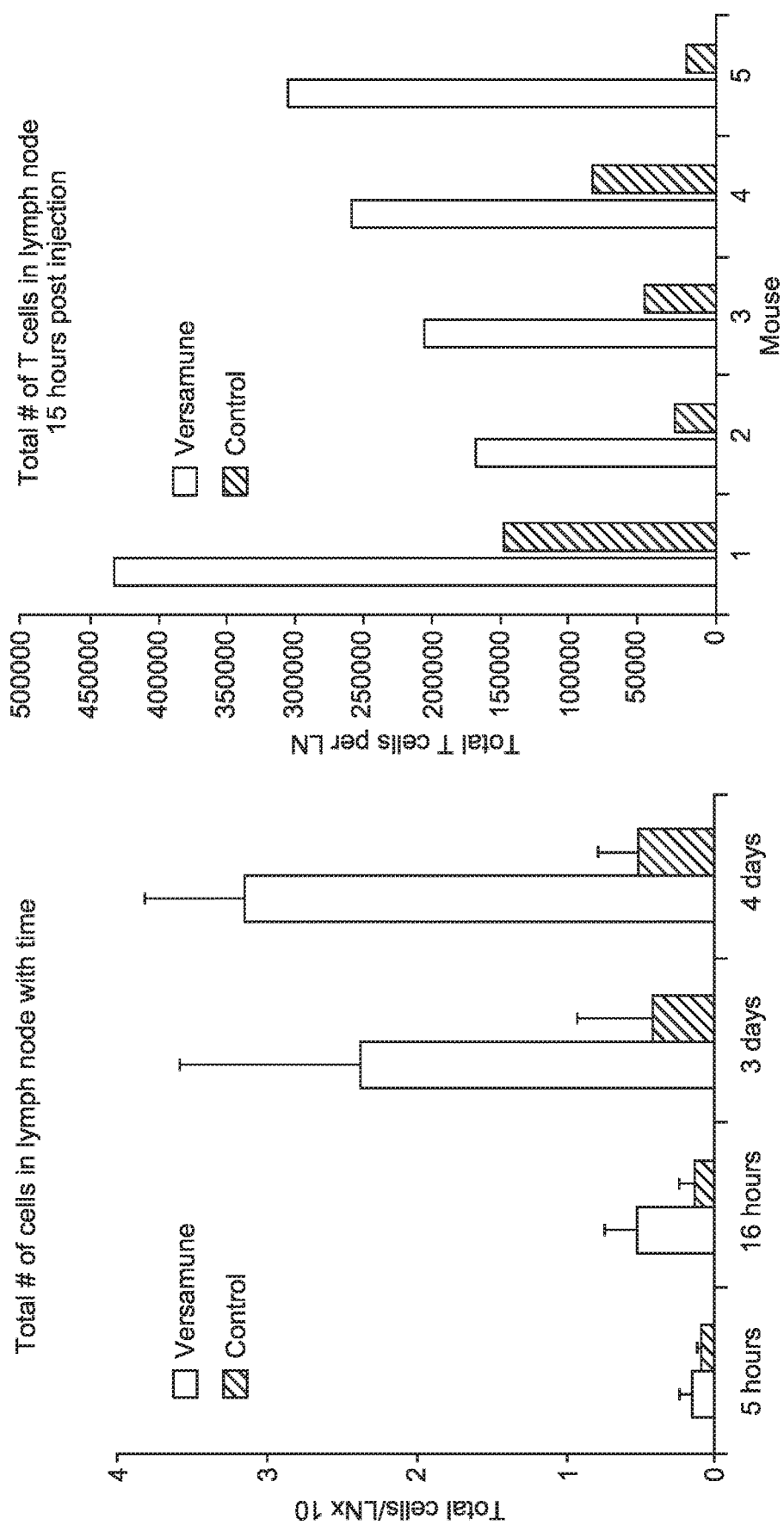
FIG. 20: Quantification of T-lymphocytes and total lymphocytes in the draining lymph nodes after vaccination with R-DOTAP cationic lipid.

Evaluation of R-DOTAP Vaccination on T and B-Cell Infiltration into the Lymph Nodes 12 mM R-DOTAP or sucrose as control were injected into the right and eft foot pad respectively of mice and the influx of T-cells and total lymphocytes into the draining lymph nodes were quantified by flow cytometry. In this experiment, 15 hours after vaccination the popliteal lymph nodes were removed and analysis performed. FIG. 17 shows that R-DOTAP induced significant infiltration of T-cells into the lymph node. In a second experiment the analysis was performed at 5 hours, 16 hours, 3 days and 4 days and lymphocyte infiltration into the lymph nodes was seen to increase over the 4-day period (FIG. 20). Five mice were used per study.

Example 12

Evaluating the Role of Chemokines on Lymphocyte Infiltration into the Lymph Nodes The primary objective of the current experiment was to utilize 5 mice to perform the study described in Example 7 and to visualize the homing of CFSE labeled adoptively transferred cells. The study included a population of cells that had been treated in vitro with pertussis toxin to inactivate chemokine receptors. Pertussis toxin and untreated cells were labeled with two different concentrations of CFSE so that they could be distinguished by flow cytometry. The lymphocytes should be induced to home to lymph nodes. However, if the DOTAP enhanced homing is due to chemokines, the pertussis toxin population should not be present, or should be present only at greatly reduced levels in the DLN.

Spleen cells were prepared from a single B6 mouse and divided in half. Half of the cells were treated with Pertussis toxin 100 ng/ml for 1 hour at 37° C. and washed. The two cell populations were then labeled with CFSE at two different concentrations so they could be distinguished by flow cytometry, and mixed together. The mix (10$^7$ cells) was injected i.v. into the tail vein of 5 B6 mice. The mice were then anesthetized and injected in the footpad with either sucrose (right footpad) or R-DOTAP (left footpad, 50 µl, 600 nmoles).

After 16 h, the mice were sacrificed and the popliteal LN and spleens harvested. The total cells recovered from left and right nodes from each mouse were counted. The transferred CFSE labeled lymphocytes also infiltrated the lymph node upon R-DOTAP vaccination. However, this did not occur with the pertussis treated cells, indicating that the cationic lipids induce the influx of lymphocytes into the lymph nodes and this phenomenon is most probably chemokine mediated.

Previous studies (Yan et al) suggested that cationic lipids induce chemokines CCL2, 3 and 4. However, these chemokines are not involved in lymph node homing. The study therefore suggests that the cationic lipids such as R-DOTAP also induce other lymph node homing chemokines like CCL21 or CXCL12.

Example 13

Induction of Cytokines and Chemokine within the Lymph Nodes

One of the key side effects of adjuvants is their induction of cytokines and increased presence of such cytokines in the blood circulation. Blood presence of cytokines often results in significant inflammatory responses which results in toxicities such as fever, nausea, vomiting, headaches, and extreme cases could lead to toxic shock and death. Cytokine storms are often associated with the administration of various adjuvants.

This study therefore focused on an evaluation of the systemic presence of cytokines after subcutaneous administration of cationic lipid vaccines. Human HLA-A2 mice that could recognize human HPV antigens were administered high and low doses of R-DOTAP+antigen.

Group 1:
Vaccinate mice with 100 µL of a 1:1 mixture of high dose R-DOTAP (3.4 mg/mL) and sucrose solution.
Group 2:
Vaccinate with 50 µg LPS as a positive control for cytokine induction
Group 3:
Vaccinate mice with 100 µL of high dose R-DOTAP+ HPV antigens (1:1 Mixture of RDOTAP 3.4 mg/mL, and HPVMix 0.14 mg/mL)
Group 4:
Vaccinate mice with 100 µL of low dose R-DOTAP+HPV antigens (1:1 Mixture of RDOTAP 0.34 mg/mL, and HPVMix 0.14 mg/mL)
After a single vaccination all mice were bled as follows:
1. Pre bleed (prior to vaccination)
2. 12 hours
3. 24 hours
4. 48 hours Approximately 200 µL of blood was withdrawn from each mouse at the above specified time points.

The cytokine analysis was performed by Luminex Assay following the manufacturer's instructions.

As a positive control, the mice were also vaccinated with the well-studied toll-like-receptor (TLR) agonist lipopolysaccharide (LPS).

Figure 21:
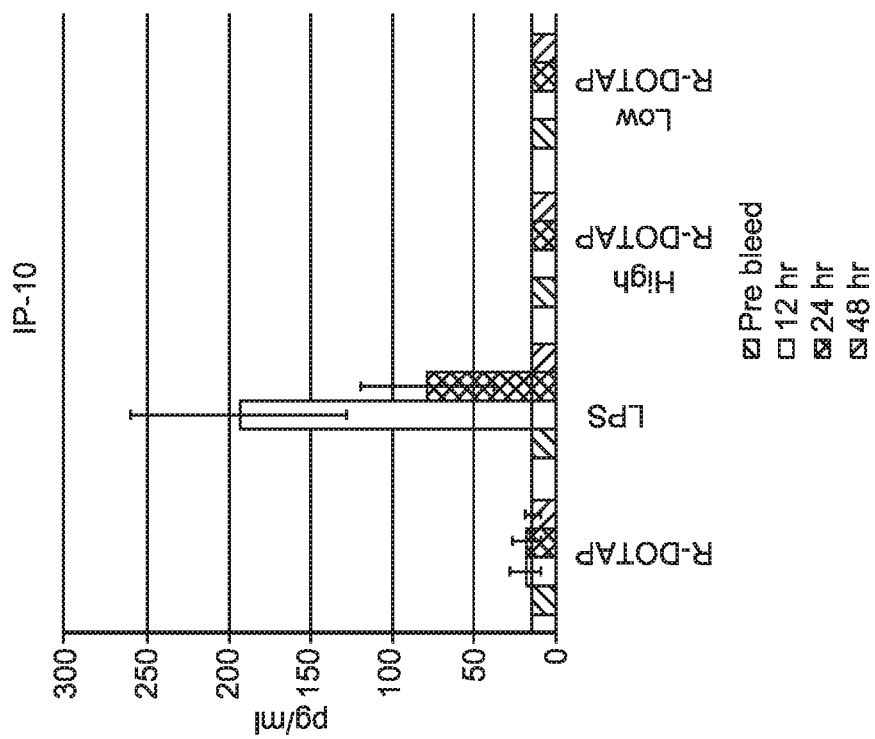
FIG. 21: Quantification of MCP-1 and IP-10 levels in response to vaccination. The Figure shows levels of MCP-1 and IP-10 prior to 12 hours, 24 hours, and 48 hours following vaccination.
Figure 21:
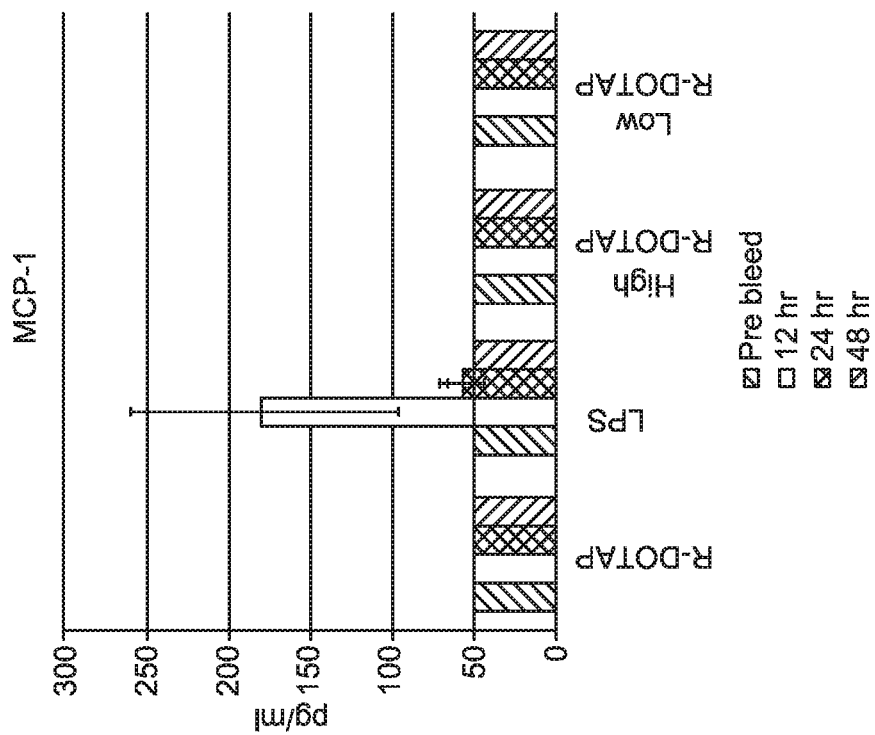

Study Results:Mouse serum was analyzed using a Luminex Mouse cytokine 20-plex panel (cytokines listed below). Cytokine intensity levels were quantitated by comparing to a cytokine standard run in the same plate using Luminex software. The positive control group (LPS) demonstrated increases in the systemic levels of IL-12, IP-10, KC, MCP-1 & MIG upon vaccination. No systemic induction of any of the studied cytokines and chemokines was induced by high and low doses of PDS0101 beyond the pre-vaccination baseline as shown in FIG. 21.

Mouse Cytokine 20-plex panel: FGF, IL-1b, IL-10, IL-13, IL-6, IL-12(P40/P70), IL-17, MIP-1a, GM-CSF, MCP-1, IL-5, VEGF, IL-1a, IFN-y, TNFa, IL-2, IP-10, MIG, KC, IL-4.

The results of the study are shown in FIG. 20 for MCP-1 (CCL2) and IP-10 which are typical of the results seen for all tested cytokines. The study demonstrates that in the case of the cationic lipid the cytokine and chemokine induction appears to be limited predominantly to the lymph nodes. In the case of LPS, a typical TLR agonist, cytokine induction is not limited to the lymph nodes but a systemic spike in cytokine levels is observed within 12 hours of vaccination. The lack of cytokine presence in the blood circulation suggests that the cationic lipids provide a uniquely safe means of immunotherapy to alter the tumor micro-environment.

EQUIVALENTS

Those skilled in the art will recognize or be able to ascertain using no more than routine experimentation, many equivalents to the specific embodiments of the invention described herein. Such equivalents are intended to be encompassed in the following claims.

We claim:

1. A method of altering a tumor microenvironment by reducing the population of regulatory T-cells in the tumor microenvironment comprising:
    administering to a subject having a tumor a dendritic cell vaccine composition,
    wherein the dendritic cell vaccine composition comprises:
        a cationic lipid comprising R-DOTAP; and
        a population of isolated dendritic cells, wherein the dendritic cells have been stimulated ex vivo by at least one antigen,
        wherein the at least one antigen is a tumor associated antigen specific for the tumor, and
    wherein administering the dendritic cell vaccine composition results in the altering of the tumor microenvironment.

2. The method of claim 1, wherein the tumor-associated antigen may be protein, peptide, RNA or DNA based.

3. The method of claim 1, wherein the composition further comprises an adjuvant, growth factor, cytokines or an agent that combats immune suppression.

4. The method of claim 1, wherein the tumor-associated antigen is an HPV antigen.

5. The method of claim 4, wherein the HPV antigen is HVP16E7.

6. The method of claim 3, wherein the cytokine is GM-CSF.

* * * * *

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Lys Ser Ser Ser Ile Ile Asn Phe Glu Lys Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 2

Ser Ile Ile Asn Phe Glu Lys Leu
1               5

<210> SEQ ID NO 3
<211> LENGTH: 30
<212> TYPE: PRT
<213> ORGANISM: Artificial Sequence
<220> FEATURE:
<223> OTHER INFORMATION: Synthetic

<400> SEQUENCE: 3

Ser Met Leu Val Leu Leu Pro Asp Glu Val Ser Gly Leu Glu Gln Leu
1               5                   10                  15

Glu Ser Ile Ile Asn Phe Glu Lys Leu Thr Glu Trp Thr Ser
            20                  25                  30

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gly Gln Ala Glu Pro Asp Arg Ala His Tyr Asn Ile Val Thr Phe
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Arg Ala His Tyr Asn Ile Val Thr Phe
1               5
```